(12) United States Patent
Mahfouz

(10) Patent No.: US 9,901,463 B2
(45) Date of Patent: Feb. 27, 2018

(54) KINEMATIC ALIGNMENT AND NOVEL FEMORAL AND TIBIAL PROSTHETICS

(71) Applicant: Mohamed R. Mahfouz, Knoxville, TN (US)

(72) Inventor: Mohamed R. Mahfouz, Knoxville, TN (US)

( * ) Notice: Subject to any disclaimer, the term of this patent is extended or adjusted under 35 U.S.C. 154(b) by 295 days.

(21) Appl. No.: 14/686,685

(22) Filed: Apr. 14, 2015

(65) Prior Publication Data

US 2016/0008143 A1    Jan. 14, 2016

Related U.S. Application Data

(60) Provisional application No. 61/979,034, filed on Apr. 14, 2014, provisional application No. 62/013,198, filed on Jun. 17, 2014, provisional application No. 62/022,894, filed on Jul. 10, 2014.

(51) Int. Cl.
| | |
|---|---|
| *A61F 2/46* | (2006.01) |
| *A61B 17/15* | (2006.01) |
| *A61B 17/90* | (2006.01) |
| *A61F 2/38* | (2006.01) |
| *A61F 2/30* | (2006.01) |

(52) U.S. Cl.
CPC ............ *A61F 2/461* (2013.01); *A61B 17/157* (2013.01); *A61F 2/4684* (2013.01); *A61B 2017/90* (2013.01); *A61F 2/30942* (2013.01); *A61F 2/389* (2013.01); *A61F 2002/4633* (2013.01); *A61F 2002/4687* (2013.01)

(58) Field of Classification Search
CPC ......... A61F 2/461; A61F 2/4684; A61F 2/389
See application file for complete search history.

(56) References Cited

U.S. PATENT DOCUMENTS

| | | | | |
|---|---|---|---|---|
| 4,681,589 | A * | 7/1987 | Tronzo | A61F 2/30734 623/22.32 |
| 4,944,757 | A * | 7/1990 | Martinez | A61F 2/389 623/20.15 |
| 5,318,571 | A * | 6/1994 | Benson | A61F 2/4657 606/102 |
| 5,423,828 | A * | 6/1995 | Benson | A61F 2/4657 606/102 |
| 5,507,824 | A * | 4/1996 | Lennox | A61F 2/34 623/22.25 |
| 5,782,925 | A * | 7/1998 | Collazo | A61F 2/4684 623/20.28 |
| 6,063,091 | A * | 5/2000 | Lombardo | A61B 17/1735 606/102 |

(Continued)

FOREIGN PATENT DOCUMENTS

| | | | |
|---|---|---|---|
| EP | 15779900 | 9/2017 | |
| WO | WO 2013103642 A2 * | 7/2013 | ......... G06K 9/00335 |
| WO | 2015160852 | 10/2015 | |

*Primary Examiner* — Zade Coley
(74) *Attorney, Agent, or Firm* — Ryan Willis; Willis IP

(57) ABSTRACT

A tibial component placement guide for use in a knee arthroplasty procedure involving a knee joint comprising a tibia, a patella, and a femur, the guide comprising an overlay configured to be overlaid a resected tibia, the overlay including at least one of an indicia and an opening indicative of at least one of an orientation and a position of at least one of a first axis of the femur, a second axis of the femur, and a first axis of the patella.

25 Claims, 67 Drawing Sheets

(56) References Cited

U.S. PATENT DOCUMENTS

| | | | | |
|---|---|---|---|---|
| 6,355,045 B1* | 3/2002 | Gundlapalli | ....... | A61B 17/1764 |
| | | | | 606/86 R |
| 6,494,913 B1* | 12/2002 | Huebner | ................... | A61F 2/40 |
| | | | | 606/87 |
| 6,645,215 B1* | 11/2003 | McGovern | ........... | A61B 17/157 |
| | | | | 606/102 |
| 2003/0233145 A1* | 12/2003 | Landry | ................... | A61F 2/442 |
| | | | | 623/17.11 |
| 2010/0298894 A1 | 11/2010 | Bojarski et al. | | |
| 2010/0305575 A1 | 12/2010 | Wilkinson et al. | | |
| 2010/0305711 A1* | 12/2010 | McKinnon | .......... | A61B 17/155 |
| | | | | 623/20.32 |
| 2013/0006371 A1 | 1/2013 | Wogoman et al. | | |
| 2013/0317510 A1* | 11/2013 | Couture | .............. | A61B 17/154 |
| | | | | 606/88 |
| 2013/0331850 A1* | 12/2013 | Bojarski | ............... | A61F 2/4657 |
| | | | | 606/102 |
| 2014/0208578 A1* | 7/2014 | Linderman | .......... | A61B 17/155 |
| | | | | 29/592 |
| 2014/0228860 A1* | 8/2014 | Steines | ............... | A61F 2/30942 |
| | | | | 606/130 |

* cited by examiner

| Ligament | Patient | Degree of Flexion | | | | | | | |
|---|---|---|---|---|---|---|---|---|---|
| | | 0 | 20 | 40 | 60 | 80 | 100 | 120 | Max |
| ACL | 1 | 34.637 | 33.848 | 32.596 | N/A | 28.423 | 29.557 | 30.751 | 31.684 |
| | 2 | 40.657 | 35.303 | 33.927 | 32.605 | 33.873 | 30.742 | 28.462 | 30.601 |
| | 3 | 37.004 | 34.540 | 31.389 | 31.344 | 30.381 | 27.505 | 28.688 | 31.404 |
| | 4 | 32.045 | 32.355 | 32.375 | 31.416 | 31.389 | 31.418 | 28.426 | 28.384 |
| | 5 | 44.232 | 41.869 | 38.679 | 42.583 | 40.573 | 37.572 | 33.591 | 33.606 |
| | Avg | 37.715 | 35.583 | 33.793 | 34.487 | 32.928 | 31.359 | 29.983 | 31.136 |
| PCL | 1 | 31.824 | 31.824 | 33.646 | N/A | 40.658 | 40.904 | 40.979 | 44.204 |
| | 2 | 32.088 | 36.082 | 42.631 | 44.207 | 47.090 | 47.908 | 50.101 | 48.937 |
| | 3 | 25.729 | 24.607 | 32.677 | 36.601 | 39.9489 | 43.586 | 46.400 | 45.869 |
| | 4 | 26.469 | 26.436 | 31.387 | 31.346 | 38.395 | 43.764 | 41.729 | 40.809 |
| | 5 | 23.358 | 27.535 | 32.592 | 35.468 | 38.385 | 39.415 | 43.722 | 43.609 |
| | Avg | 27.894 | 29.297 | 34.586 | 36.905 | 40.934 | 43.115 | 44.586 | 44.665 |

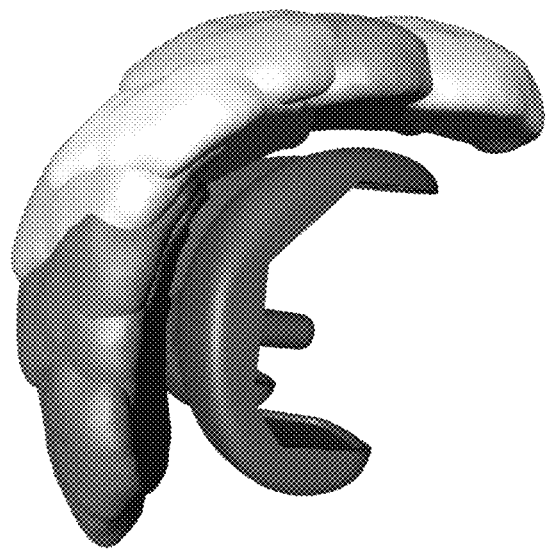
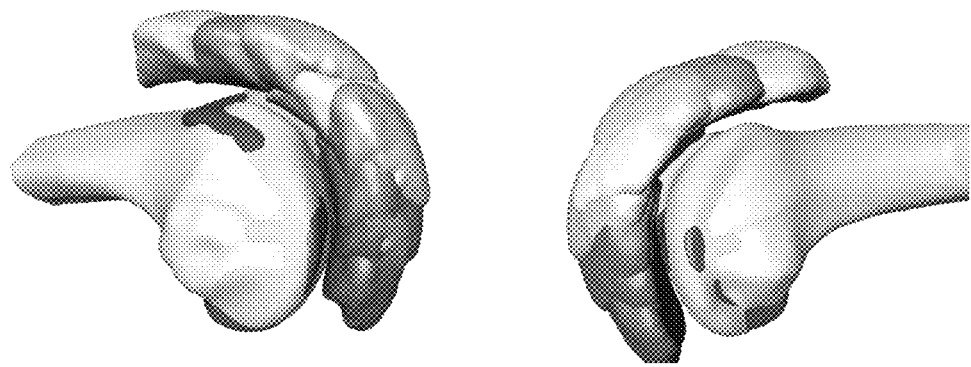
FIGS. 38A-38C

|        |            | Angle Between Femur PCA and Tibia PCA | Angle Between Femur PCA and Cobb Axis |
|--------|------------|---------------------------------------|---------------------------------------|
| Female | mean       | 3.30                                  | 5.98                                  |
|        | Stdev      | 2.72                                  | 5.38                                  |
|        | t-test     | 0.02                                  | 0.06                                  |
|        | F-test     | 0.06                                  | 0.00                                  |
|        | Difference | 1.76                                  | -1.82                                 |
|        | Power Test | 87.00                                 | 127.00                                |
| Male   | mean       | 5.06                                  | 4.15                                  |
|        | Stdev      | 3.70                                  | 2.68                                  |

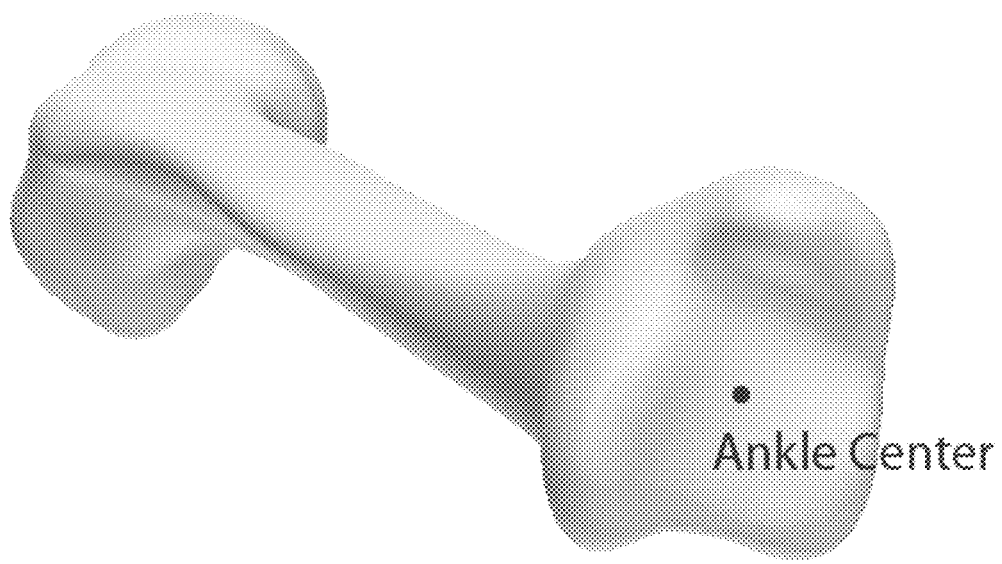
FIG. 93
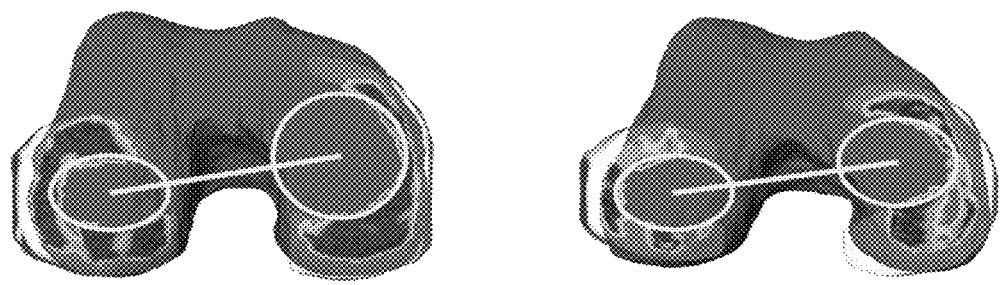
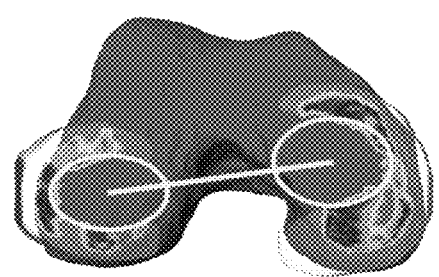
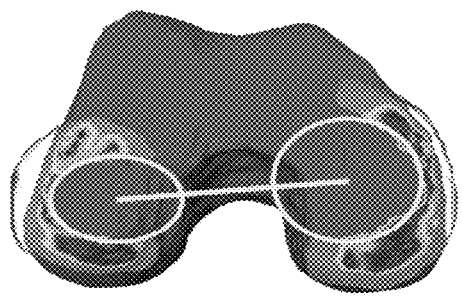
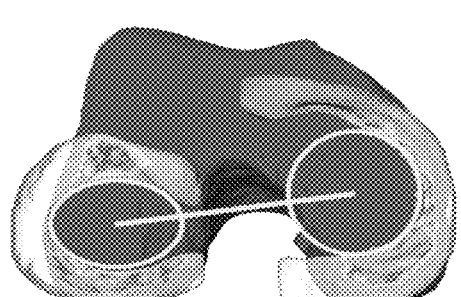
FIGS. 94A-94D

KINEMATIC ALIGNMENT AND NOVEL FEMORAL AND TIBIAL PROSTHETICS

CROSS REFERENCE TO RELATED APPLICATIONS

The present application claims the benefit of U.S. Provisional Patent Application Ser. No. 61/979,034, entitled, "KINEMATIC ALIGNMENT OF FEMORAL AND TIBIAL COMPONENTS," filed Apr. 14, 2014, and U.S. Provisional Patent Application Ser. No. 62/013,198, entitled, "KINEMATIC ALIGNMENT OF FEMORAL AND TIBIAL COMPONENTS," filed Jun. 17, 2014, and U.S. Provisional Patent Application Ser. No. 62/022,894, entitled, "KINEMATIC ALIGNMENT OF FEMORAL AND TIBIAL COMPONENTS," filed Jul. 10, 2014, the disclosure of each of which is incorporated herein by reference.

INTRODUCTION TO THE INVENTION

The present disclosure is directed to knee kinematics as well as techniques, surgical guides, and orthopedic prosthetics to enhance knee arthroplasty.

Knee arthritis causes debilitating pain affecting activities of daily living. When pain is not well controlled by non-operative treatments and the failure in managing disease' symptoms (pain, stiffness, swelling, and/or bony spurs), Total Knee Arthroplasty (TKA) is recommended if the patient is medically fit for the surgery and has no active infection.

One common objective in TKA is to restore normal kinematics. However, what are normal kinematics? Is it the relationship between ligaments menisci and articular surfaces of femur, tibia and patella or the distribution of contact stresses across the articulating joint as symmetrically as possible, avoiding overloading of the one compartment? Although trying to achieve the same goal, these two philosophies require different surgical techniques—one to provide a restoration to normal anatomy (in the case of osteoarthritis), second is to correct defective anatomy (i.e. varus/valgus).

The former philosophy is a measured resection technique where bone and cartilage are replaced by implants that are of generally the same thickness. The latter philosophy is a balanced flexion gap technique that may require altering the patient's pre-arthritic anatomy. The major assumption underlying this philosophy is many patients who develop medial compartment arthritis of the knee are bowlegged, or walk with a varus thrust, since childhood. Therefore, restoring the condition of the pre-arthritic alignment would result in greater varus component position than is generally considered acceptable for knee arthroplasty.

However, whether using measured resection or flexion gap surgical technique, the predominant method of alignment is the mechanically aligned (mechanical neutral) TKA. In this method, the surgeon cuts the distal femur and the proximal tibia perpendicular to the mechanical axes (Appendix A). The second alignment method, which is gaining more acceptance, is the kinematically aligned TKA. The goal of this latter method is to restore the natural difference in symmetry and varus-valgus laxity between 0 degrees of extension and 90 degrees of the normal knee (Appendix B).

Prosthetic placement in TKA is a complex problem related to the complex shapes of the femur and tibia, out of plane geometrical relationships of the articular surfaces and bones, and the additive factor of ligamentous changes, anatomical variation and deformity resulting from chronic disease. The relationship between axial and rotational alignment is not well documented. It is known that decreased femoral anteversion in Caucasians patients and decreased tibia torsion in Asian patients can be associated with osteoarthritis. In one study, genu varum has been associated with external tibial torsion. It is likely that both deformations coexist in a typical three-dimensional deformity. For example, an externally rotated leg with the knee flexed will appear as a varus deformity. A logical conclusion is that detrimental joint overloads can result from combined rotational and axial malalignment.

The instant disclosure involved analyzing both alignment methods and coming to the conclusion that the current implant designs (femur, tibia and instruments) are not well suited for the kinematic aligned TKA.

Surgical techniques in TKA have relied on recreating primarily the two dimensional mechanical axis alignment in the coronal plane (see FIGS. 1A-1C and 2A), followed by carefully balancing the extension and flexion gaps (see FIG. 2B). Intrinsic to the latter process is coronal placement of the prosthetic implants in the sagittal plane. While distal measured resection methods attempt to restore "normal" anatomy, by placing implants in the "normal" position using mechanical alignment, this fails to account for underlying rotational deformities. For example, increased knee version or external rotation of the transtibial axis compared to the femoral transepicondylar axis may be an underlying deformity that contributes to varus misalignment.

In addition, the cuts that are made to the femur and tibia during TKA may change the angle and the level of natural joint line causing abnormal tightening or slackening of the collateral, retinacular, and posterior cruciate ligaments and abnormal kinematics. The undesirable consequences of the abnormal kinematics are instability, motion loss, accelerated component wear and component loosening from uneven load-sharing between compartments.

In order to better understand what the term natural kinematics means several studies have been performed and published by various authors. One gold standard method requires analysis of digital fluoroscopic images, taken during a series of activities. For each activity the pose of the femur relative to the tibia is tracked throughout—allowing for the capture of the entire kinematic profile for each subject during activity (this process is well described in the document—and is easily referenced to existing literature if space saving is desired). Both contact maps, tracking the closest point between the two surfaces, and the instantaneous axis of rotation (helical axis) suggest that the knee pivots clearly about the medial side, and rolls back on the lateral side. In fact, during deep knee bend, the medial side may experience slight anterior translation—a motion sometimes referred to as paradoxical motion. Interestingly, this helical axis very closely follows the sagittal kinematic plane during all activity. This is shown in FIGS. 22-31.

Another clue as to how the normal knee behaves is uncovered with investigation of the ligament lengths during flexion. Looking at the MCL and LCL during flexion shows, as with the contact analysis, that the MCL length changes very little during flexion compared to the LCL length—and has significantly less translation than the LCL. This would suggest a medial side which is considerable tighter throughout flexion than the lateral. Further, the LCL is longest at full extension—suggesting a rigid joint at extension and a fairly lax lateral side in extension, but still fairly tight medially. Finally, when examining the PCL/ACL, we again see significant length changes, but in a way that relates the PCL length inversely to the ACL length, suggesting an "exchange" of load during flexion. It is worth mentioning that the posterior translation of the lateral side is not a linear one, but happens rapidly as the lateral curvature of the femur transitions from the relatively flat surface in early flexion and extension to the more curved posterior surface in deeper flexion. The soft tissue profiles of the normal knee during activity are totally counterintuitive to mechanical alignment and balanced gaps. In fact, this helps to explain why mechanically aligned knees cannot achieve normal kinematics—the joint balance and joint lines have been altered significantly. Thus a method is required which can align the implant in a way to restore, or maintain, natural loading of the knee (not equal medial/lateral loads) and normal kinematics.

As part of the instant disclosure, X-ray fluoroscopy may be utilized to generate two dimensional (2D) fluoroscopy images of components of a joint across a range of motion of the joint. Thereafter, three dimensional models of the patient's anatomy, having already been constructed from static images (e.g., MRI, CT, X-ray, etc.) taken of the patient anatomy, need to be registered to the 2D fluoroscopy images. In the instance circumstance, 2D fluoroscopy images are taken of a human knee joint at distinct points along its range of motion, as well as construction of a 3D component model of the human knee joint. In exemplary form, perspective images of the 3D joint model (comprising the femur, tibia and the patella (with the fibula)) are overlaid onto the 2D fluoroscopy images, across the range of motion, taking into account the position of the X-ray source and to the image intensifier. When the 3D joint model is correctly registered (i.e., overlaid) with the 2D fluoroscopy images, the relative pose of the components of the 3D joint model is the same as the pose of those components at the time the fluoroscopy images were created. Registering the joint model to the 2D fluoroscopy images across selected frames of the range of motion is utilized to calculate the relative pose between the three bones over the entire range of motion.

The pose of a rigid body $\{A\}$ with respect to another coordinate system $\{B\}$ can be represented by a six element vector ${}^B_A x = ({}^B x_{Aorg}, {}^B y_{Aorg}, {}^B z_{Aorg}, \alpha, \beta, \gamma)_T$, where ${}^B p_{Aorg} = ({}^B x_{Aorg}, {}^B y_{Aorg}, {}^B z_{Aorg})^T$ is the origin of frame $\{A\}$ in frame $\{B\}$, and ($\square\square\square\square$) are the angles of rotation of $\{A\}$ about the (z, y, x) axes of $\{B\}$. An alternative representation of orientation is to use three elements of a quaternion; the conversion between Euler angles and quaternions is straightforward.

Equivalently, pose can be represented by a 4×4 homogeneous transformation matrix:

$$ {}^B_A H = \begin{pmatrix} {}^B_A R & {}^B p_{Aorg} \\ 0 & 1 \end{pmatrix} $$

where ${}^B_A R$ is the 3×3 rotation matrix corresponding to the angles ($\square\square\square\square$). The letter H designates the equivalent 4×4 homogeneous transformation matrix.

Homogeneous transformations are a convenient and elegant representation. Given a homogeneous point ${}^A p = ({}^A x_p, {}^A y_p, {}^A x_{p,1})^T$, represented in coordinate system $\{A\}$, it may be transformed to coordinate system $\{B\}$ with a simple matrix multiplication ${}^B p = {}^B_A H \, {}^A p$. The homogeneous matrix representing the pose of frame $\{B\}$ with respect to frame $\{A\}$ is just the inverse of the pose of $\{A\}$ with respect to $\{B\}$; i.e., ${}^A_B H = {}^B_A H^{-1}$. Finally, if one knows the pose of $\{A\}$ with respect to $\{B\}$, and the pose of $\{B\}$ with respect to $\{C\}$, then the pose of $\{A\}$ with respect to $\{C\}$ is easily given by the matrix multiplication ${}^C_A H = {}^C_B H \, {}^B_A H$.

The pose of each bone in the joint model is represented by a 4×4 homogeneous transformation matrix ${}_{Tib}^{Fem} H$ that is comprised of rotation matrix and translation vector. The rotation matrix ${}_{fluoro}^{Model} R_{xyz}(\gamma, \beta, \alpha)$ is given by:

$$ {}_{fluoro}^{Model} R_{xyz}(\gamma, \beta, \alpha) = R_z(\alpha) R_y(\beta) R_x(\gamma) $$

$$ = \begin{bmatrix} \cos(\alpha) & -\sin(\alpha) & 0 \\ \sin(\alpha) & \cos(\alpha) & 0 \\ 0 & 0 & 1 \end{bmatrix} * \begin{bmatrix} \cos(\beta) & 0 & \sin(\beta) \\ 0 & 1 & 0 \\ -\sin(\beta) & 0 & \cos(\beta) \end{bmatrix} * \begin{bmatrix} 1 & 0 & 0 \\ 0 & \cos(\gamma) & -\sin(\gamma) \\ 0 & \sin(\gamma) & \cos(\gamma) \end{bmatrix} $$

$$ {}_{fluoro}^{Model} R_{xyz}(\gamma, \beta, \alpha) = \begin{bmatrix} r_{11} & r_{12} & r_{13} \\ r_{21} & r_{22} & r_{23} \\ r_{31} & r_{32} & r_{33} \end{bmatrix} $$

whereby, $\beta$, and $\alpha$ are the model's angles of rotations about x, y, and z axes, and the translation vector is ${}^{Model} p_{fluoro} = ({}^{Model} x_{fluoro}, {}^{Model} y_{fluoro}, {}^{Model} z_{fluoro})^T$ respectively. Therefore, the relative pose) of the femur with respect to the tibia is then calculated using the equation ${}_{Tb}^{Fem} H = {}_{Fluoro}^{Tib} H \, {}_{Fem}^{Fluoro} H$ (similarly ${}_{Fem}^{Pat} H = {}_{Fluoro}^{Femb} H \, {}_{Pat}^{Fluoro} H$).

In accordance with the instant disclosure, three methods were utilized for analyzing the relative motion of the femur and tibia across a range of motion of a knee joint. The first method was the method of screw axis decomposition, also called the helical axis of motion method. In this method, the axis in space about which the moving body rotates is determined. Simply put, the motion of a rigid body from one time instant to another can be decomposed as a rotation about an axis, plus a translation along that axis. The axis is represented as a point on the axis ($C_0$), along with a unit vector K specifying the direction of the axis. The point $C_0$ and the vector K are represented in the coordinate system of the body at the first time instant. An initial computation uses the rotation matrix R to compute the rotation axis and angle:

$$ \theta = \arccos((R_{11} + R_{22} + R_{33} - 1)/2) $$

$$ K = [R_{32} - R_{23}, R_{13} - R_{31}, R_{21} - R_{12}]^T / (2 \sin(\theta)) $$

Thereafter, the components of translation parallel and perpendicular to the rotation axis is computed:

$$ T_{para} = (T \cdot K) K $$

$$ T_{perp} = T - T_{para} $$

Then, the vector $C_0$ is computed to the screw axis:

$$ M = I_{3 \times 3} - R $$

$$ C_0 = (M^T M)^{-1} M^T T_{perp} $$

where $I_{3 \times 3}$ is the 3×3 identity matrix. Note that the matrix M is singular.

The point $C_0$ is an arbitrary point on the axis, which may be far away. Sometimes it is useful to choose a specific point on the axis. In the instant application, it is useful to find the point on the axis that is the intersection of the axis with the XY plane of the body:

$$ s = C_{0z} - K_z $$

$$ P = C_0 + sK $$

where $C_{0z}$ and $K_z$ are the z components of the vectors $C_0$ and K, respectively. Here, s is the distance from C0 to the XY plane, along the vector K. The point P is in the XY plane of the body at the first position.

The location and orientation of the helical axis of motion may be defined with respect to the coordinate system of the tibia. If the knee was a simple hinge joint, with pure rotation about the medial axis, then the helical axis of motion would be a stationary line perpendicular to the sagittal plane. However, the motion of the knee joint is more complex than a simple hinge joint, and can include translation as well as rotation about other axes. As a result, the helical axis of motion is not exactly perpendicular to the sagittal plane, and is not fixed in space. FIGS. 4A and 4B show how the helical axis of motion moves during the flexion sequence (from 0 degrees to 120 degrees of flexion) for a normal knee joint. FIGS. 4C and 4D show the geometrical center of the femur rotating around the helical axis of motion.

A second method used to analyze the relative motion of the knee joint pursuant to the instant disclosure involved tracking the contact paths of the femur on the tibia during a range of motion of the knee joint as evidenced by fluoroscopic images. The minimum point on the surface of the medial and lateral condyles for each respective flexion angle was calculated automatically as the closest points to the tibia and projected down onto the tibial plateau (see FIGS. 5A-5D). This method may be preferable because the process for obtaining these minimum points is automated and reproducible, thus reducing or eliminating human errors. It should be noted that these contact points are also located in the coordinate space of the tibia.

As part of this second method, all anterior-posterior (AP) measurements were made with respect to a plane (frontal) that is located at the geometric center of the tibia (see FIG. 6), while the geometric center was calculated automatically. If the AP contact position of the condyle is more anterior than this plane, the AP position will be positive. In contrast, if the contact position is more posterior than this plane, the AP position will be negative. For each selected frame of the fluoroscopy image sequence of a patient's knee joint, femorotibial contact paths were determined for the medial and lateral condyles and plotted with respect to knee flexion angle (see FIGS. 7-9).

As part of this second method, fluoroscopic images of a patients' knee joints with normal structure and kinematics were obtained that included in the range of motion a deep knee bend. Patient's performing this deep knee bend experienced posterior femoral translation of their lateral condyle and minimal change in the position of the medial condyle (see FIG. 7). The average amount of posterior femoral translation of the lateral condyle was 28.68 mm (standard deviation, 5.45), whereas the average medial condyle translation was 1.5 mm (standard deviation, 2.19), in the posterior direction. The majority of the posterior femoral translation of the lateral condyle appeared to occur in the first 75° knee flexion (see FIG. 8). Posterior femoral translation was not always continuous with increasing knee flexion because small amounts of paradoxical anterior translation of femorotibial contact were observed in midflexion, particularly medially.

As evidenced from the fluoroscopic images of patients with normal knee structure and kinematics, patients' knees experienced a normal axial rotation pattern during a deep knee bend (tibia internally rotating with increased knee flexion), because the posterior translation of femorotibial contact laterally was greater than that observed medially (see FIG. 7). The average amount of axial rotation for the normal subjects from 0° to 120° flexion was 18.39° (standard deviation, 6.09) in the normal direction. The majority of this rotation occurred in the first 30° knee flexion (average, 9.35°, see FIG. 9). Anteroposterior contact points for patients with normal knees are represented in FIGS. 10A-10E. Rotational movements are best represented by describing the helical axis of motion across a range of motion.

The helical axis of motion is an imaginary line in space, around which the femur rotates. Because of the out of plane motion of the knee (6 degrees of freedom), this axis is almost never perpendicular to the sagittal plane (see FIGS. 11A-11D). By closely looking at the femoral rotations in represented in FIGS. 11A-11D, it was observed that the helical axis translates posteriorly. Therefore, posterior femoral translation is a combination of pure AP linear motion and rotation of the femur relative to the tibia.

A third method utilized to analyze the relative motion of the knee joint pursuant to the instant disclosure included tracking the paths of specific contact areas on the distal and posterior anatomy of the femur on the tibia (see FIGS. 16A, 16B, 17A, 17B). Like the second method, this third method measured the overall posterior femoral rollback from fluoroscopic images of normal knee joints taken through a range of motion by projecting the lowest point of the femoral condyles on the tibial condyles and then determined the motion of the femur with respect to the tibia by tracking the path of the femoral condyles on the tibial condyles. However in this method the morphology of the femoral condyles and tibial plateaus were never studied properly with kinematics. The posterior femoral rollback is a more complicated process which soft tissues play a significant part.

Using the 3D-to-2D registration method described previously with respect to the first method, the 3D patient bone models were overlaid onto the fluoroscopic images. Relative rotations of the femur to the tibia were calculated at every 20 degrees of flexion using the 3D motion captured. In addition, at least one of computed tomography (CT) scans and magnetic resonance imaging (MRI) scans were obtained for each knee joint having been the subject of the fluoroscopic images. From the CT and/or MIR scans, the origin and insertion points were marked on the femur, fibula, and tibia models for the Anterior Cruciate Ligament (ACL), Posterior Cruciate Ligament (PCL), Medial Collateral Ligament (MCL) and Lateral Collateral Ligament (LCL). Using the rotational matrices methods previously described, the origin and insertion points were calculated and tracked during the motion (see FIG. 12). Finally, a 3D dimensional surface model of the ACL and PCL was fit to the origin and insertion points on the femur, tibia, and fibula (see FIG. 13) for each discrete point along the range of motion corresponding to the fluoroscopic images. Thereafter, an algorithm was utilized to calculate the ligament lengths across the entire range of motion (see FIGS. 14 and 15).

As evidenced in FIGS. 14 and 15, the ACL ligament had a calculated a maximum length of 37.7±4.8 mm at maximum extension of the knee while the PCL ligament had a calculated maximum length of 44.586±3.7 mm at maximum flexion of the knee. In summary, the ACL and PCL tend to act in opposite directions because as one ligament elongates the other ligament retracts.

After including the soft tissues (ACL/PCL, MCL/LCL) and morphology of the knee, it was observed that the motion of lateral femoral condyle does not just continuously rollback. In order to understand this motion, the four contact areas A1, A2, A3 and A4 depicted in FIGS. 16A-17B were examined. From this examination, a number of questions were raised. First, among these questions, was how could lateral condyle motion be continuous when the lateral condyle has almost no curvature. The lateral femoral condyle is longer in length than the lateral tibial condyle and yet the lateral femoral condyle stays in contact on the tibial plateau. Essentially, it was observed that the motion of lateral condyle behaves like a cam.

Referring to FIGS. 16A-17B, by examining the morphology of the medial and lateral tibial condyles, it is clear that after 40 degrees of flexion the PCL gets engaged (pulling) and forces some rotational motion that results in anterior femoral medial condyle movement while slightly rotating at 40 degrees (see FIG. 16, area A1). After 40 degrees of flexion, specifically around 60 degrees, the lateral femoral condyle contact area A4 experiences maximum posterior femoral rollback. Similarly, the medial condyle contact area A3 experiences maximum posterior motion. After 60 degrees, the motion of lateral femoral condyle continues until the posterior lateral femoral condyle curvature matches the proper lateral tibial curvature. In summary the medial and lateral condyle contact areas (A1/A2 and A3/A4) motion is divided in two distinct patterns of movement governed by the cam motion of the lateral condyle.

No currently available TKA consistently reproduces the kinematic pattern observed in the normal knee. Along with the inability to provide native kinematics, most patients having TKA fail to achieve full function when compared with a sex and age matched group. More importantly, weight bearing knee flexion is significantly reduced compared with passive flexion and only a small subset of patients undergoing TKA obtain more than 120 degrees flexion in weight bearing deep knee bend. Part of the reasons of the failure of the current implants to reproduce normal kinematic patterns is the absence of evaluating: (1) the relationships between underlying joint deformity and preoperative alignment in vivo joint kinematics, and (2) the relationships between rotational deformity and the subsequent effect on the in vivo joint. Furthermore, there is an absence of evaluating the effect of standard surgical techniques (e.g., gap balance) on joint kinematics. Thus, there is a need in the art for surgical solutions as part of TKA to consistently approach the kinematics of a natural knee.

It is a first aspect of the present invention to provide a tibial component placement guide for use in a knee arthroplasty procedure involving a knee joint comprising a tibia, a patella, and a femur, the guide comprising an overlay configured to be overlaid a resected tibia, the overlay including at least one of an indicia and an opening indicative of at least one of an orientation and a position of at least one of a first axis of the femur, a second axis of the femur, and a first axis of the patella.

In a more detailed embodiment of the first aspect, the overlay includes an opening indicative of the orientation of the first axis of the femur and the second axis of the femur. In yet another more detailed embodiment, the opening comprises a through hole. In a further detailed embodiment, the through hole outlines a T-shape, a horizontal aspect of the T-shape is indicative of orientation of the first axis of the femur, and a vertical aspect of the T-shape is indicative of orientation of the second axis of the femur. In still a further detailed embodiment, the through hole outlines a + shape, a horizontal aspect of the + shape is indicative of orientation of the first axis of the femur, and a vertical aspect of the + shape is indicative of orientation of the second axis of the femur. In a more detailed embodiment, the opening comprises a first through hole and a second through hole, the first through hole is indicative of the first axis of the femur, and the second through hole is indicative of orientation of the second axis of the femur. In a more detailed embodiment, the opening comprises a first cutout and a second cutout, the first cutout is indicative of the first axis of the femur, and the second cutout is indicative of orientation of the second axis of the femur. In another more detailed embodiment, the first axis of the femur comprises the posterior condylar axis of the femur. In yet another more detailed embodiment, the second axis of the femur comprises the helical axis of the femur. In still another more detailed embodiment, the overlay has a contour outline that is aligned with the resected tibia.

In yet another more detailed embodiment of the first aspect, the contour outline is patient-specific. In yet another more detailed embodiment, the tibial component placement guide further includes at least one of an indicia and an opening indicative of at least two of a medial guide, a lateral guide, a size of the guide, and a particular patient. In a further detailed embodiment, the guide is fabricated from at least one of titanium, a titanium alloy, stainless steel, and a stainless steel alloy. In still a further detailed embodiment, the guide includes a through aperture configured to align a through fastener mounted to the resected tibia. In a more detailed embodiment, the through fastener comprises a pin. In a more detailed embodiment, the through aperture comprises a plurality of through apertures, and each of the plurality of apertures is configured to receive a pin. In another more detailed embodiment, the overlay comprises a base plate. In yet another more detailed embodiment, he base plate includes a flange along a periphery of the base plate. In still another more detailed embodiment, the tibial component placement guide further includes at least one of an indicia and an opening indicative of the orientation of a third axis of the femur, the third axis being parallel to the first axis.

It is a second aspect of the present invention to provide a method of using a tibial component placement guide for use in a knee arthroplasty procedure involving a knee joint comprising a tibia, a patella, and a femur, the method comprising: (a) applying an overlay to a resected tibia, the overlay including at least one of an indicia and an opening indicative of at least one of an orientation and a position of at least one of a first axis of the femur, a second axis of the femur, and a first axis of the patella; (b) marking the resected tibia with at least one mark using the overlay to denote at least one of an orientation and a position of at least one of a first axis of the femur, a second axis of the femur, and a first axis of the patella; and, (c) orienting and attaching at least one of an orthopedic tibial tray trial and an orthopedic tibial tray to the resected tibia using the mark.

In a more detailed embodiment of the second aspect, the step of applying the overlay includes aligning a peripheral shape of the overlay with a peripheral shape of the resected tibia and placing the overlay on top of the resected tibia. In yet another more detailed embodiment, the overlay includes an opening indicative of the orientation of the first axis of the femur and the second axis of the femur. In a further detailed embodiment, the opening comprises a through hole. In still a further detailed embodiment, the through hole outlines a T-shape, a horizontal aspect of the T-shape is indicative of orientation of the first axis of the femur, and a vertical aspect of the T-shape is indicative of orientation of the second axis of the femur. In a more detailed embodiment, the through hole outlines a + shape, a horizontal aspect of the + shape is indicative of orientation of the first axis of the femur, and a vertical aspect of the + shape is indicative of orientation of the second axis of the femur. In a more detailed embodiment, the opening comprises a first through hole and a second through hole, the first through hole is indicative of the first axis of the femur, and the second through hole is indicative of orientation of the second axis of the femur. In another more detailed embodiment, the opening comprises a first cutout and a second cutout, the first cutout is indicative of the first axis of the femur, and the second cutout is indicative of orientation of the second axis of the femur. In yet another more detailed embodiment, the first axis of the femur comprises the posterior condylar axis of the femur. In still another more detailed embodiment, the second axis of the femur comprises the helical axis of the femur.

In yet another more detailed embodiment of the second aspect, the overlay has a contour outline that is aligned with the resected tibia. In yet another more detailed embodiment, the contour outline is patient-specific. In a further detailed embodiment, the overlay further includes at least one of an indicia and an opening indicative of at least two of a medial guide, a lateral guide, a size of the guide, and a particular patient. In still a further detailed embodiment, the guide is fabricated from at least one of titanium, a titanium alloy, stainless steel, and a stainless steel alloy. In a more detailed embodiment, the guide includes a through aperture configured to align a through fastener mounted to the resected tibia. In a more detailed embodiment, the through fastener comprises a pin. In another more detailed embodiment, the through aperture comprises a plurality of through apertures, and each of the plurality of apertures is configured to receive a pin. In yet another more detailed embodiment, the overlay comprises a base plate. In still another more detailed embodiment, the base plate includes a flange along a periphery of the base plate.

In a more detailed embodiment of the second aspect, the overlay further comprises at least one of an indicia and an opening indicative of the orientation of a third axis of the femur, the third axis being parallel to the first axis. In yet another more detailed embodiment, the at least one mark comprises a pin, and the step of marking the resected tibia includes fastening the at least one pin to the resected tibia. In a further detailed embodiment, the at least one mark comprises an indentation formed into the resected tibia, and the step of marking the resected tibia includes using a punch to form the indentation into the resected tibia. In still a further detailed embodiment, the at least one mark comprises a representation formed into the resected tibia, and the step of marking the resected tibia includes writing the representation onto the resected tibia. In a more detailed embodiment, the orienting and attaching step includes orienting and attaching an orthopedic tibial tray to the resected tibia using the mark. In a more detailed embodiment, the method further includes removing the overlay prior to orienting and attaching at least one of the orthopedic tibial tray trial and the orthopedic tibial tray to the resected tibia using the mark. In another more detailed embodiment, the overlay includes an opening indicative of the orientation of the first axis of the patella. In yet another more detailed embodiment, the opening comprises a through hole.

It is a third aspect of the present invention to provide a method of fabricating a tibial component placement guide for use in a knee arthroplasty procedure involving a knee joint comprising a tibia, a patella, and a femur, the method comprising generating a tibial component placement guide that typifies at least one of a shape and an outline of a resected tibia, along with at least one identifier representative of at least one of a position and an orientation of a kinematic axis of at least one of the femur and the patella.

In a more detailed embodiment of the third aspect, the tibial component guide typifies at least one of the shape of the resected tibia, and the tibial component guide is mass-customized. In yet another more detailed embodiment, the tibial component guide typifies at least one of the outline of the resected tibia, and the tibial component guide is mass-customized. In a further detailed embodiment, the tibial component guide typifies at least one of the shape of the resected tibia, and the tibial component guide is patient-specific. In still a further detailed embodiment, the tibial component guide typifies at least one of the outline of the resected tibia, and the tibial component guide is patient-specific. In a more detailed embodiment, the at least one identifier is representative of an orientation of the kinematic axis of the femur, and the kinematic axis comprises a femoral post condylar axis. In a more detailed embodiment, the at least one identifier is oriented parallel to the femoral post condylar axis. In another more detailed embodiment, the at least one identifier is representative of a position of the kinematic axis of the femur, and the kinematic axis comprises a femoral helical axis. In yet another more detailed embodiment, the position of the at least one identifier is representative of a projected position of the femoral helical axis onto the resected tibia. In still another more detailed embodiment, the at least one identifier is representative of the position of the kinematic axis of the patella, and the kinematic axis comprises a patella transverse axis.

In yet another more detailed embodiment of the third aspect, the at least one identifier is representative of the orientation of the kinematic axis of the patella, and the kinematic axis comprises a patella transverse axis. In yet another more detailed embodiment, the at least one identifier is representative of a position of the kinematic axis of the femur, and the kinematic axis of the femur is parallel to the sagittal kinematic plane of the femur. In a further detailed embodiment, the position of the at least one identifier is representative of a projected position of the sagittal kinematic plane onto the resected tibia. In still a further detailed embodiment, the method further includes establishing at least one of the shape and the outline of the resected tibia. In a more detailed embodiment, the step of establishing at least one of the shape and the outline of the resected tibia includes performing a virtual resection upon a tibial bone model to generate a virtual resected tibia. In a more detailed embodiment, the virtual resected tibia is analyzed to generate a two dimensional shape of a virtual resected surface, and the two dimensional shape of the virtual resected surface typifies the shape of the resected tibia. In another more detailed embodiment, the virtual resected tibia is analyzed to generate a two dimensional outline of a virtual resected surface, and the two dimensional outline of the virtual resected surface typifies the outline of the resected tibia. In yet another more detailed embodiment, the method further includes establishing at least one of the position and the orientation of the kinematic axis of at least one of the femur and the patella when superimposed onto the tibia. In still another more detailed embodiment, the kinematic axis comprises at least one of a femoral helical axis, a femoral post condylar axis, a patella transverse axis, a femoral sagittal kinematic plane, and a patella sagittal kinematic plane.

In a more detailed embodiment of the third aspect, the step of establishing at least one of the position and the orientation of the kinematic axis when superimposed onto the tibia includes at least one of establishing a femoral helical axis with respect to the femur, establishing a femoral post condylar axis with respect to the femur, establishing a patella transverse axis with respect to the patella, establishing a femoral sagittal kinematic plane with respect to the femur, and establishing a patella sagittal kinematic plane with respect to the patella. In yet another more detailed embodiment, the step of establishing at least one of the position and the orientation of the kinematic axis when superimposed onto the tibia includes establishing the femoral helical axis with respect to the femur, and the step of establishing the femoral helical axis with respect to the femur comprises analyzing the relative motion of the femur with respect to the tibia. In a further detailed embodiment, the step of analyzing the relative motion of the femur with respect to the tibia includes analyzing tracked contact points between the tibia and the femur using fluoroscopy. In still a further detailed embodiment, the step of analyzing the relative motion of the femur with respect to the tibia includes analyzing tracked contact paths of the femur with respect to the tibia using fluoroscopy. In a more detailed embodiment, the step of establishing at least one of the position and the orientation of the kinematic axis when superimposed onto the tibia includes establishing the femoral post condylar axis with respect to the femur, and the step of establishing the femoral post condylar axis with respect to the femur comprises analyzing the relative motion of the femur with respect to the tibia. In a more detailed embodiment, the step of analyzing the relative motion of the femur with respect to the tibia includes analyzing tracked contact points between the tibia and the femur using fluoroscopy. In another more detailed embodiment, the step of analyzing the relative motion of the femur with respect to the tibia includes analyzing tracked contact paths of the femur with respect to the tibia using fluoroscopy.

In a more detailed embodiment of the third aspect, the step of establishing at least one of the position and the orientation of the kinematic axis when superimposed onto the tibia includes establishing the femoral sagittal kinematic plane with respect to the femur, and the step of establishing the femoral sagittal kinematic plane with respect to the femur comprises analyzing the relative motion of the femur with respect to the tibia. In yet another more detailed embodiment, the step of analyzing the relative motion of the femur with respect to the tibia includes analyzing tracked contact points between the tibia and the femur using fluoroscopy. In a further detailed embodiment, the step of analyzing the relative motion of the femur with respect to the tibia includes analyzing tracked contact paths of the femur with respect to the tibia using fluoroscopy. In still a further detailed embodiment, the step of establishing at least one of the position and the orientation of the kinematic axis when superimposed onto the tibia includes establishing the patella transverse axis with respect to the patella, and the step of establishing the patella transverse axis with respect to the patella comprises analyzing the relative motion of the patella with respect to the femur. In a more detailed embodiment, the step of analyzing the relative motion of the patella with respect to the femur includes analyzing tracked contact points between the patella and the femur using fluoroscopy. In a more detailed embodiment, the step of analyzing the relative motion of the patella with respect to the femur includes analyzing tracked contact paths of the patella with respect to the femur using fluoroscopy. In another more detailed embodiment, the step of establishing at least one of the position and the orientation of the kinematic axis when superimposed onto the tibia includes establishing the patella sagittal kinematic plane with respect to the patella, and the step of establishing the patella sagittal kinematic plane with respect to the patella comprises analyzing the relative motion of the patella with respect to the femur.

In yet another more detailed embodiment of the third aspect, the step of analyzing the relative motion of the patella with respect to the femur includes analyzing tracked contact points between the patella and the femur using fluoroscopy. In yet another more detailed embodiment, the step of analyzing the relative motion of the patella with respect to the femur includes analyzing tracked contact paths of the patella with respect to the femur using fluoroscopy. In a further detailed embodiment, the tibial component placement guide includes an opening indicative of the orientation of the first axis of the femur and the second axis of the femur. In still a further detailed embodiment, the opening comprises a through hole. In a more detailed embodiment, the through hole outlines a T-shape, a horizontal aspect of the T-shape is indicative of orientation of the first axis of the femur, and a vertical aspect of the T-shape is indicative of orientation of the second axis of the femur. In a more detailed embodiment, the through hole outlines a + shape, a horizontal aspect of the + shape is indicative of orientation of the first axis of the femur, and a vertical aspect of the + shape is indicative of orientation of the second axis of the femur. In another more detailed embodiment, the opening comprises a first through hole and a second through hole, the first through hole is indicative of the first axis of the femur, and the second through hole is indicative of orientation of the second axis of the femur. In yet another more detailed embodiment, the opening comprises a first cutout and a second cutout, the first cutout is indicative of the first axis of the femur, and the second cutout is indicative of orientation of the second axis of the femur. In still another more detailed embodiment, the first axis of the femur comprises the posterior condylar axis of the femur.

In a more detailed embodiment of the third aspect, the second axis of the femur comprises the helical axis of the femur. In yet another more detailed embodiment, the tibial component placement guide has a contour outline that is aligned with the resected tibia. In a further detailed embodiment, the contour outline is patient-specific. In still a further detailed embodiment, the guide further includes at least one of an indicia and an opening indicative of at least two of a medial guide, a lateral guide, a size of the guide, and a particular patient. In a more detailed embodiment, the guide is fabricated from at least one of titanium, a titanium alloy, stainless steel, and a stainless steel alloy. In a more detailed embodiment, the guide includes a through aperture configured to align a through fastener mounted to the resected tibia. In another more detailed embodiment, the through fastener comprises a pin.

In a more detailed embodiment of the third aspect, the through aperture comprises a plurality of through apertures, and each of the plurality of apertures is configured to receive a pin. In yet another more detailed embodiment, the tibial component placement guide comprises a base plate. In a further detailed embodiment, the base plate includes a flange along a periphery of the base plate. In still a further detailed embodiment, the tibial component placement guide further comprises at least one of an indicia and an opening indicative of the orientation of a third axis of the femur, the third axis being parallel to the first axis. In a more detailed embodiment, the at least one mark comprises a pin, and the step of marking the resected tibia includes fastening the at least one pin to the resected tibia. In a more detailed embodiment, the at least one mark comprises an indentation formed into the resected tibia, and the step of marking the resected tibia includes using a punch to form the indentation into the resected tibia.

In a more detailed embodiment of the third aspect, the at least one mark comprises a representation formed into the resected tibia, and the step of marking the resected tibia includes writing the representation onto the resected tibia. In yet another more detailed embodiment, the orienting and attaching step includes orienting and attaching an orthopedic tibial tray to the resected tibia using the mark. In a further detailed embodiment, the method further includes removing the tibial component placement guide prior to orienting and attaching at least one of the orthopedic tibial tray trial and the orthopedic tibial tray to the resected tibia using the mark.

It is a fourth aspect of the present invention to provide a kinematic femoral component for use in a knee arthroplasty procedure involving a knee joint comprising a tibia, a patella, and a femur, the kinematic femoral component comprising a femoral component replicating a natural trochlear groove angle of a femur that is parallel to a sagittal femoral kinematic plane.

In a more detailed embodiment of the fourth aspect, a lateral aspect of an anterior flange extends proximally, the respect to a femur, between 10 to 45 millimeters beyond a femoral knee center of the femur. In yet another more detailed embodiment, a lateral aspect of an anterior flange extends proximally, the respect to a femur, between 10 to 25 millimeters beyond a femoral knee center of the femur.

BRIEF DESCRIPTION OF THE DRAWINGS

FIGS. 38A-38C are graphical depictions of motion of the patella before and after TKA and showing that post TKA the patella no longer replicates its natural kinematic motion.

FIG. 93 is a picture of a distal tibia showing the location of the ankle center.

FIGS. 94A-94D are pictures of various distal femurs showing the location of the meniscal axis.

DETAILED DESCRIPTION

Figures 1A, 1B, 1C:
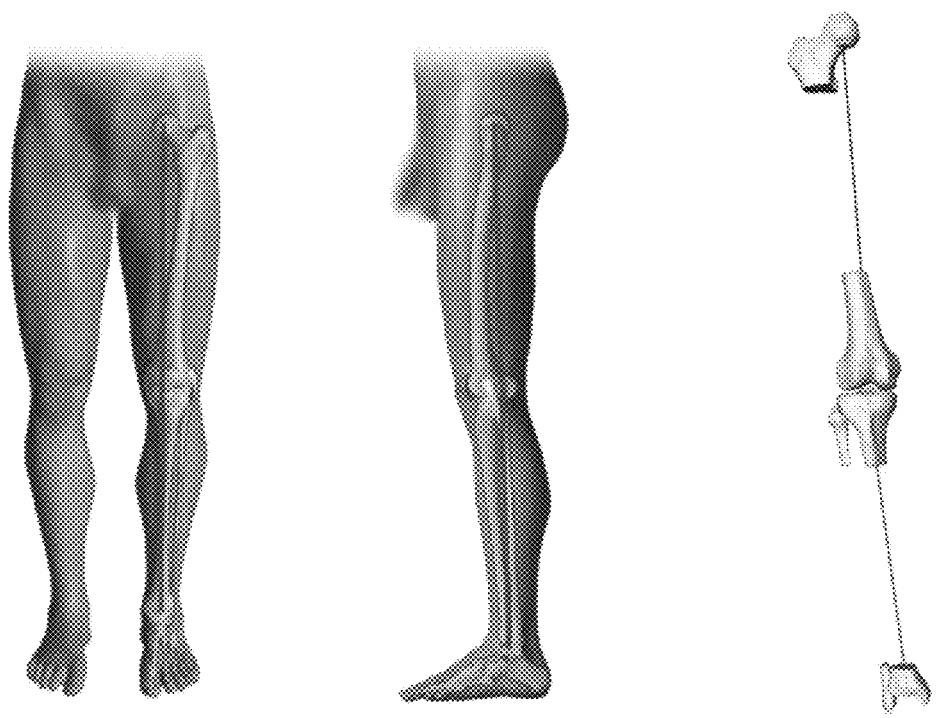
FIGS. 1A-1C are anatomical frontal, anatomical profile, and skeletal section views depicting the femoral and tibial mechanical axis.
Figure 2A:
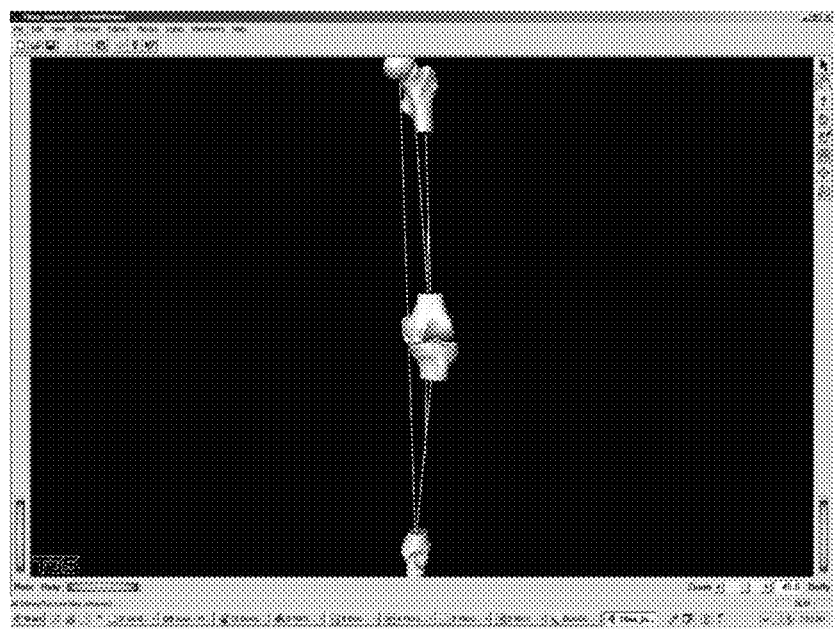
FIG. 2A is a software user interface of an exemplary software system in accordance with the instant disclosure showing hip, knee, and ankle (HKA) axes.
Figure 2B:
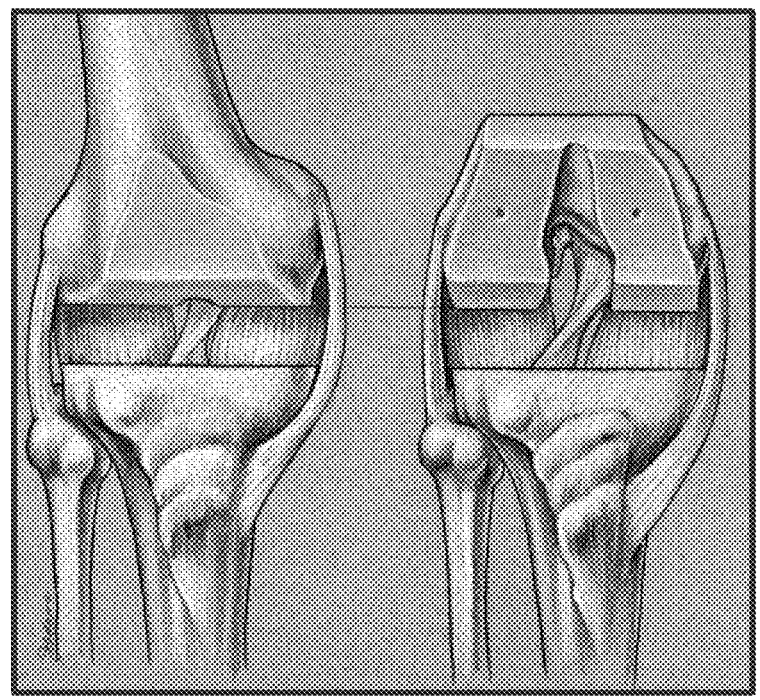
FIG. 2B is a graphical depiction of a gap balance technique used during a knee arthroplasty procedure.
Figures 3A, 3B:
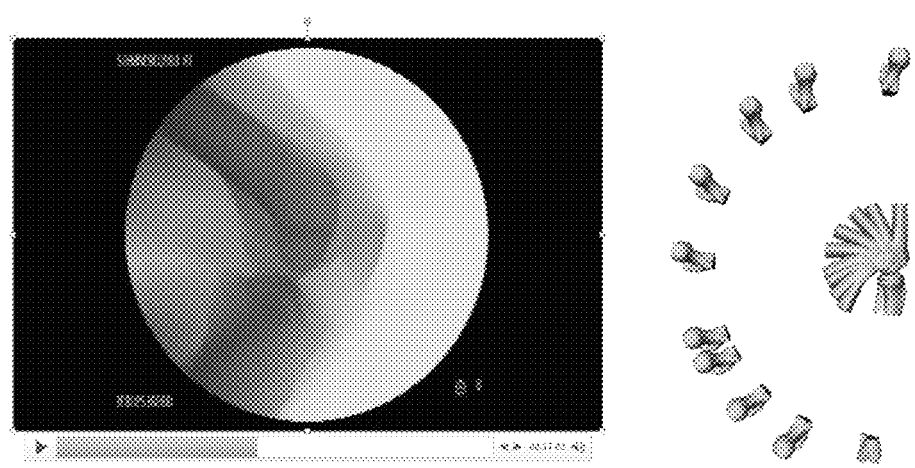
FIGS. 3A and 3B are X-ray fluoroscopic images of a knee joint bent approximately 90 degrees, as well as a compilation image showing the position of the femoral head and femoral condyles across a range of motion.
Figures 4A, 4B, 4C, 4D:
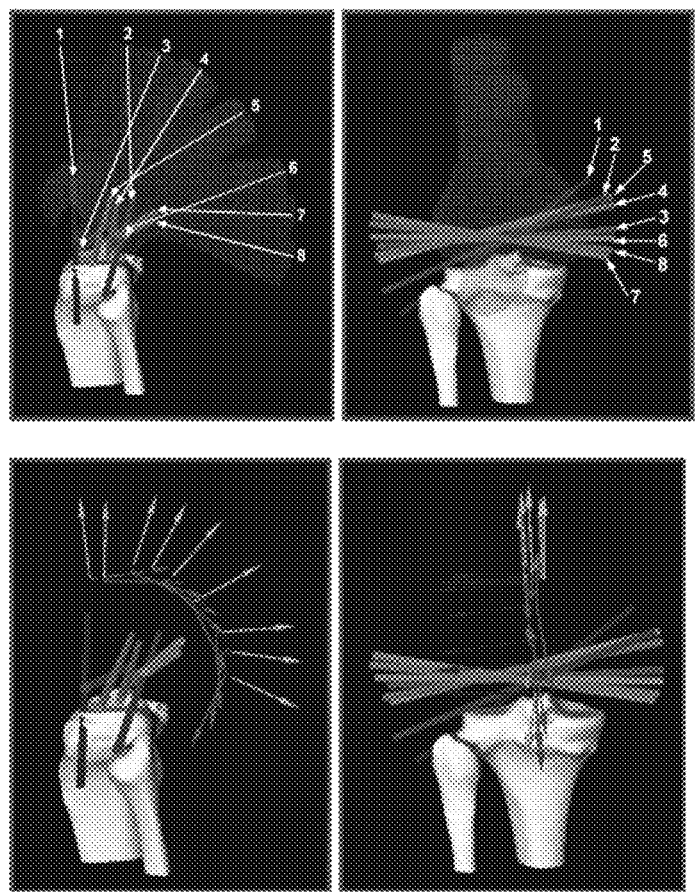
FIGS. 4A-4D are helical axes of motion corresponding to nine steps of knee flexion from 0 to 120 degrees, shown in an sagittal plane, an anteroposterior view of axes projected on the frontal plane. The geometrical center of the femur rotating around the screw/helical axis shown in a sagittal and an anteroposterior view of the geometrical centers of the femur projected on the frontal plane.
Figures 5A, 5B, 5C, 5D:
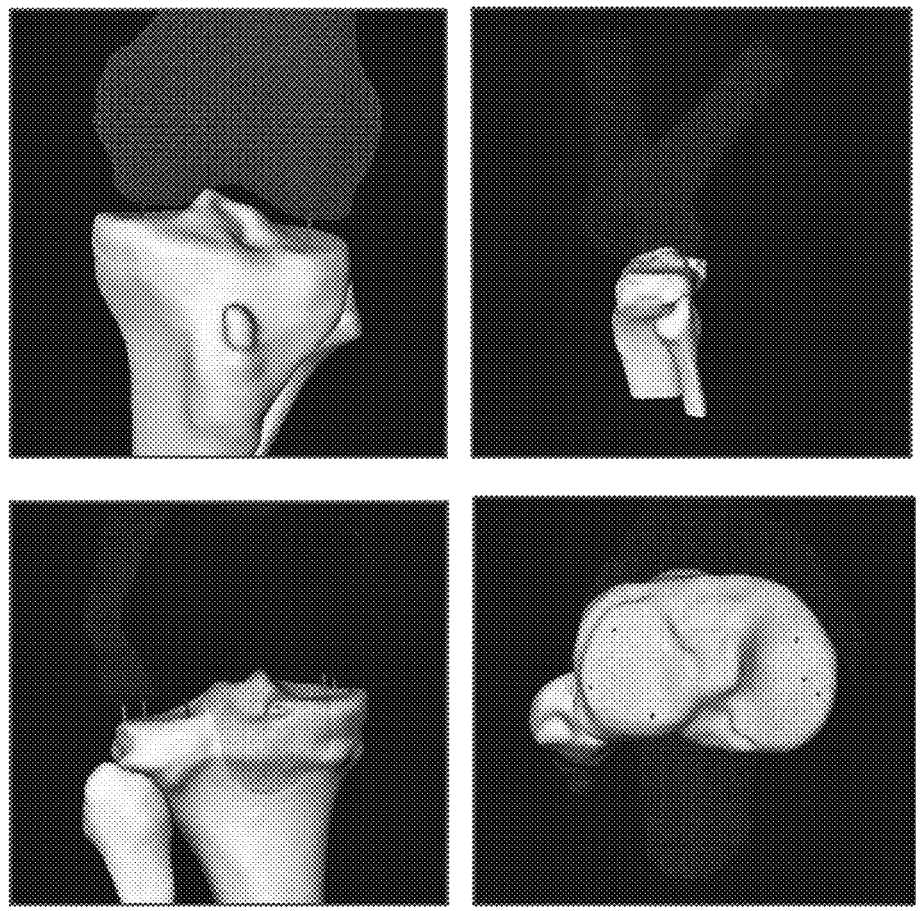
FIGS. 5A-5D include a frontal view of the knee joint showing the minimum points on the femoral condyles projected on the tibial plateau. A sagittal view of the knee joint showing 3 flexion angles and their corresponding lowest points projected on the tibial plateau. An anteroposterior view of the knee joint showing the three lowest points on the femur projected on the frontal plane. An axial view of the minimum points projected on the tibial plateau. Finally, a top view of the tibial plateau showing a plane going through the geometrical center of the tibia of knee joint.
Figure 6:
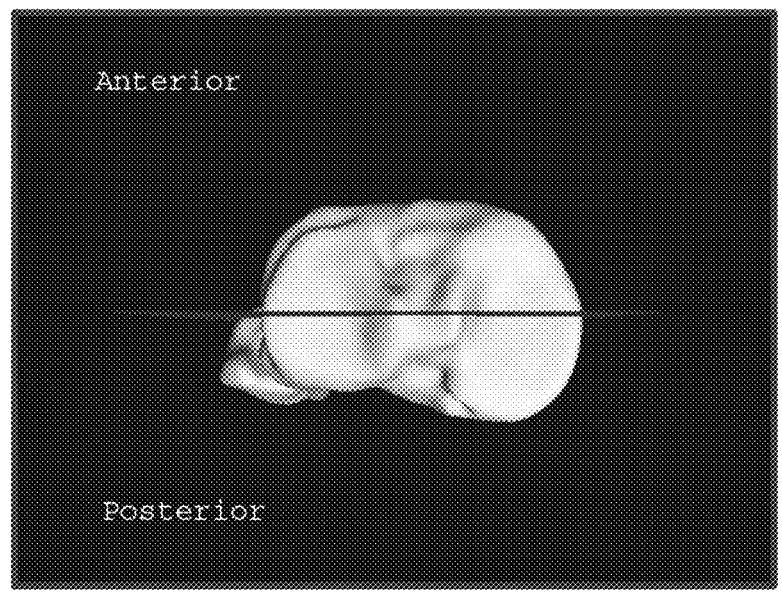
FIG. 6 is a top view of the tibial plateau showing a plane going through the geometrical center of the tibia of knee joint.
Figure 7:
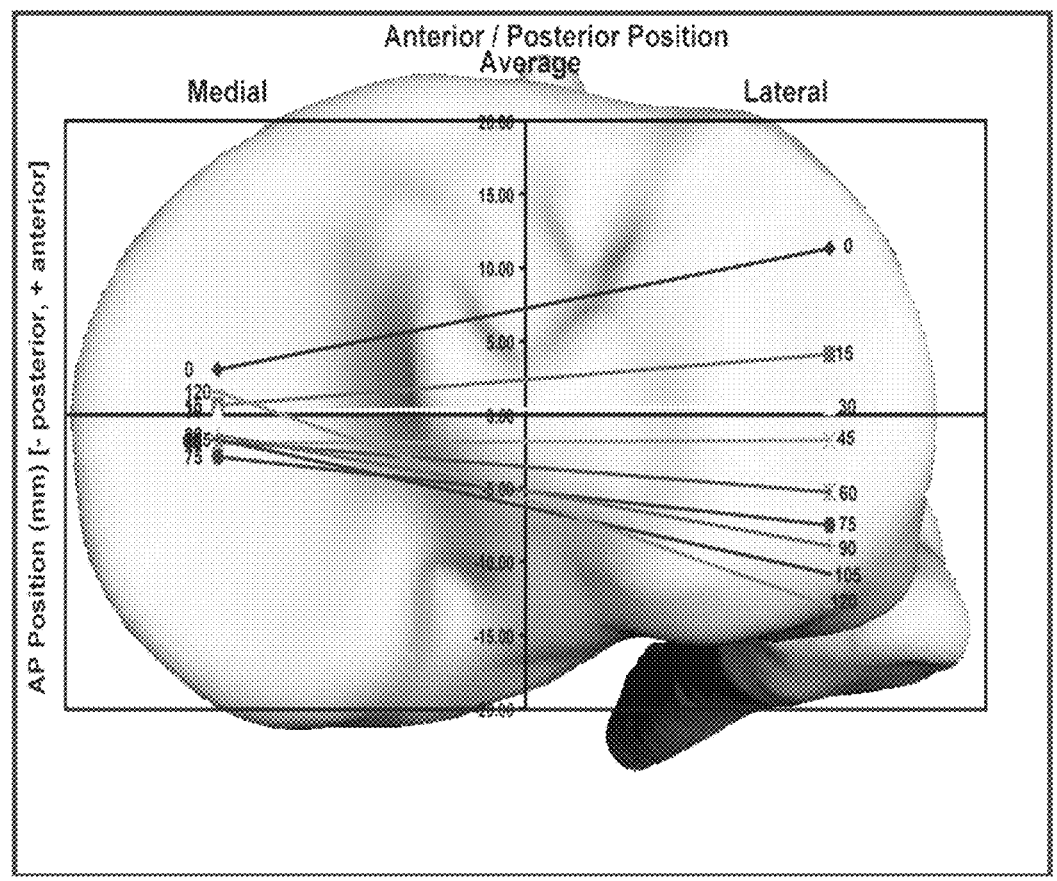
FIG. 7 is a graphical representation of the top of a tibia and the average normal subjects' medial and lateral condyle contact positions during a deep knee bend activity.
Figure 8:
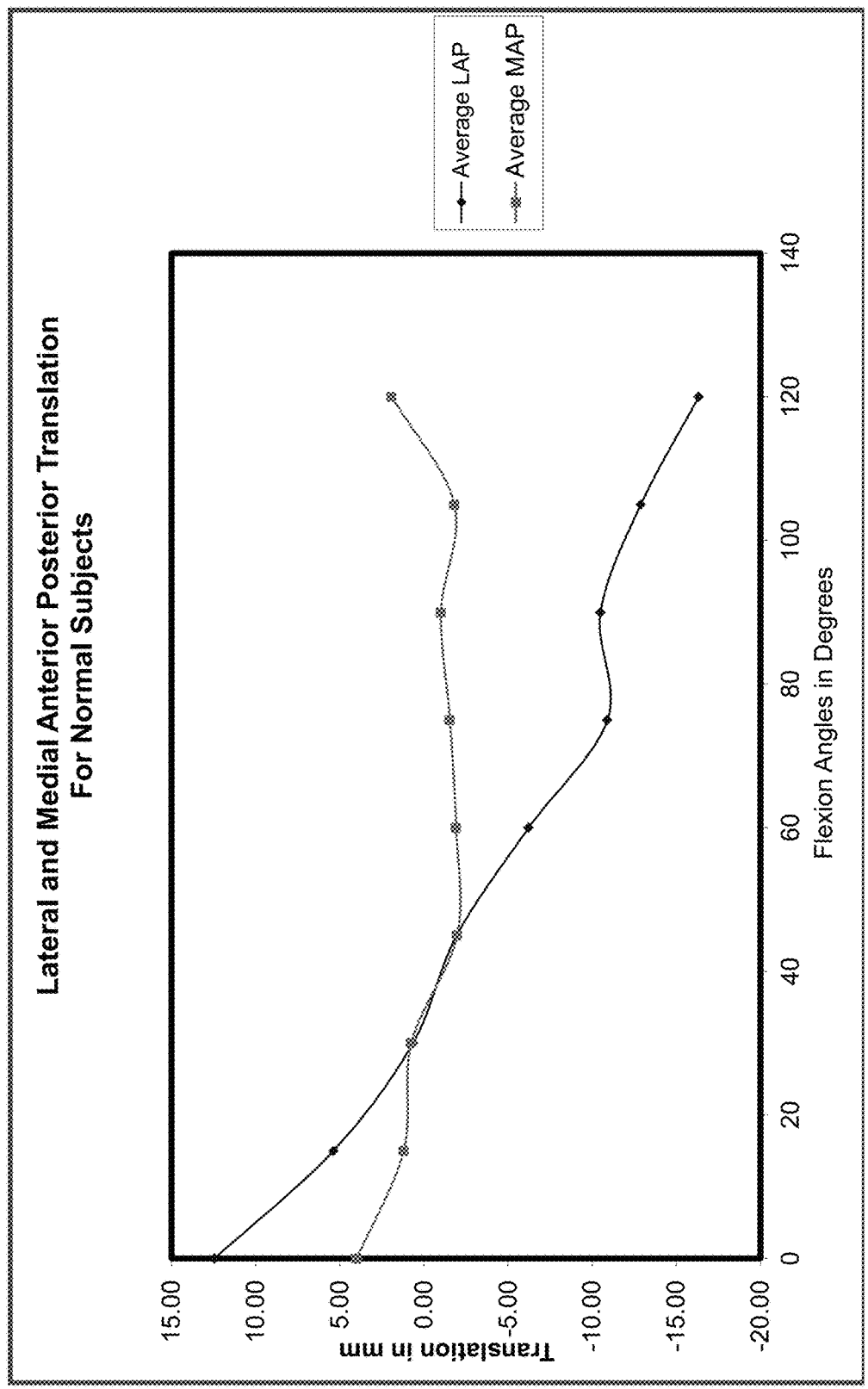
FIG. 8 is a plot of anteroposterior translations of the contact points between the femur and the tibia during knee flexion.
Figure 9:
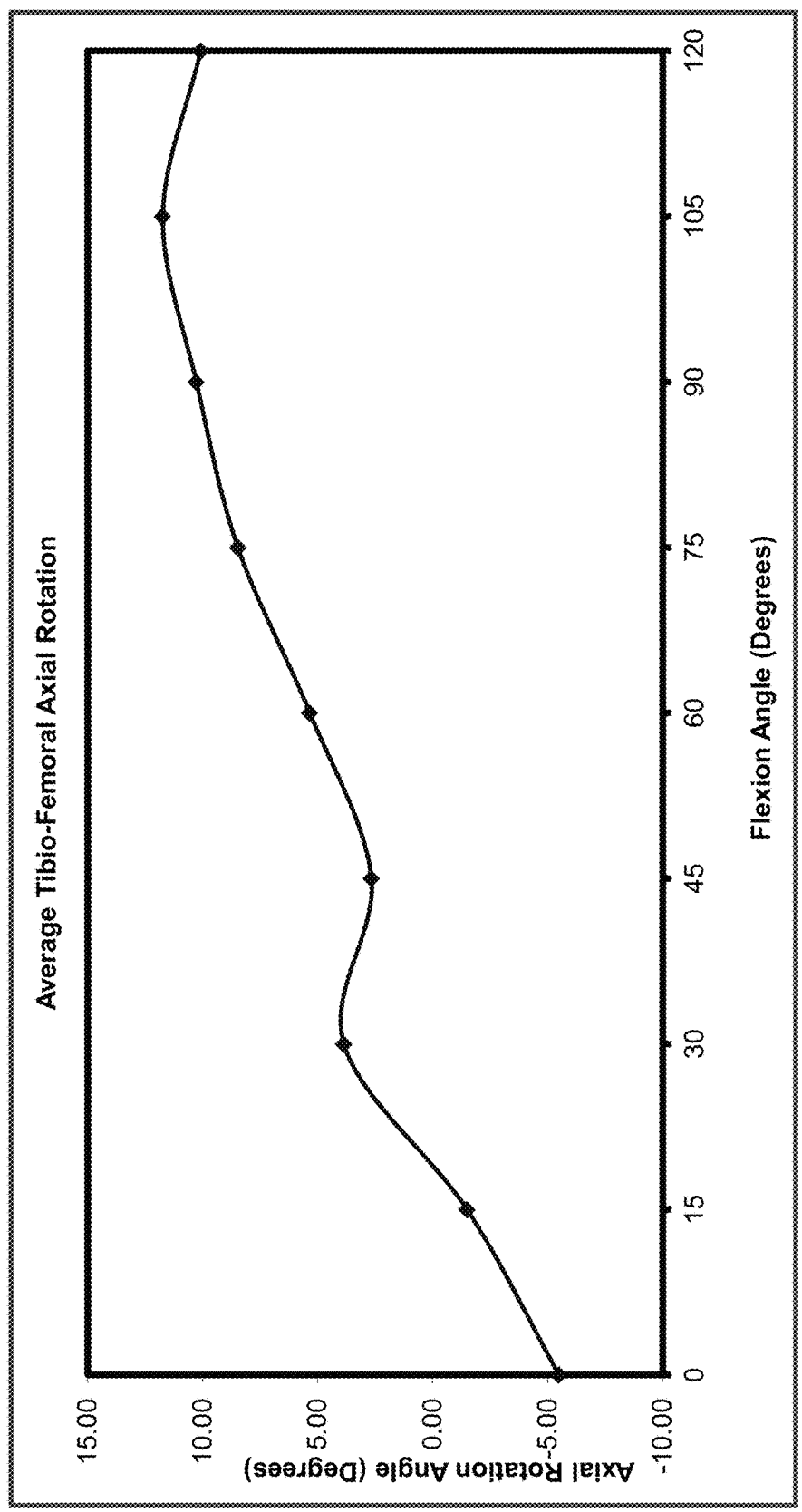
FIG. 9 is a plot of axial rotation of the femur during knee flexion for normal subjects.
Figures 10A, 10B, 10C, 10D, 10E:
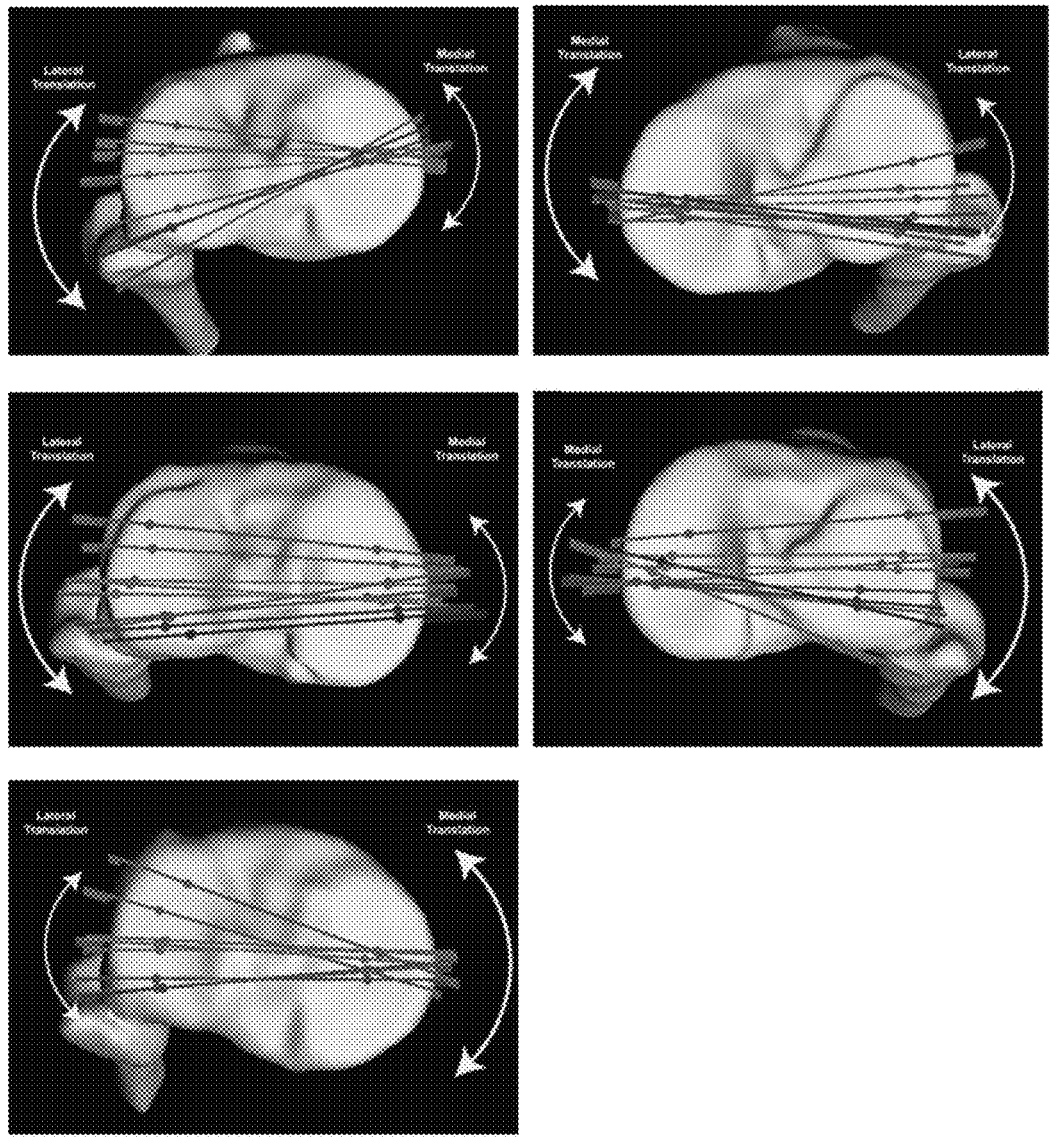
FIGS. 10A-10E are axial, top views of the minimum points projected on the tibial plateau of five subject knees showing clear medial pivoting motion of the femur relative to the tibia.
Figures 11A, 11B, 11C, 11D:
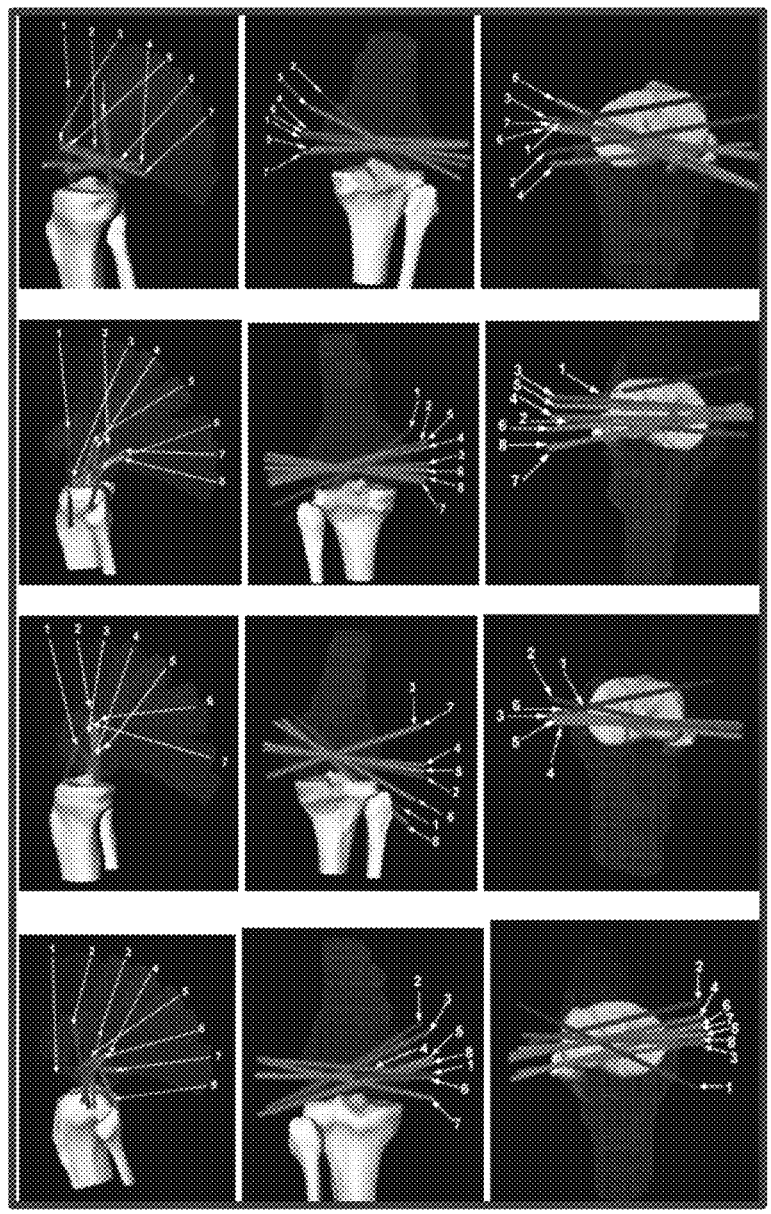
FIGS. 11A-11D depict helical axis of the normal knees showing the axis does not stay fixed in space during an entire movement through the available range of motion across four subject knees.
Figure 12:
FIG. 12 is a graphical depiction of ligament attachment sites tracked during fluoroscopy of a knee joint.
Figure 13:
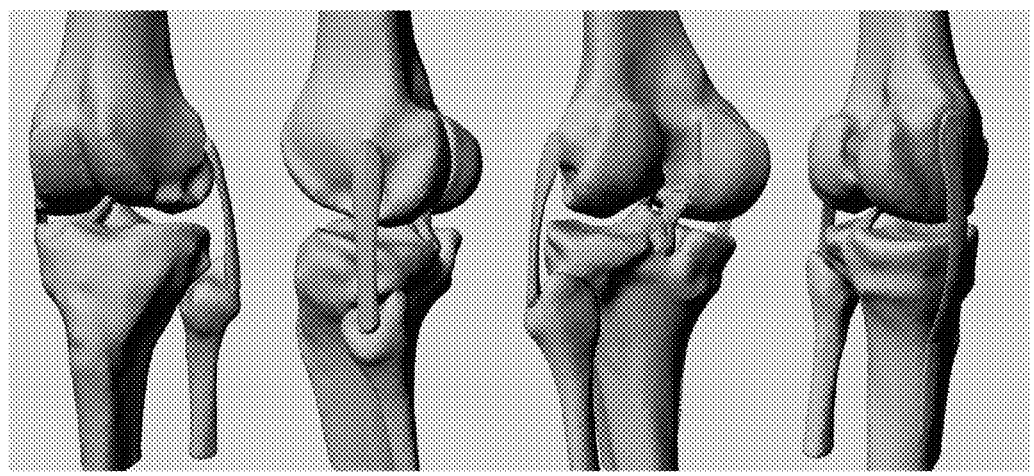
FIG. 13 is a series of views of a virtual knee joint model showing ligaments reconstructed using ligament attachment sites.
Figures 14, 15:
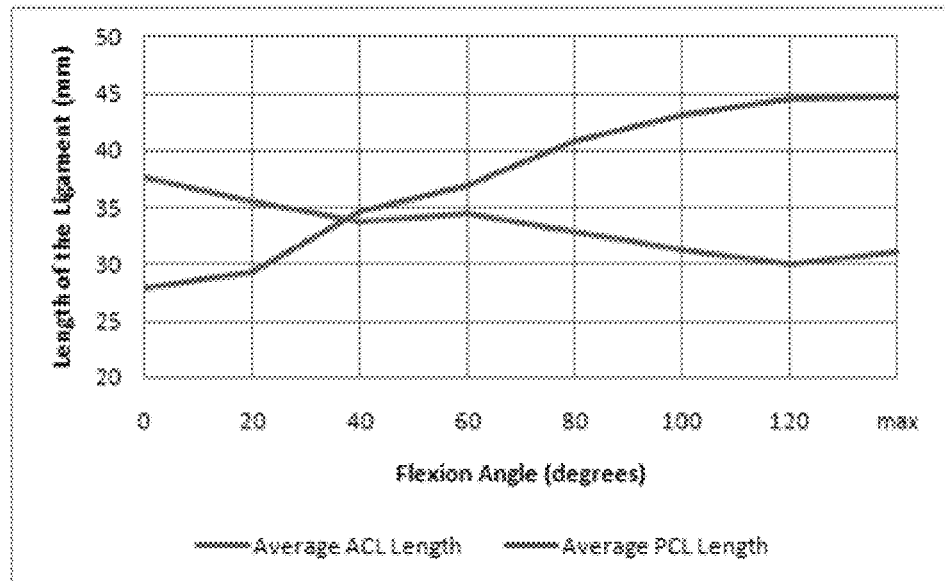
FIG. 14 is a plot depicting average lengths in millimeters for the anterior cruciate ligament and the posterior collateral ligament at each increment of flexion during a deep knee bend.
FIG. 15 is a table detailing subjects lengths in millimeters for the anterior cruciate ligament and the posterior collateral ligament at each increment of flexion during deep knee bend.
Figures 16A, 16B:
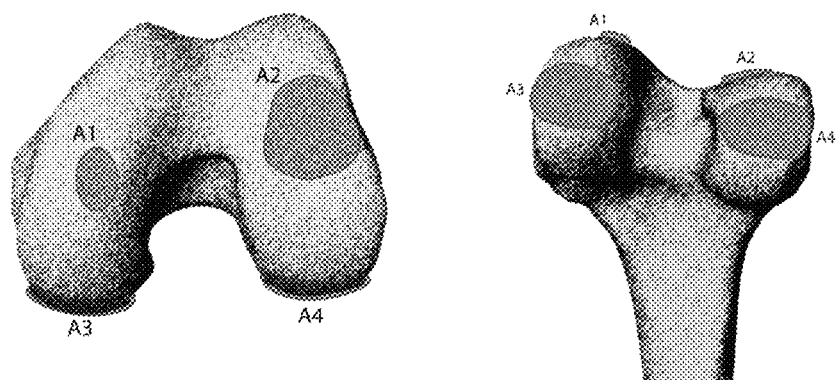
FIGS. 16A and 16B are distal and posterior views of a posterior end of a femur.
Figures 17A, 17B:
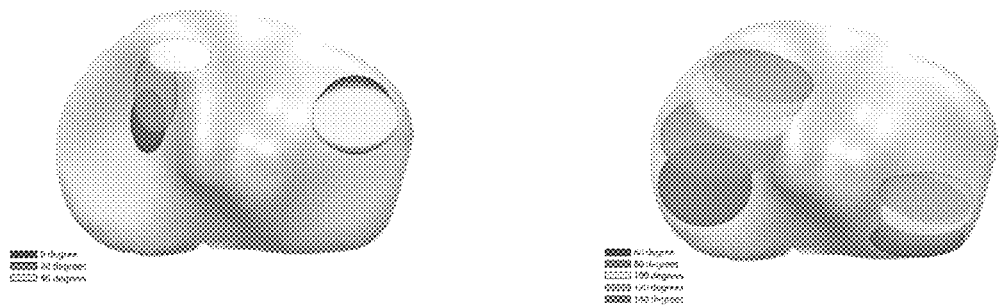
FIGS. 17A and 17B are projections of tracked areas from the femur onto the tibia from zero degrees to 140 degrees projected on the tibia left A1/A2 and right A3/A4 from FIGS. 16A, 16B.
Figures 18A, 18B, 18C, 18D:
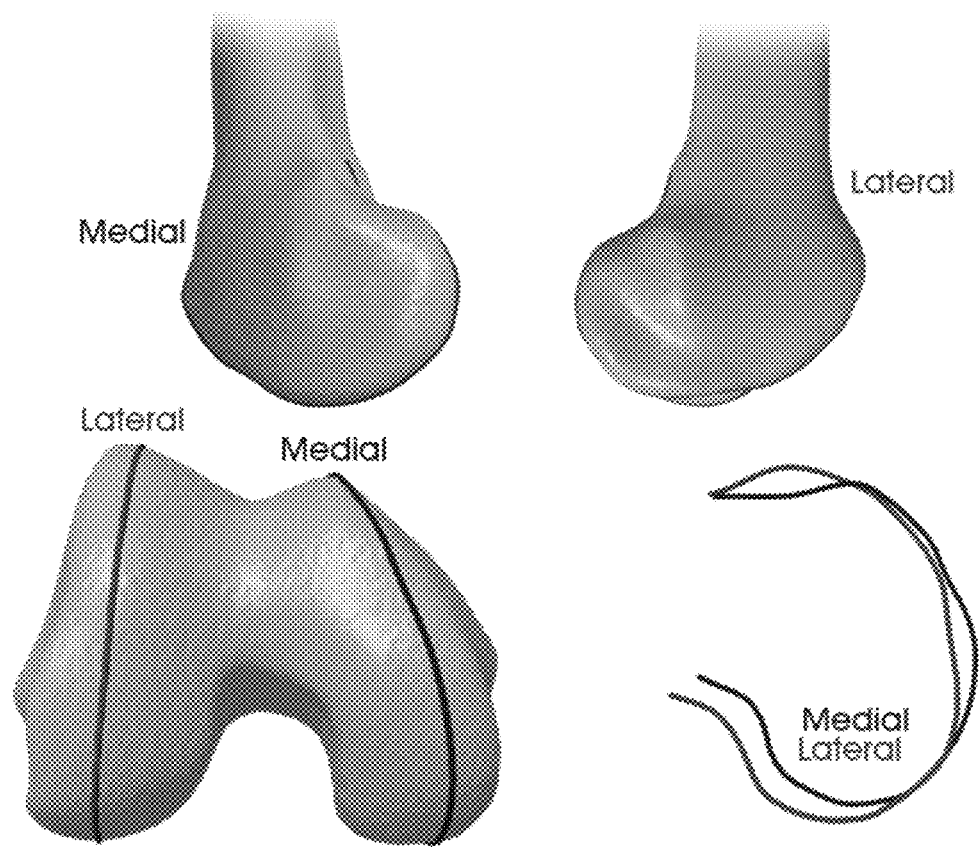
FIGS. 18A-18D include medial, lateral, and posterior views of a femur, along with associated curves depicting the curvature differences along the length of the medial and lateral condyles.

The exemplary embodiments of the present disclosure are described and illustrated below to encompass devices, methods, and techniques relating to knee arthroplasty. Of course, it will be apparent to those of ordinary skill in the art that the embodiments discussed below are exemplary in nature and may be reconfigured without departing from the scope and spirit of the present disclosure. It is also to be understood that variations of the exemplary embodiments contemplated by one of ordinary skill in the art shall concurrently comprise part of the instant disclosure. However, for clarity and precision, the exemplary embodiments as discussed below may include optional steps, methods, and features that one of ordinary skill should recognize as not being a requisite to fall within the scope of the present disclosure.

Referring to FIGS. 85-89, as used herein, the following are mechanical neutral anatomic landmark definitions for the femur: (1) Transepicondylar Axis (TEA): The axis joining the most medial prominence of the medial epicondyle and the most lateral prominence of the lateral epicondyle; (2) Posterior Condyle Axis (PCA): The axis joining the most posterior points on the medial and lateral condyles of the distal femur; (3) Distal Anatomical Axis (DAA): The distal anatomical axis is defined by locating the shaft centroids at the distal one-third and distal one-fifth of the overall femur length; (4) Central AP Axis (CAP): Axis defined with termini at the posterior aspect of the intercondylar notch and the most anterior portion of the intercondylar groove; (5) Femoral Saddle Point: A landmark located at the most distal extension of the intercondylar groove; (6) Knee Center: Using the two endpoints of the CAP measurement and the femoral saddle point, a plane is defined which bisects the femur into medial and lateral sides. The intersection of this plane with the TEA is the knee center, which forms the distal endpoint of the mechanical axis (MA) of the femur; (7) Distal Mechanical Entry Point of the Femur: The distal entry of the medullary canal. This landmark is estimated to be at the intersection of the anatomical axis of the femur with its intercondylar notch; (8) Mechanical axis (MA): Axis defined by the femoral head center and knee center; (9) AP Direction: Using the MA and the TEA, a mutually perpendicular vector with its origin at the knee center is used to define the antero-posterior (AP) direction, resulting in a direction similar to Whiteside's line; (10) Femoral AP Axis (FAA): Axis defined as the cross-product of the mechanical axis of the femur with the PCA; (11) Mediolateral Axis of the Femur (MLA): The cross-product of the femoral mechanical axis with its anteroposterior axis; (12) Femoral Head Center (FHC): Center of the sphere approximating femoral head; (13) Anterior Medio-lateral Width (AML): The AP direction is used to locate the two most anterior landmarks on the medial and lateral condyles of the distal femur. Connecting the two most anterior points gives a measurement of anterior medio-lateral width (AML) along the trochlear line; (14) Posterior Medio-lateral Width (PML): The AP direction is used to locate the two most posterior points on the medial and lateral condyles of the distal femur. Connecting the two most posterior points gives a measure of posterior medio-lateral width (PML) measured along the posterior condylar axis (PCA); (15) AP Length of Medial Condyle (MAP): Connecting the pairs of medial vertices defined above, respectively, gives the AP length of the medial condyle; (16) AP Length of Lateral Condyle (LAP): Connecting the pairs of lateral vertices defined above, respectively, gives the AP length of the lateral condyle (LAP); (17) Overall AP Length: The minimum distance between the prominences of the lateral anterior condyle and the posterior plane; (18) AP Angle: The angle of the AML vector relative to the posterior plane; (19) Distal Medial-lateral Length (DML): The most distal aspects of the medial and lateral condyles are recorded using MA as a reference direction. The distance between these two landmarks is denoted as DML; (20) Posterior Angle (PA): The angle between the vector connecting the DML length and the mean axis of the femur; (21) Condylar Twist Angle (CTA): The angle between the TEA and PCA; (22) Patellar Groove Height (GH): Calculated between the posterior aspect of the intercondylar notch and the midpoint between the two DML axis points; (23) Femoral Axis (FA): Line from the center of the femoral head to the center of the shaft at the level of the lesser trochanter. Anteversion (+) is ventral, retroversion (−) is dorsal; (24) Femoral Version: Angle comparing the femoral axis to the transepicondylar axis; (25) Femoral Shaft Curvature (SC): The radius of curvature of the femoral mean axis; (26) Femoral implant flexion/extension: Rotation about the mediolateral axis of the femur. From a lateral perspective, clockwise rotation is called extension for a right femur and flexion for a left femur; (27) Femoral implant varus/valgus angle: Rotation about the AP axis of the femur. From an anterior perspective in the frontal plane, clockwise rotation is called varus for a right femur and valgus for a left femur; (28) Femoral internal/external rotation of the femoral implant: Rotation about the mechanical axis of the femur. From a distal perspective in the axial plane, clockwise rotation is called internal rotation on a right femur and external rotation on a left femur. The system gives the operator the option of expressing internal/external rotation relative to the TEA or the PCA; (29) Femoral distal resection levels (medial and lateral): The distance between the distal cut plane and the most distal condyle points, following the mechanical axis; (30) Femoral distal resection level: A level on the side with the most distal condyle point; (31) Femoral posterior resection levels (medial and lateral): The distances between the posterior cut plane and the most posterior points on the medial and lateral condyles.

Referencing FIGS. 90-93, as used herein, the following are mechanical neutral anatomic landmark definitions for the tibia: (1) Mechanical axis (MA): the axis between the ankle joint center and the proximal entry of the medullary canal; (2) Proximal Entry of the Tibial Mechanical Axis: The proximal entry medullary canal. This landmark is estimated to be at 33% anterior in the AP direction and at 50% of the transtibial axis, prolonged in medial and lateral to the bone surfaces; (3) Intercondylar Eminence Points: The two highest projecting points on the medial and lateral intercondylar eminences; (4) Eminence Midpoint: The midpoint between the lateral and medial intercondylar eminence points; (5) Tibial Tuberosity: The most anteriorly protruding point on the tibial tuberosity; (6) ML: Maximum width of the tibia plateau in the medial-lateral direction; (7) ML Axis of the Tibia: The cross-product of its AP direction with its mechanical axis; (8) AP: Length of the tibial plateau in the anterior-posterior (AP) direction and passing through the midpoint of the tibial intercondylar eminence (i.e. eminence midpoint); (9) AP Direction: The axis that joins the center of the attachment area of the posterior cruciate ligament (PCL) and a point on the medial third of the tibial tuberosity; (10) AP Axis of the Tibia: The cross-product of the tibia mechanical axis with its ML axis; (11) Eminence Width (EW): Distance between medial and lateral intercondylar eminence points; (12) Tibial Twist Angle (TTA): Angle between the AP direction and a line connecting the intercondylar eminence midpoint and tibial tuberosity; (13) Lateral Plateau Height (LPH): Length of the lateral tibial plateau in the AP direction; (14) Lateral Plateau Width (LPW): Length of the lateral tibial plateau in the ML direction; (15) Medial Plateau Height (MPH): Length of the medial tibial plateau in the AP direction; (16) Medial Plateau Width (MPW): Length of the medial tibial plateau in the ML direction; (17) Eminence ML Ratio (EMLR): Ratio of MPW (i.e. medial plateau width) over ML; (18) Maximum Length: Length of the tibia from the medial malleolus to the intercondylar eminence; (19) Posterior Tibial Axis (PTA): Line connecting the most posterior surfaces of medial and lateral tibial plateau; (20) Transtibial Axis: Line connecting the anterior posterior midpoints of the medial and lateral tibial plateaus; (21) Tibial Center: Exact midpoint of the transtibial axis; (22) Tibial Tuberosity Angle (TTA): Angle formed by a line from the center point of the tibial tuberosity to the tibial center compared to the anterior tibial axis; (23) Ankle Center: Midpoint of the proximal talus articular surface, about 45% lateral to the most medial prominence of the transmalleolar axis; (24) Ankle Joint Center: The midpoint of the axis joining the most lateral point of the lateral malleoli and the most medial point of the medial malleoli; (25) Transmalleolar Axis: Line connecting the prominence of the medial and lateral malleoli (or tips of the malleoli); (26) Slope of the Tibial Implant: Rotation about the ML axis of the tibial. From a lateral side perspective, clockwise rotation is called anterior slope of extension for a right tibia and called posterior slope or flexion for a left tibia; (27) Varus/valgus Angle of the Tibial Implant: Rotation about the AP axis of the tibia. From an anterior perspective in the frontal plane, clockwise rotation is called valgus for a right tibia and varus for a left tibia; (28) Internal/external Rotation of the Tibial Implant: Rotation about the mechanical axis of the tibia. From a proximal perspective in the axial plane, clockwise rotation is called external rotation on a right tibia and internal rotation on a left tibia. The system gives the user the option of expression tibial rotation relative to the AP axis or the PTA; (29) Medial Resection Level of the Tibia: The distance between the cut plane and the most distal point on the medial plateau, following the mechanical axis. Therefore, augmenting or diminishing the resection level will translate the cut plane along the mechanical axis; (30) Lateral Resection Level of the Tibia: The distance between the cut plane and the most distal point on the lateral plateau, following the mechanical axis. Therefore, augmenting or diminishing the resection level will translate the cut plane along the mechanical axis.

Referring back to FIGS. 85-89, as used herein, the following are kinematic alignment definitions for the femur: (1) Projected Plane Normal to PCA (PPNP): Intersection of plane normal to PCA with plane normal to tibia MA. The PPNP axis depends on the orientation of the femur relative to the tibia; (2) Meniscal Axis: The axis extending through the contact centers of the medial condyle and the lateral condyle when in contact with the tibia in extension.

Referring back to FIGS. 90-93, as used herein, the following are kinematic alignment definitions for the tibia: (1) Posterior Tibial Axis (PTA): Line connecting the most posterior surfaces of the medial and lateral tibial plateau.

The instant disclosure relates to guides and trials for use with total or partial knee replacement surgeries as well as femoral and tibial orthopedic implants. As will be discussed in more detail hereafter, the exemplary embodiments of the instant disclosure include tibial and femoral placement guides to facilitate placement of the tibial and femoral implant components, as well as methods of fabricating these placement guides, in addition to method of using the placement guides, as well as methods of fabricating and placing novel prosthetic apparatuses that more closely approximate the natural kinematics of the knee in comparison to present day knee prosthetic components.

As discussed previously, present day placement of prosthetic knee components is premised solely upon mechanical alignment. In particular, the center of the femoral head and center of the ankle (see FIG. 1), which are used by conventional, computer assisted surgery and personal cutting instruments to align TKA mechanically, have no bearing on the kinematics of the knee. And this mechanical alignment sacrifices kinematics as the mechanical references used for alignment are inconsistent with kinematic references, thereby leading to kinematics that are abnormal, patient discomfort, and premature joint failure. Instead, the present disclosure is premised upon taking a novel approach premised upon kinematic alignment of prosthetic components.

Kinematic alignment of the knee is based on the normal kinematics of the knee. Kinematics in this context refers to the relative relationship of the femur, patella and tibia at any angle of flexion without load bearing force applied to the knee. The knee joint surface, menisci, and ligament structures determine the normal kinematic relationship among the femur, patella, and tibia. The following is a discussion of populating a statistical atlas that will be described in more detail hereafter as part of generating mass-customized guides and orthopedic implants in accordance with the instant disclosure.

A premise supporting kinematic alignment of the knee is accounting for and replicating three axes that govern the movement of the patella and tibia with respect to the femur. The primary axis of these three axes is a first transverse axis (i.e., helical axis) in the femur about which the tibia flexes and extends. In order to determine this first transverse axis of a knee joint, the instant disclosure makes use of X-ray fluoroscopy to image the knee joint. More specifically, a knee joint is imaged at distinct points throughout its range of motion (e.g., between full extension and 160 degrees flexion). These fluoroscopic images are registered to 3D models of the knee joint, as discussed previously, which are specific to that knee joint (i.e., patient and knee side specific). After registering the 3D model to the fluoroscopic images, a first transverse axis fitting process is conducted.

Figure 19:
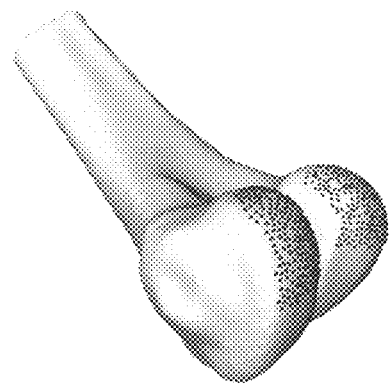
FIG. 19 is an elevated perspective view of a virtual femur model showing a series of surface points placed on the lateral and medial condyles on the posterior aspect.
Figure 20:
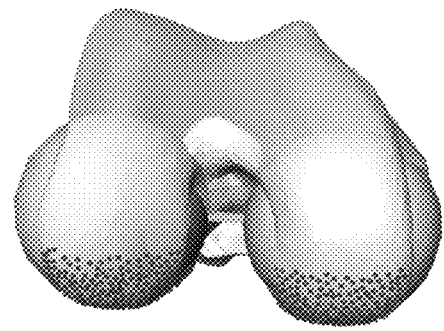
FIG. 20 is an end view of a virtual femur model having a sphere fit to each of the medial and lateral condyles using the surface points in FIG. 19 in accordance with the present disclosure.
Figure 21:
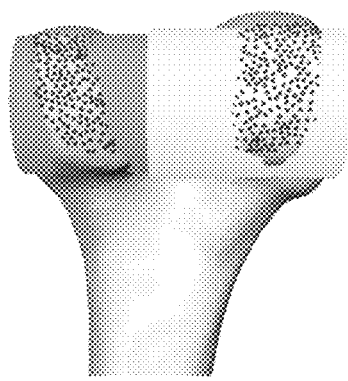
FIG. 21 is an end view of a virtual femur model having a cylinder fit to each of the medial and lateral condyles using the surface points in FIG. 19 in accordance with the present disclosure.
Figure 22:
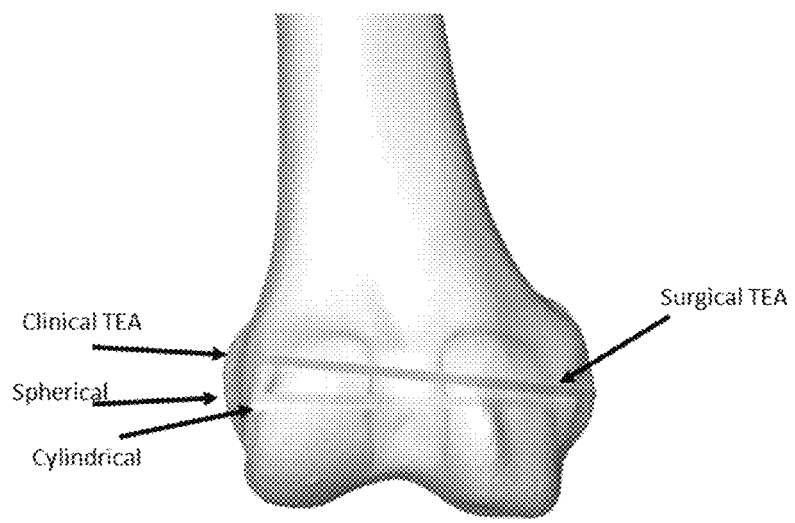
FIG. 22 is a graphical representation of a distal femur and comparison of the surgical transepicondylar axis, the clinical transepicondylar axis, the spherical axis, and the cylindrical axis.
Figure 23:
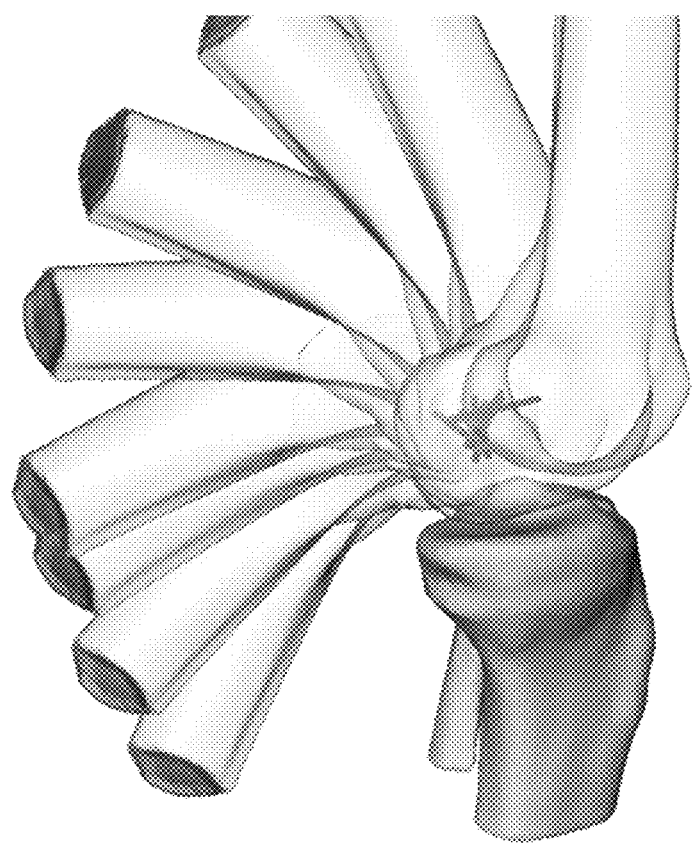
FIG. 23 is a range of motion view showing how the femur moves with respect to the tibia and how the position of the femoral helical axis changes with this motion.
Figure 24:
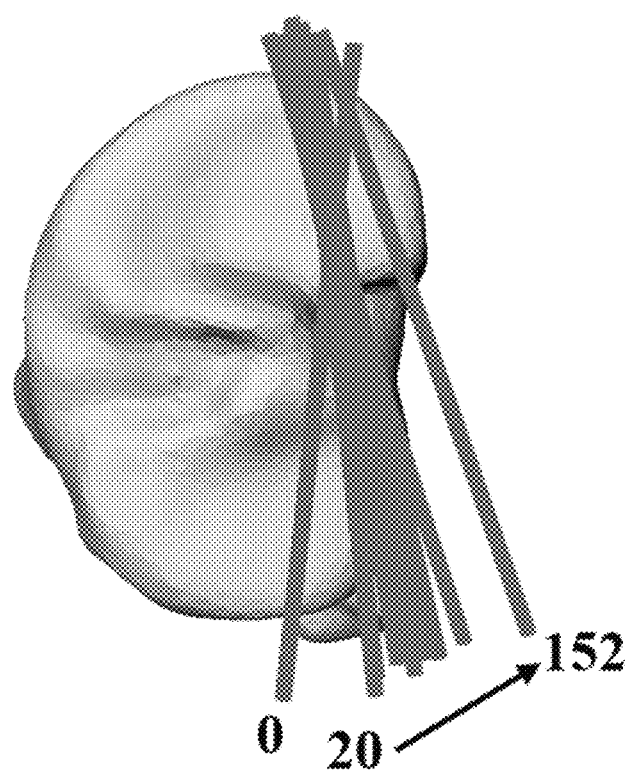
FIG. 24 is a graphical depiction showing how the femoral cylindrical axis changes across a range of motion between full extension (zero degrees) and a deep knee bend (152 degrees).
Figure 25:
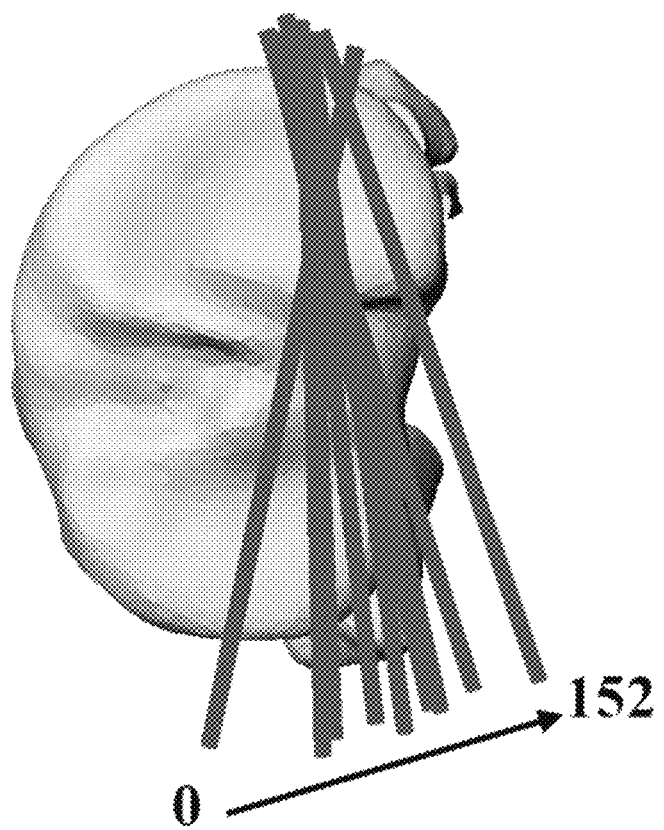
FIG. 25 is a graphical depiction showing how the femoral spherical axis changes across a range of motion between full extension (zero degrees) and a deep knee bend (152 degrees).
Figure 26:
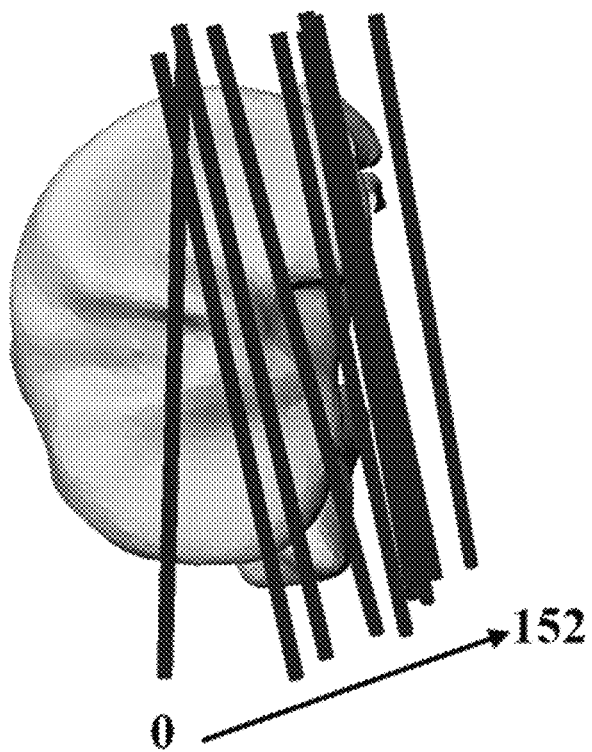
FIG. 26 is a graphical depiction showing how the femoral transepicondylar axis changes across a range of motion between full extension (zero degrees) and a deep knee bend (152 degrees).
Figure 27:
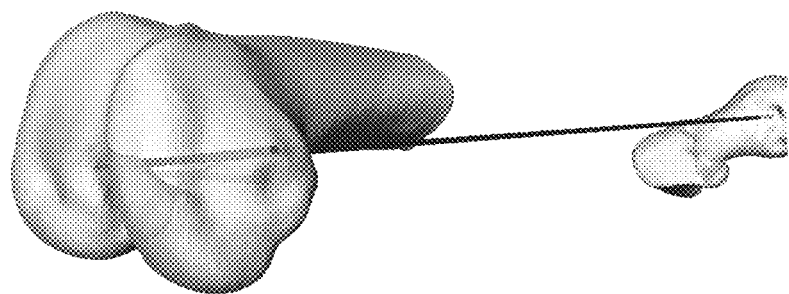
FIG. 27 is a graphical depiction of the clinical and surgical transepicondylar axis of the femur.
Figure 28:
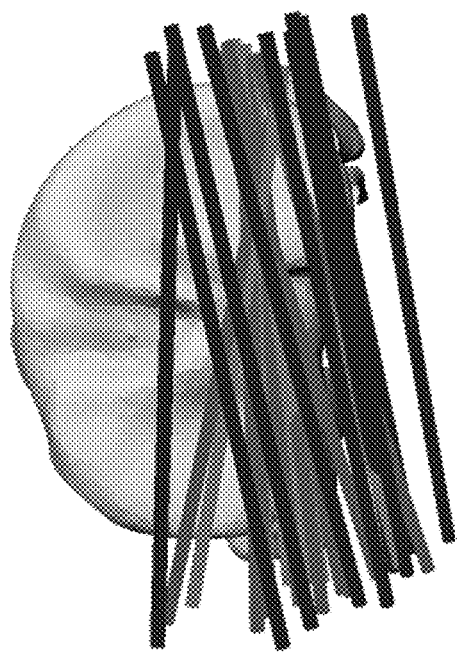
FIG. 28 is an overlay compilation of the graphical depictions from FIGS. 24-26.
Figures 29A, 29B:
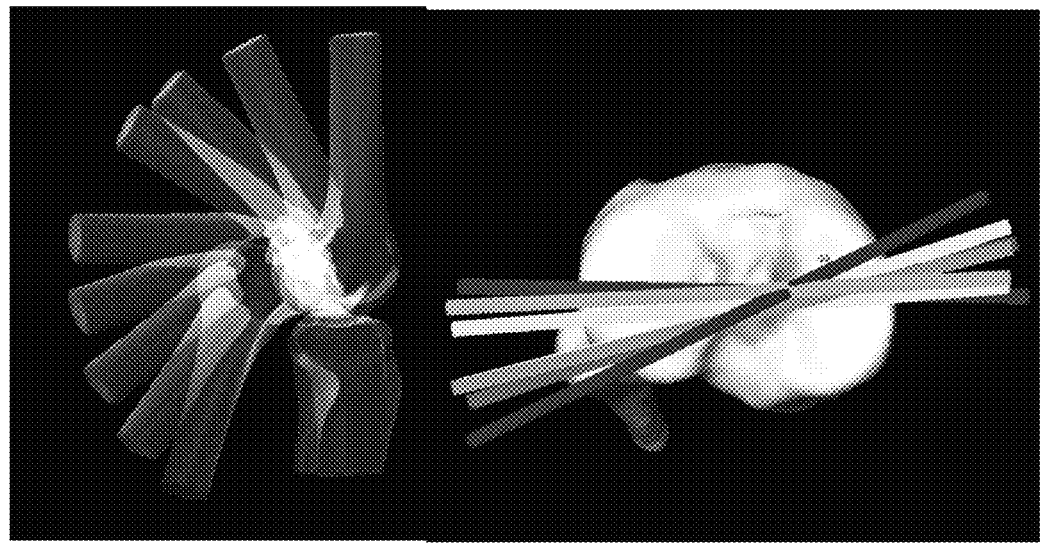
FIGS. 29A and 29B includes a range of motion view of the femur with respect to the tibia and an overhead view of the tibia showing how the helical/transverse axis of the femur changes with this range of motion.
Figure 30:
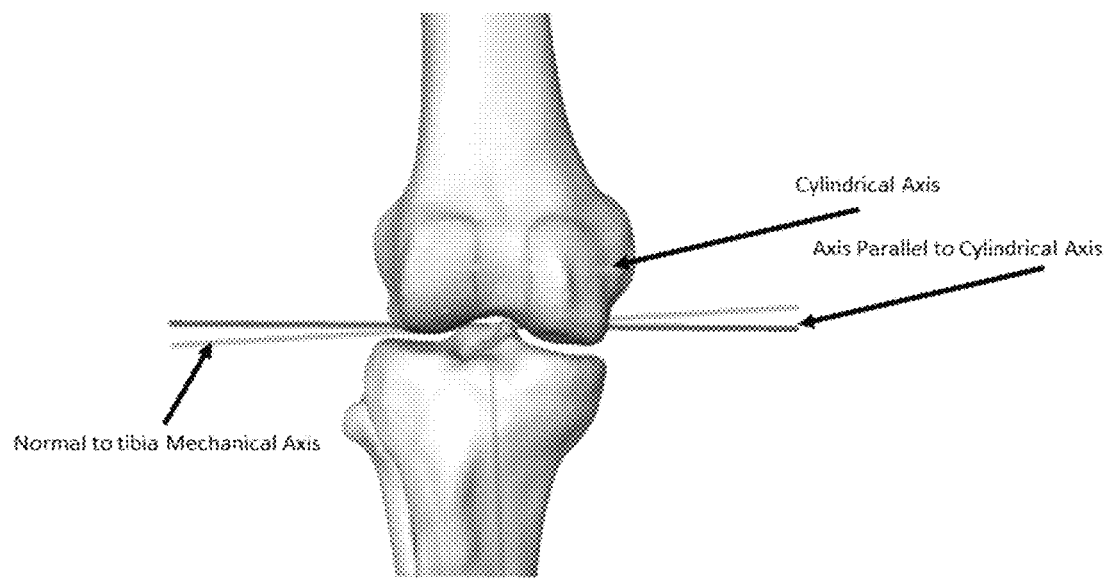
FIG. 30 is a graphical representation showing the cylindrical axis of the femur is not normal with respect to the tibial mechanical axis.

The first transverse axis fitting process involves fitting a sphere or cylinder to each joint condyle and, using this shape fitting information, calculating the transverse axis. Specifically, a circular or cylindrical shape is fit to the articular surfaces of the femoral and tibial condyles ranging between 10 to 160 degrees of flexion (see FIGS. 19-21). The hypothesis behind using the spherical or cylindrical axes is to approximate the true axis of rotation of the femur on the tibia. In order to determine the circular or cylindrical shape dimensions, for a given three dimensional model replicating the morphology of the bones of the knee joint (tibia, fibula, femur), a point cloud is generated by a computer software program from the 3D knee joint model, where each point in the cloud represents a surface point on the articular surface in question (with two articular surfaces for the distal femur and two articular surfaces for the proximal tibia). Each point cloud is then best fit to either a sphere or cylinder with known dimensions, after which the transverse axis extending through both spheres/cylinders is calculated by the software program (see FIG. 22). The first transverse axis is calculated across the range of motion captured by the 3D knee model, thus indicating how the transverse axis changes throughout the range of motion of the knee joint. In contrast to this kinematic alignment approach, conventional wisdom suggests that the TEA (clinical or surgical) mechanical axis is the axis of rotation of the femur on the tibia (see FIGS. 26 and 27). But the TEA mechanical alignment results in little to no rotation between the femur and tibia (see FIG. 26), which is by no means consistent with normal knee kinematics.

Figure 31:
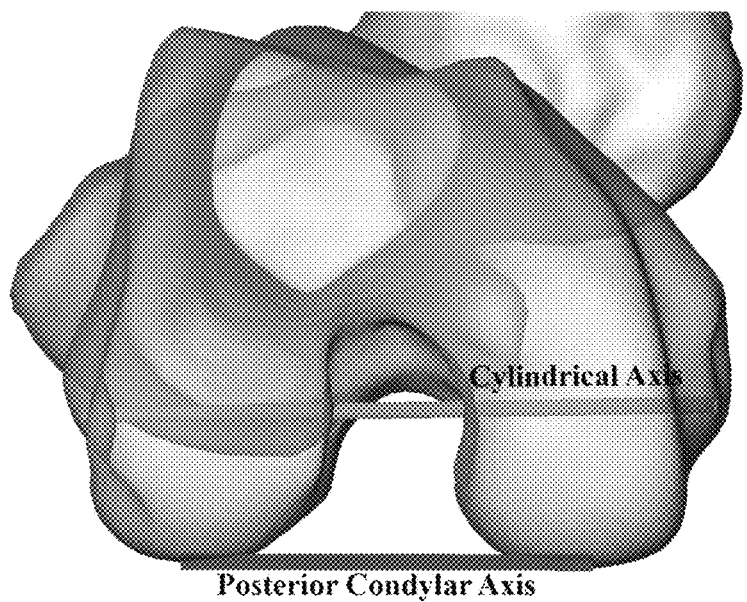
FIG. 31 is a graphical representation of the distal femur showing the posterior condylar axis and the cylindrical axis are almost consistently parallel.
Figures 32A, 32B, 32C, 32D:
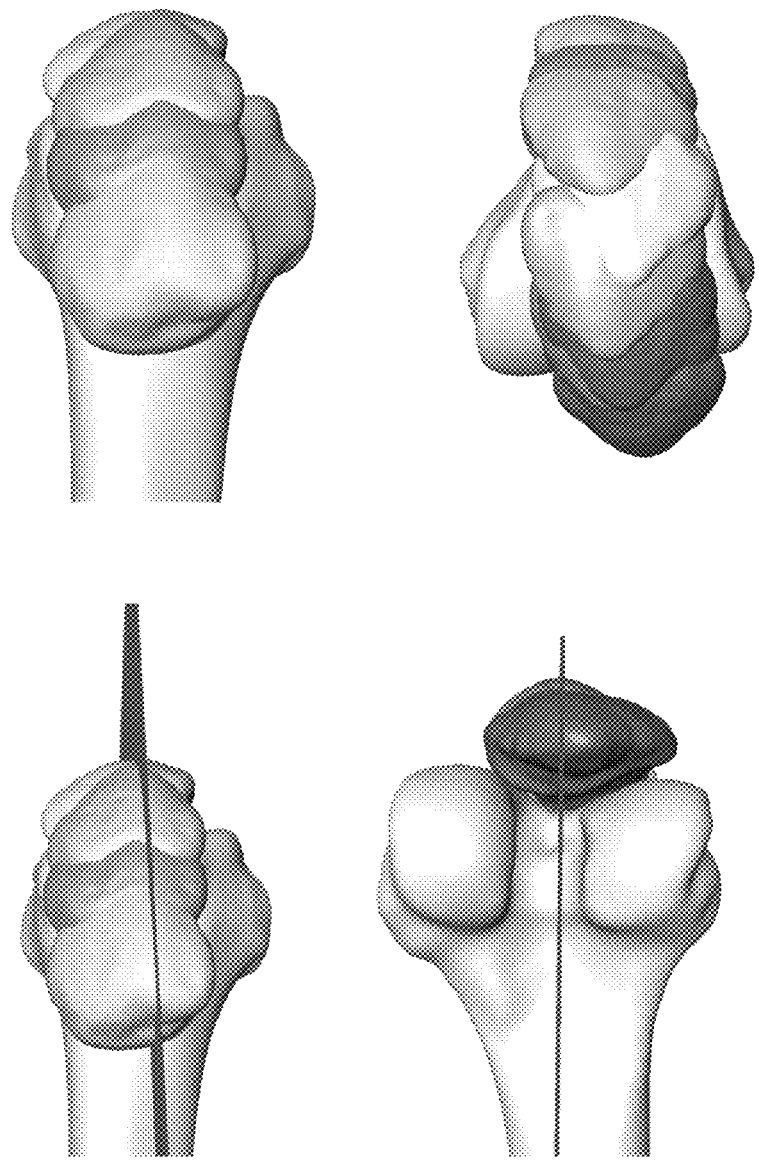
FIGS. 32A-32D are multiple views of a femur showing patella motion and tracking this motion in accordance with the instant disclosure via the intersection with the sagittal kinematic plane.
Figures 33A, 33B, 33C, 33D, 33E, 33F:
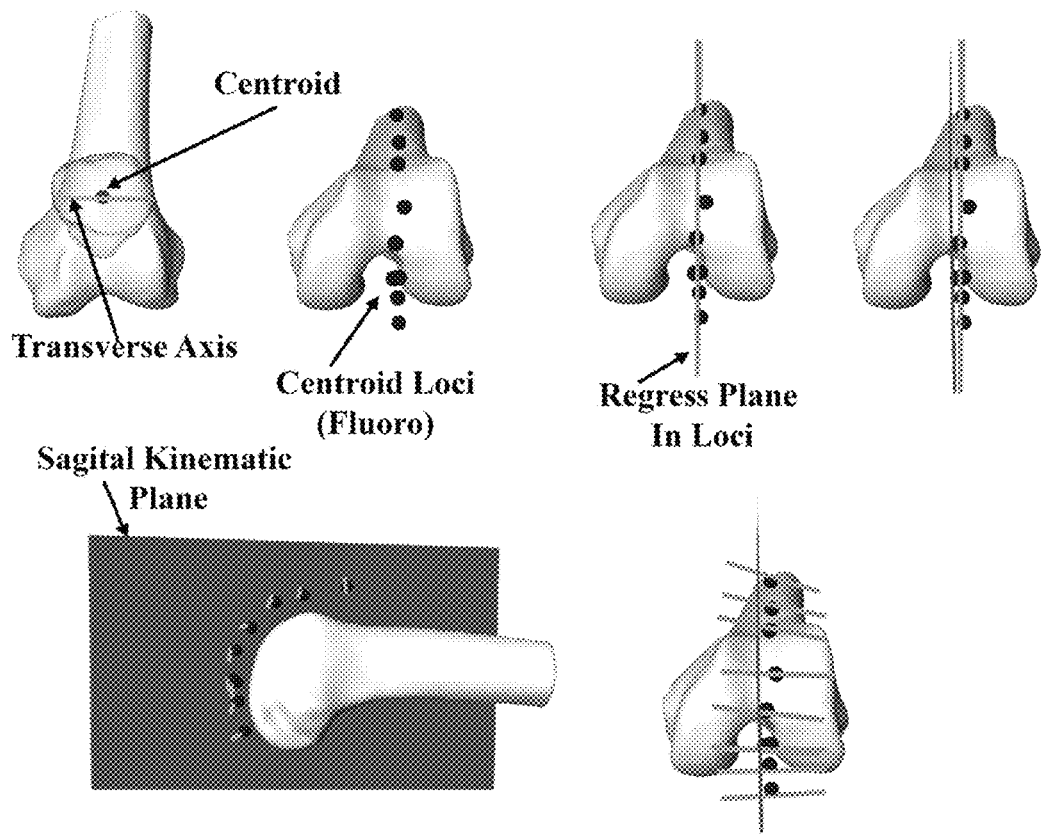
FIGS. 33A-33F are a series of images depicting how the motion of the patella is tracked with respect to the sagittal kinematic plane.
Figure 34:
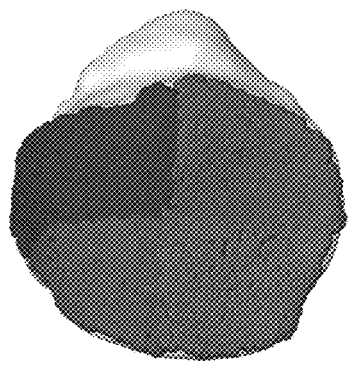
FIG. 34 is a graphical depiction of a patella virtual model constructed from surface points across four quadrants.
Figures 35A, 35B:
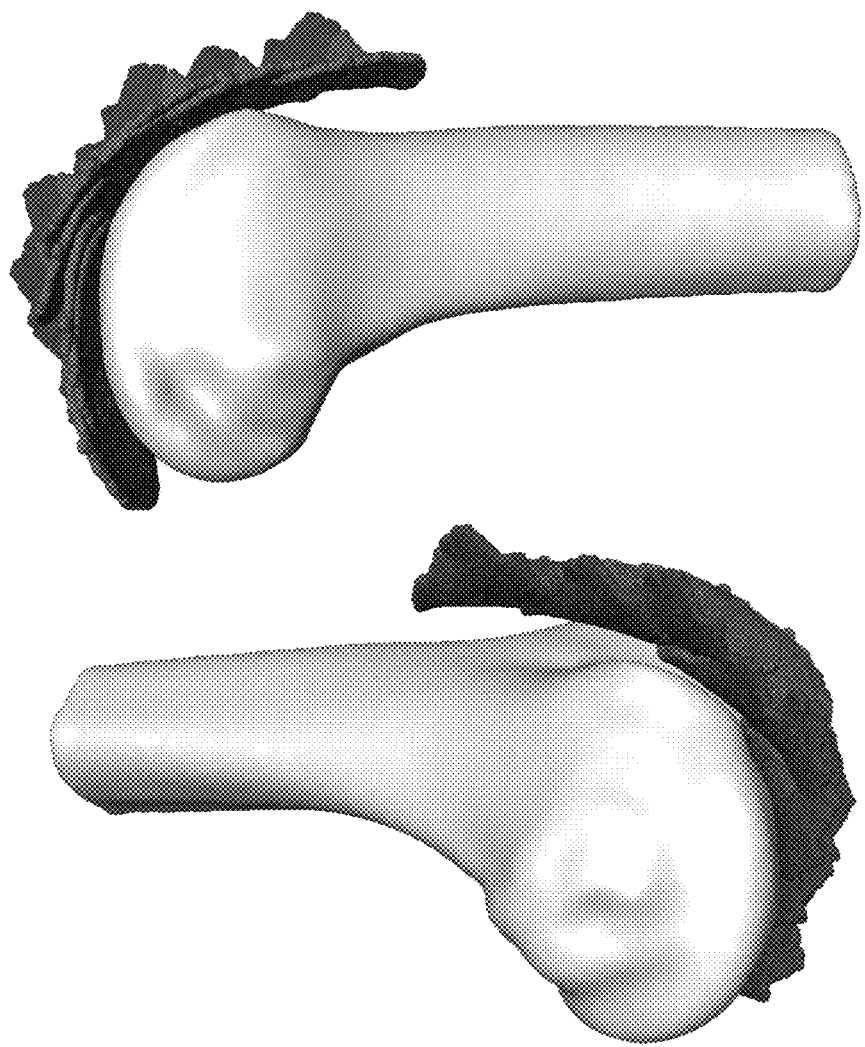
FIGS. 35A and 35B are medial and lateral views of a femur showing the natural motion of the patella contact surfaces with respect to the femoral trochlear groove.
Figures 36A, 36B, 36C, 36D:
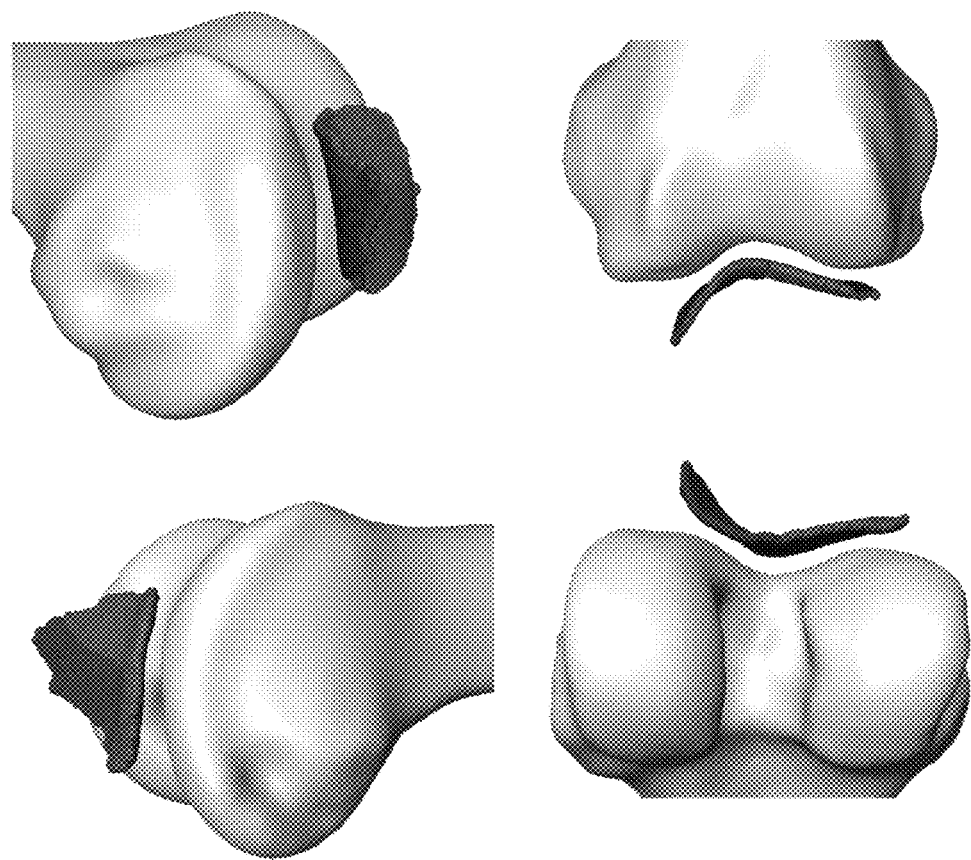
FIGS. 36A-36D are various views showing how the contact surfaces of the patella embodies roughly the same curvature as the trochlear groove.
Figure 37:
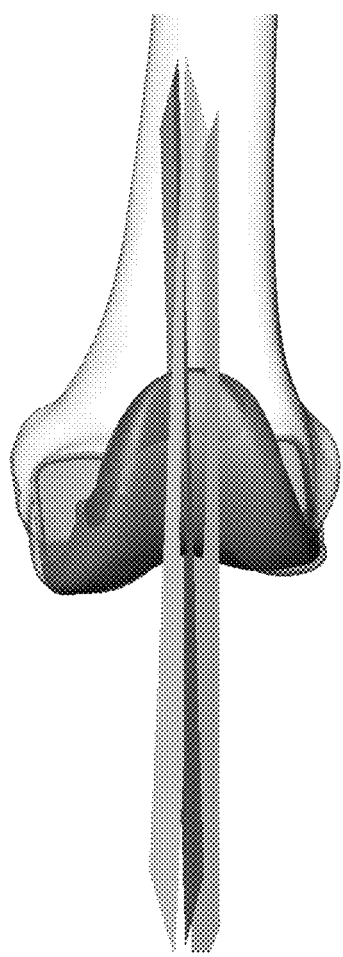
FIG. 37 depicts graphically the angular differences between the sagittal kinematic plane, the patella loci plane, and the femoral implant plane.

An ancillary axis to the first transverse axis for kinematic alignment is the PCA. The PCA is approximately parallel to the transverse axis and may be used in aligning the femur (see FIG. 31). After knowing the first transverse axis, the PCA is calculated by determining the most posterior points on the medial and lateral condyles of the distal femur.

There is a second transverse axis, which is a second of the three kinematic axes, in the femur about which the patella flexes and extends (see FIGS. 32A-32D). This second transverse axis is parallel, proximal, and anterior to the first transverse axis in the femur about which the tibia flexes and extends. However, it is not easily reproduced or approximated by a known biomechanical (or clinical) axis.

In order to determine the second transverse axis about which the patella flexes or extends, the center of mass of the patella (Loci) is tracked with respect to the femur using X-Ray fluoroscopy (see FIGS. 32A-33F). In particular, as discussed above, a knee joint is imaged at distinct points throughout its range of motion (e.g., between full extension and 160 degrees flexion). These fluoroscopic images (including femur, patella, fibula, and tibia) are registered to 3D models of the knee joint, as discussed previously, which are specific to that knee joint (i.e., patient and knee side specific). After registering the 3D model to the fluoroscopic images, a second transverse axis fitting process is conducted.

Figure 39:
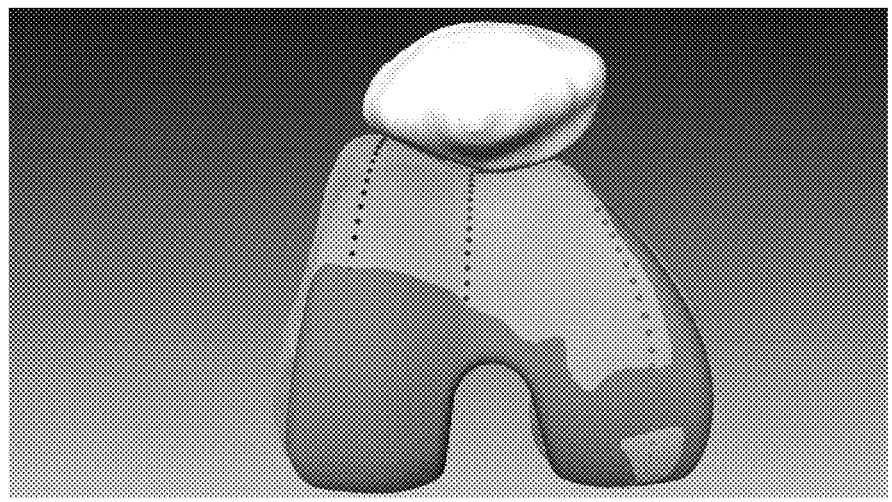
FIG. 39 is an end view of a TKA femoral component constructed in accordance with the instant disclosure that includes a trochlear groove that is kinematically aligned.
Figure 40:
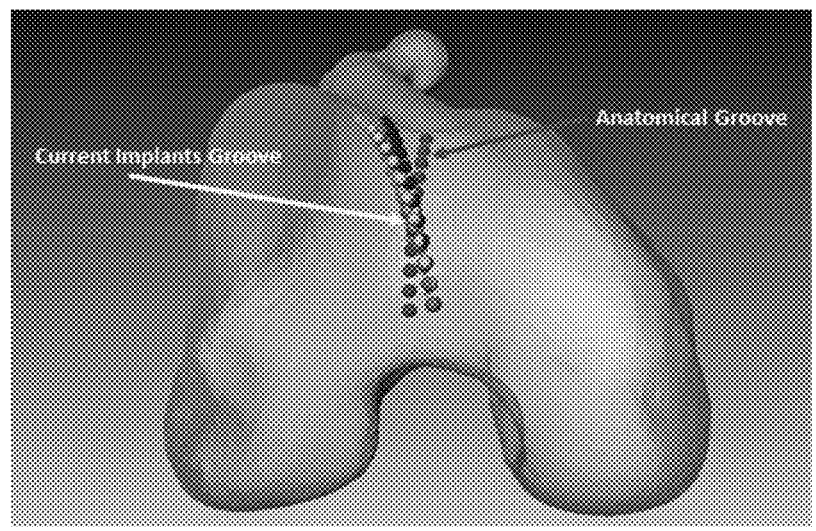
FIG. 40 is an end view of a distal femur showing how present day implants trochlear groove is considerably different from the trochlear groove of the kinematic femoral component fabricated in accordance with the instant disclosure.

This second transverse axis fitting process involves determining the position of the patella loci (i.e., centroid) for each fluoroscopic image. In exemplary form, a software package determines the loci for each fluoroscopic image with respect to the femur. Each loci is then plotted as a point with respect to the 3D femur model, which creates a series of points—one for each fluoroscopy image—in 3D space with respect to the femur 3D model. The software then conducts a planar regression on the loci points to establish a best fit plane, which is either parallel or almost parallel with the sagittal kinematic plane extending through the femur. Likewise, the fitting process involves fitting a sphere or cylinder to each patella loci and, using this shape fitting information, calculating the second transverse axis. Specifically, a circular or cylindrical shape is fit to the loci across a knee range of motion, for example, between 10 to 160 degrees of flexion. It should be note that the loci points in 3D space essentially replicate a curve, and it is this curve that is fit to the curvature of the sphere or cylinder. The hypothesis behind using the spherical or cylindrical axes is to approximate the true axis of rotation of the patella about the femur. In sum, the software best fits either a sphere or cylinder with known dimensions to the loci points, after which the second transverse axis extending through the sphere/cylinder is calculated by the software program to be perpendicular to the sagittal kinematic plane. In contrast to this kinematic alignment approach, conventional orthopedic implants the patella groove angle is not parallel to or closely approximates a parallel orientation with respect to the sagittal plane. Moreover, quadriceps length is not restored by current implant designs (see FIGS. 38-40).

Figures 41A, 41B, 41C:
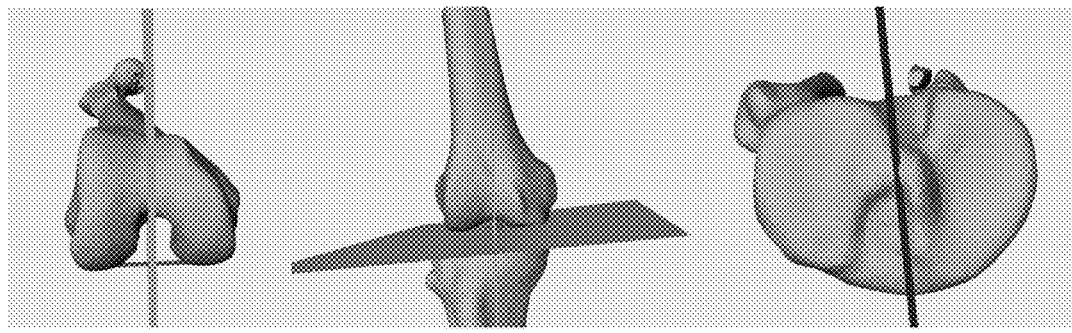
FIGS. 41A-41C depict initially the femoral postcondylar axis (PCA) and the intersection of a plane normal to the PCA, and then depict the intersection of a plane normal to the PCA with a plane normal to the tibial mechanical axis, and finally depicting the a plane normal to the PCA imposed onto the proximal tibia.

The third of the three axes is a longitudinal axis in the tibia about which the tibia internally and externally rotates on the femur. This longitudinal axis is perpendicular to each of the first and second transverse axes in the femur. This longitudinal axis is parallel to the sagittal kinematic plane, which is perpendicular to the posterior PCA of the femur (see FIG. 41).

Figure 42:
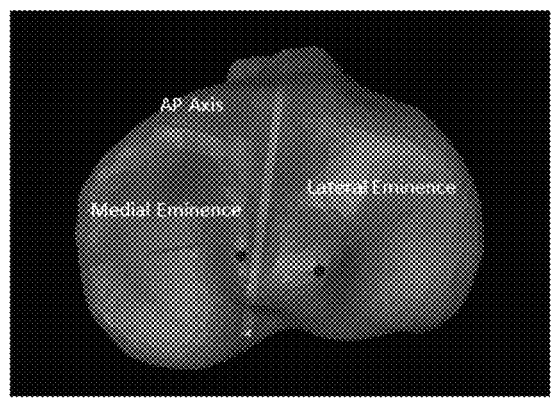
FIG. 42 is a graphical representation of the proximal tibia having calculated traditional tibia landmarks that include the medial eminence, lateral eminence, and AP1/3 Tubercle posterior cruciate ligament.
Figures 43A, 43B:
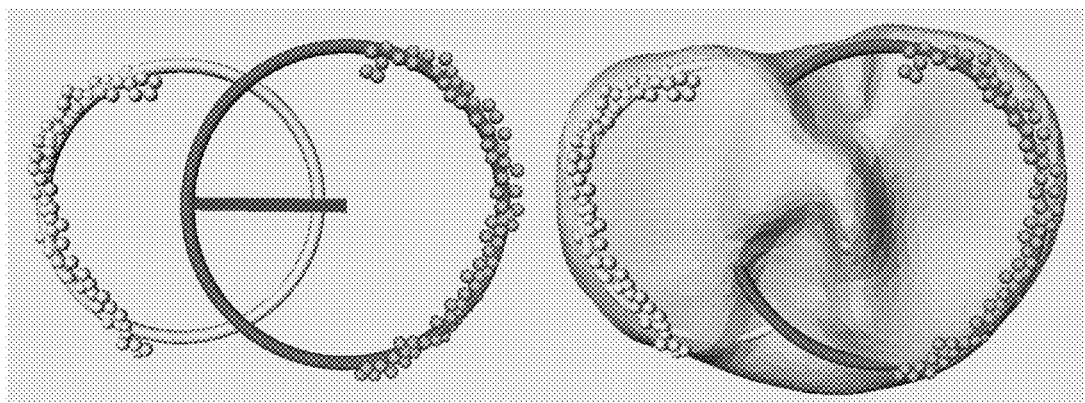
FIGS. 43A and 43B are graphical representations showing how the Cobb axis is determined using peripheral points on the medial and lateral condyles and circles approximating the curvature of the condyles.
Figures 44A, 44B, 44C:
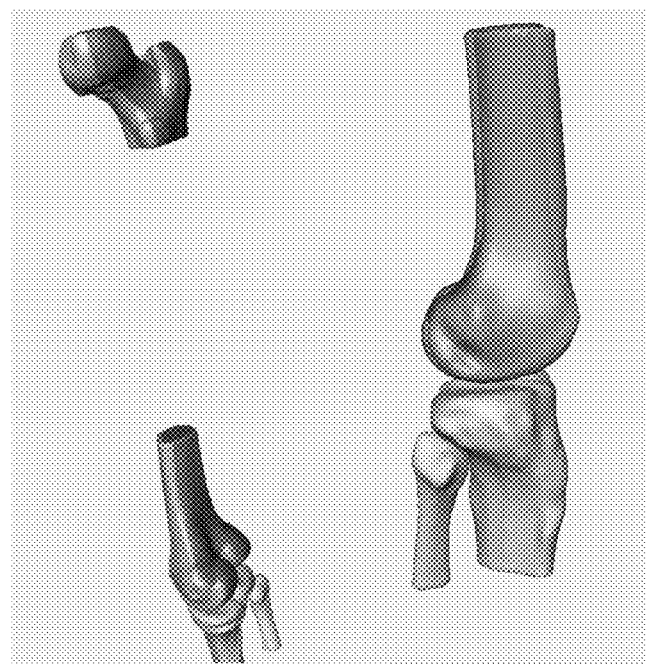
FIGS. 44A-44C comprises multiple views of positions of the femur with respect to the tibia across a range of motion that are either load bearing (red) or non-load bearing (blue).
Figure 45:
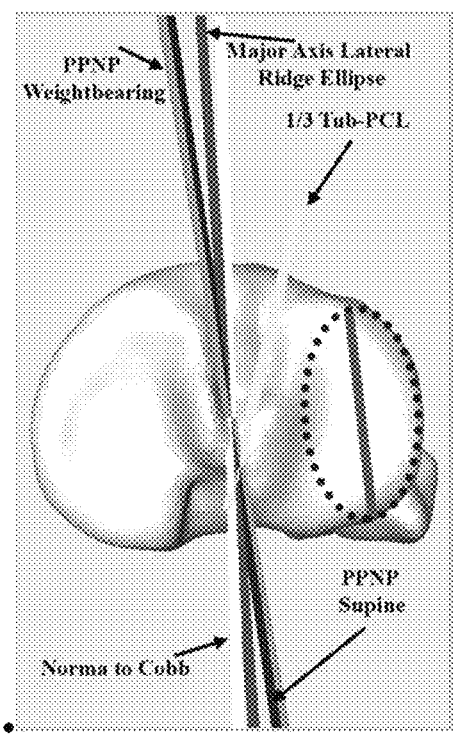
FIG. 45 is an overhead view of a proximal tibia showing the orientation of various axes.
Figure 46:
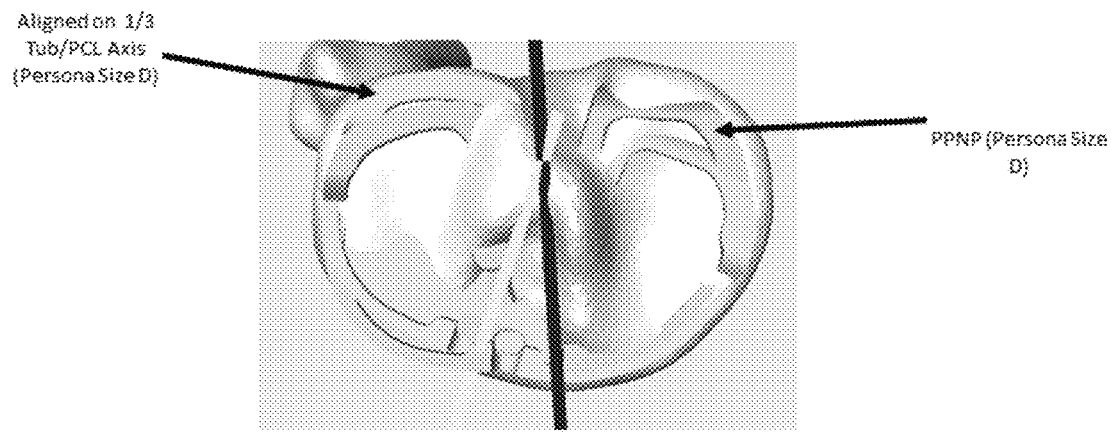
FIG. 46 is a comparison overhead view showing mechanical alignment versus kinematic alignment of a commercially available tibial tray on a proximal tibia.
Figure 47:
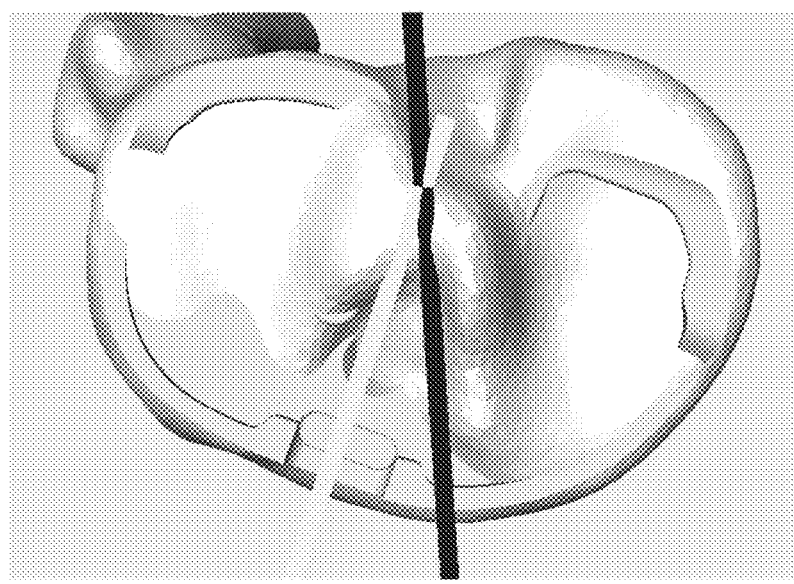
FIG. 47 is an overhead view showing mechanical alignment of a commercially available tibial tray on a proximal tibia.
Figure 48:
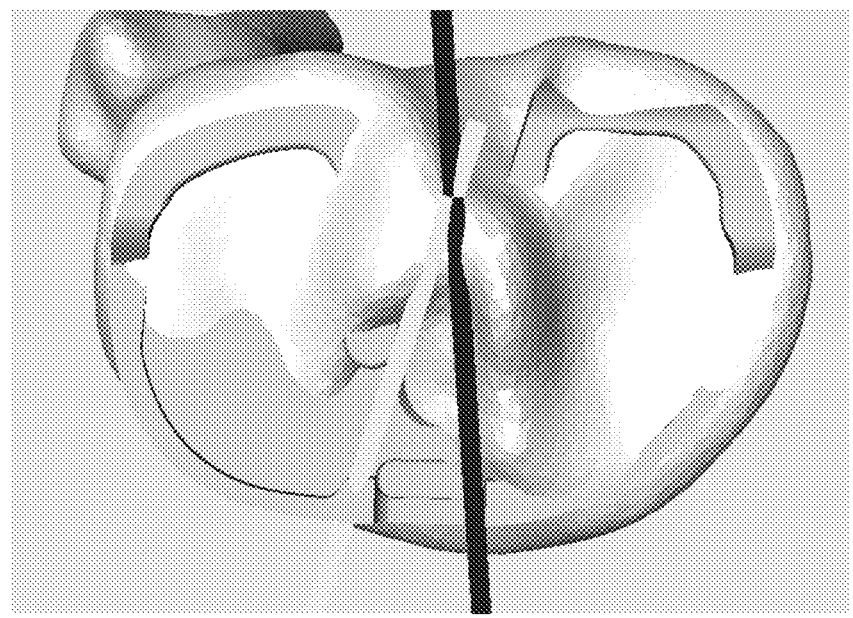
FIG. 48 is an overhead view showing kinematic alignment of a commercially available tibial tray on a proximal tibia.
Figure 49:
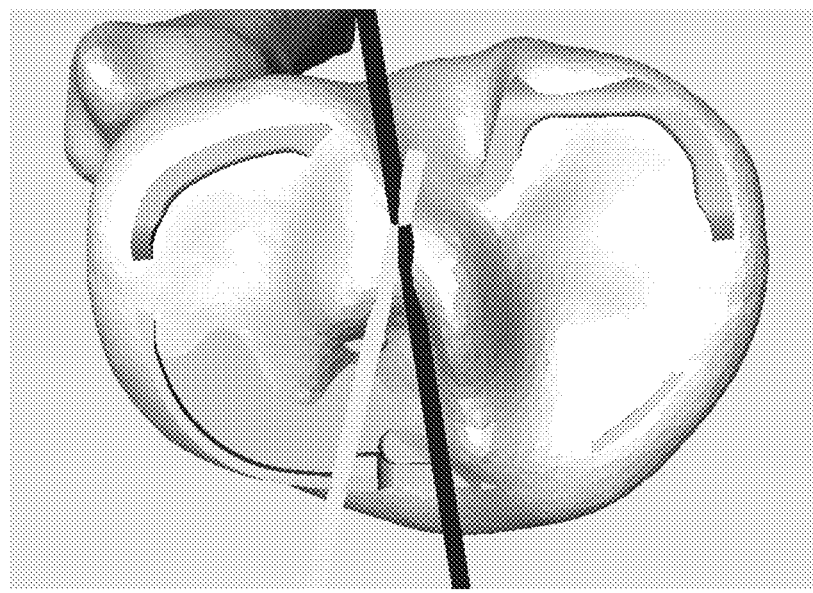
FIG. 49 is an overhead view showing kinematic alignment of a smaller commercially available tibial tray on a proximal tibia.
Figures 50A, 50B:
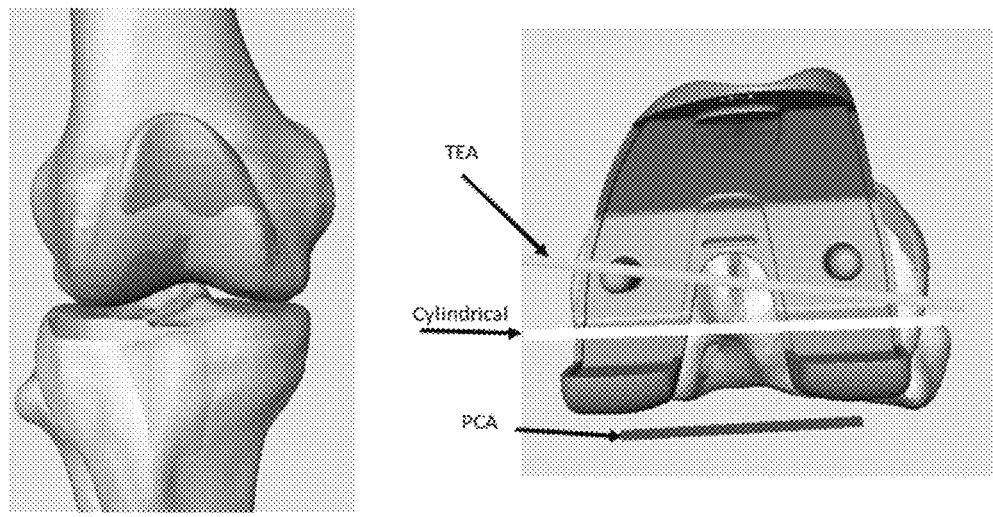
FIGS. 50A and 50B are comparison views showing femoral component alignment when aligned with the femoral PCA.
Figures 51A, 51B:
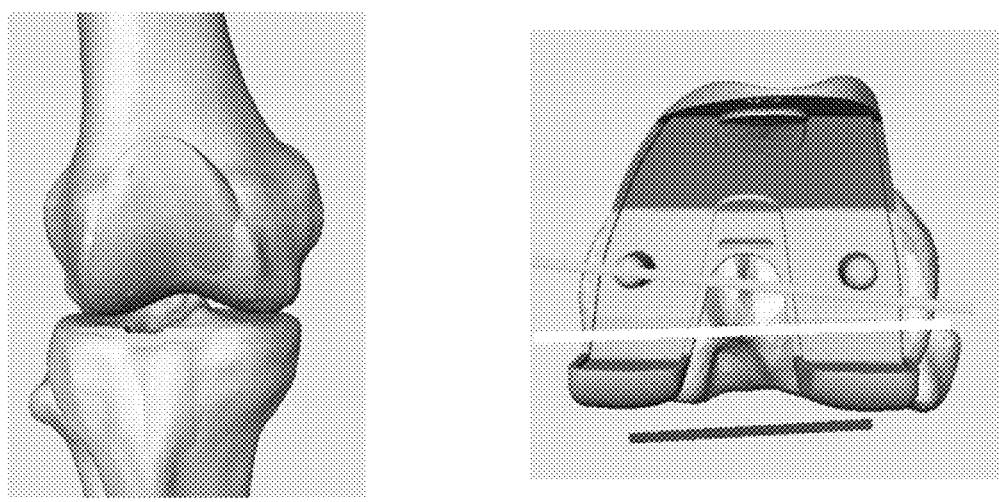
FIGS. 51A and 51B are comparison views showing femoral component alignment when aligned with the femoral PCA plus three degrees of offset.
Figure 52:
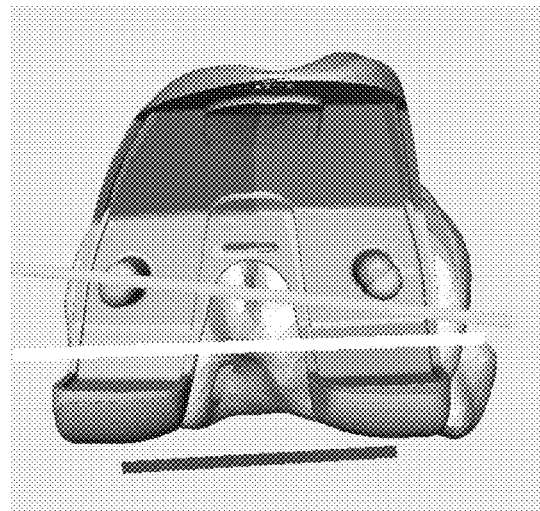
FIG. 52 shows femoral component rotational alignment.
Figures 53A, 53B:
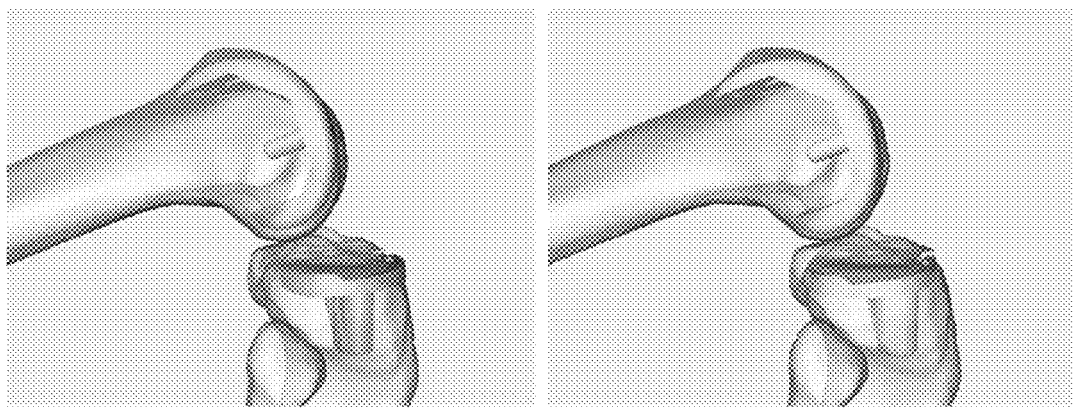
FIGS. 53A and 53B show multiple views of kinematic alignment between femoral and tibial components of a TKA.
Figures 54A, 54B:
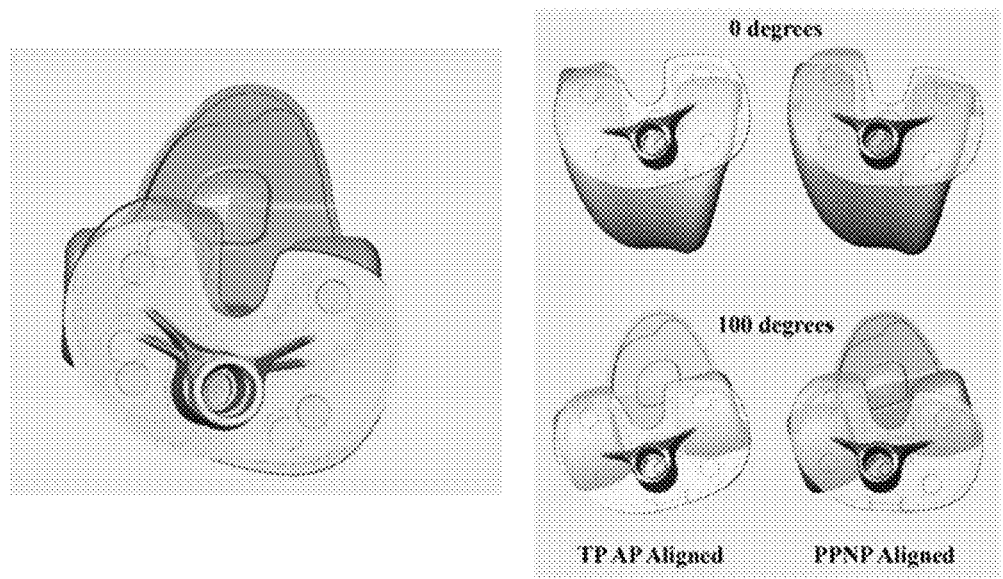
FIGS. 54A and 54B show multiple views of a femoral component with respect to a tibial component using mechanical alignment and kinematic alignment (PPNP).

As part of the instant technique, the Projected Plane Normal to PCA (PPNP) (i.e., sagittal kinematic plane) was compared to traditional landmarks (see FIGS. 42 and 43A, 43B). In addition, the sagittal kinematic plane was compared in both supine and weight bearing positions for the same subjects/patients (See FIGS. 44A, 44B and 45), with no significant differences being observed. What this means is that weight bearing images are not necessary as part of the instant process to create kinematic guides in accordance with the instant disclosure.

However, as part of the instant technique, a large angular rotation was observed between the PPNP and the ⅓ Tubercle-PCL of approximately 14 degrees (see FIGS. 46-53B). Accordingly, the inventor concluded that a different tibial plate design for the kinematic alignment was needed.

Figure 55:
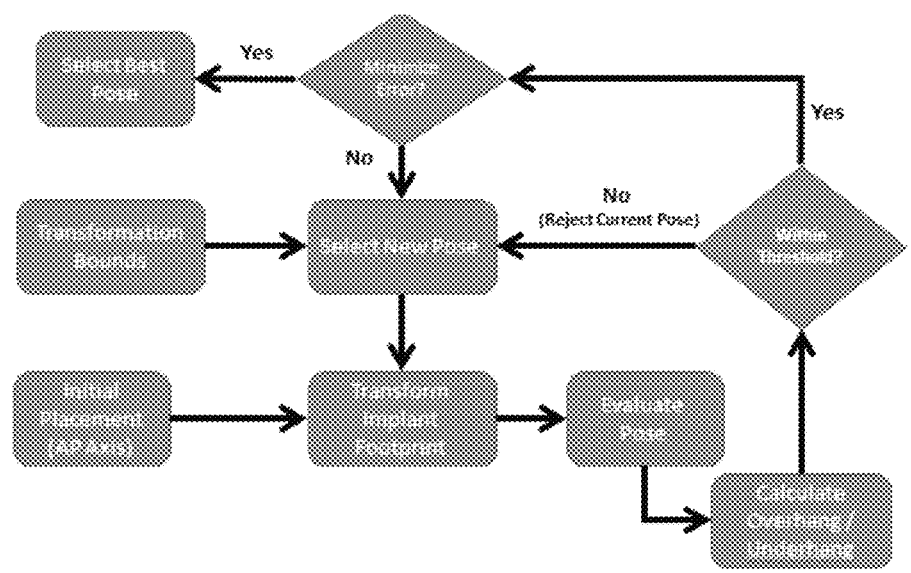
FIG. 55 is a process flow diagram depicting an exemplary process for generating an optimal implant placement.

Referring to FIG. 55, a flow diagram is illustrated for an exemplary process in accordance with the instant disclosure. In particular, the flow diagram presents an exemplary process for determining the best position/pose for a given orthopedic implant. As will be discussed in more detail hereafter, the output of the flow diagram is the position the orthopedic implant should occupy when mounted to bone or another orthopedic component. In order to utilize this best pose information, the instant disclosure makes use of novel alignment guides that includes references thereon to ensure proper alignment of the implanted orthopedic component.

The process flow diagram is carried out electronically as part of a software package that automatically calculates position of a given orthopedic implant with respect to a template bone model or a patient specific bone model. For purposes of explanation, it is presumed that the example refers to a patient specific case. Nevertheless, those skilled in the art will readily understand the applicability of the exemplary process flow in cases involving non-patient specific implants and bone models (e.g., mass customized orthopedic implants and template bone models).

Figures 56A, 56B:
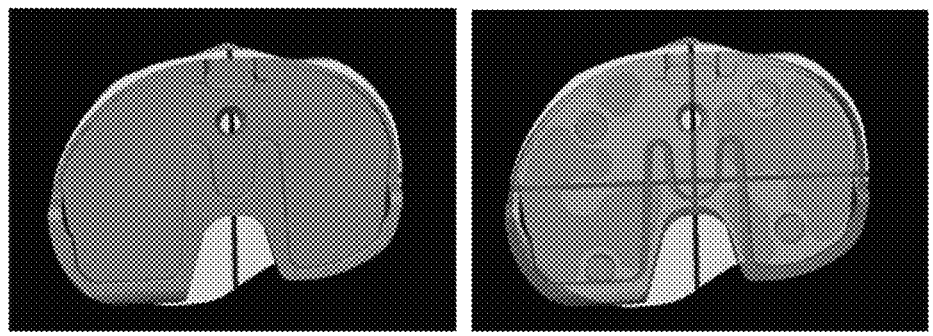
FIGS. 56A and 56B are graphical depictions of initial tibial placement pursuant to the process flow diagram of FIG. 55.
Figures 57A, 57B:
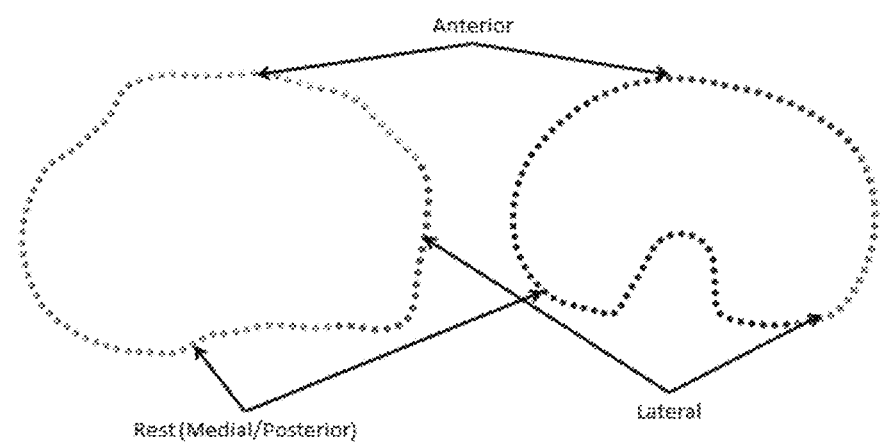
FIGS. 57A and 57B are outline comparisons of the resected tibia and a commercially available tibial tray implant.

As an initial matter, the patient's bone 3D bone model is virtually cut in accordance with protocols from the manufacturer of the orthopedic implant in question. Using this virtual bone cut (VBC), an initial placement of a virtual model of the intended orthopedic implant (VM) is positioned in accordance with the anterior-posterior axis (see FIG. 56A). This initial placement of the VM is transformed into a 2D footprint that overlaps the VBC, where the position of the footprint is evaluated (see FIG. 56B). In particular, this evaluation includes determining the axes of the 2D footprint and comparing these axes to the one or more of the transverse axes and the longitudinal axis discussed previously. Post evaluation, calculations are made of the 2D footprint of the VM with respect to the VBC to determine and to what extent overhang and underhang areas are present. This evaluation makes use of the outline of the VBC and the 2D footprint of the VM (see FIGS. 57A and 57B). In other words, if the 2D footprint of the VM leaves exposed portions of the VBC, these areas are referred to as underhang areas, whereas aspects of the 2D footprint of the VM extending beyond (i.e., overhangs) the VBC are referred to as overhang areas. The calculations concerning overhang and underhang areas, in addition to calculations showing deviation between the axes of the 2D footprint of the VBC and one or more of the transverse axes and the longitudinal axis, are directed to a threshold sequence to discern whether or not the deviations are within a predetermined tolerance.

Figures 58A, 58B:
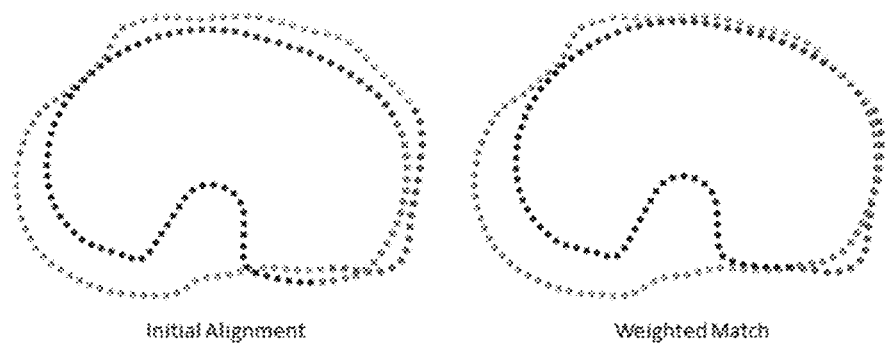
FIGS. 58A and 58B are graphical depictions showing the difference in tibial tray placement on a resected tibia in accordance with the process of FIG. 55, where the initial alignment is refined to the weighted match.
Figure 59:
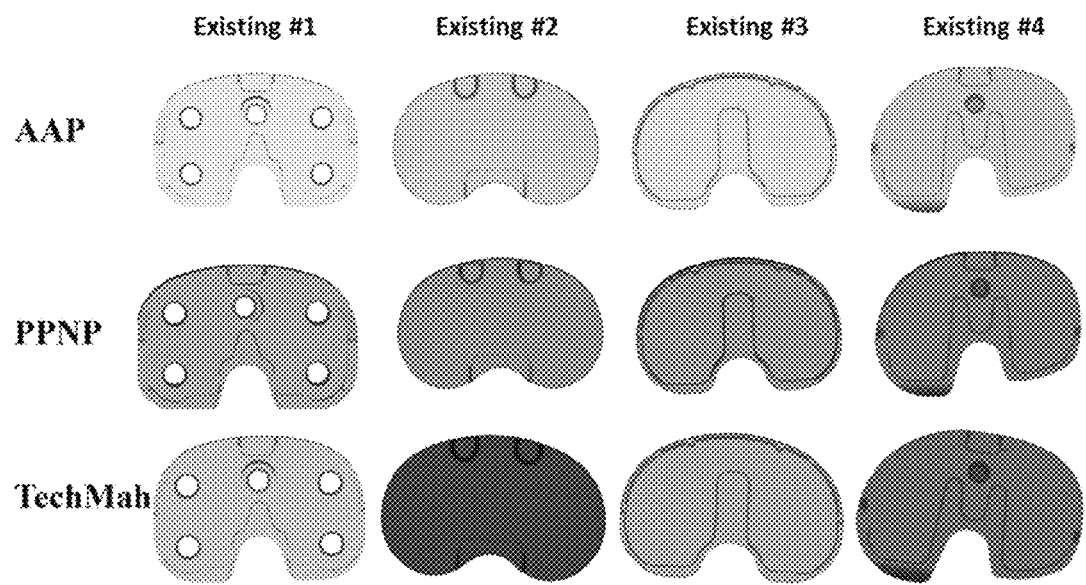
FIG. 59 comprises a series of commercially available tibial tray implants grouped according to alignment technique.

If the answer is "yes," the pose information is visually made available via a user graphical interface to allow for human intervention and further error minimization. Presuming the human operator is satisfied with the pose (see FIG. 58B), the pose becomes final and an implant guide based upon this pose is fabricated. Conversely, if the human operator is unsatisfied with the pose (see FIG. 58A), a new pose is selected by the software (or manually by the operator) taking into account certain transformation bounds. This newly selected pose step is also the result if the threshold sequence determines that the deviations calculated were not within acceptable tolerances. Presuming a new pose is selected/generated, the software generates a 2D footprint of the selected orthopedic implant in question for this revised pose, then evaluates the revised pose, and calculates overhang and underhang areas. The calculations for the revised pose are evaluated by the threshold sequence, where downstream subprocesses are repeated as necessary until reaching the final pose for the orthopedic implant. At the time the final pose is confirmed, the software also generates instructions sufficient to select or fabricate the correct implant guide.

Figure 60:
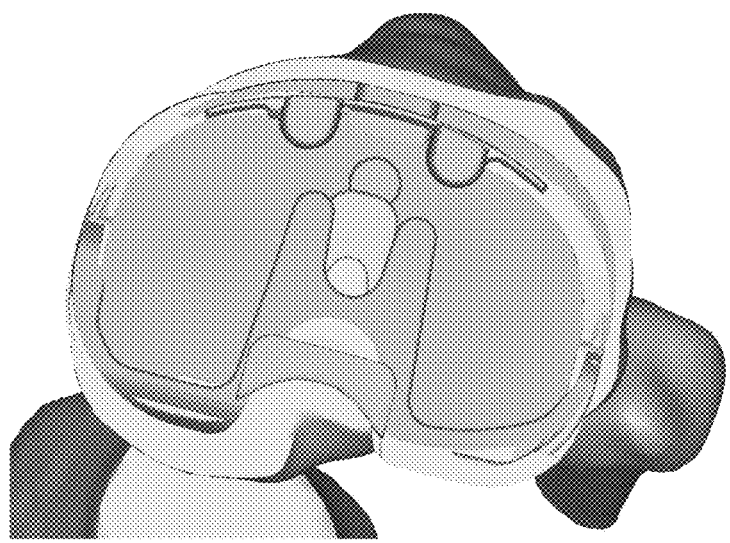
FIG. 60 is an overhead view of a tibia superimposed with the images of four commercially available tibial trays positioned via mechanical alignment.
Figure 61:
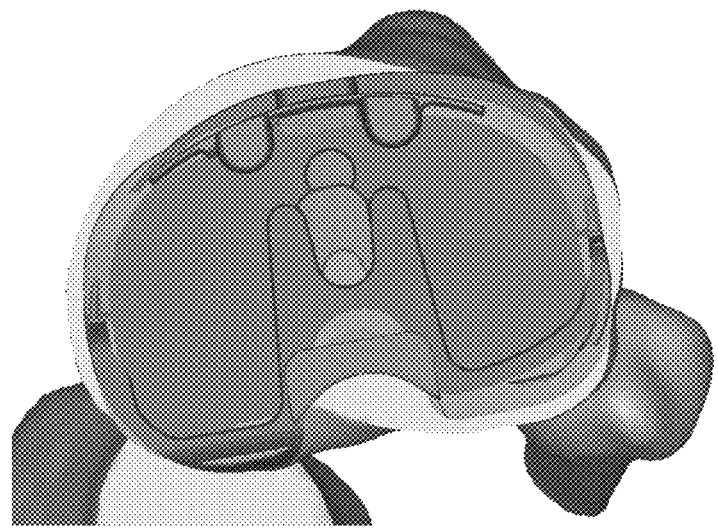
FIG. 61 is an overhead view of a tibia superimposed with the images of four commercially available tibial trays positioned via kinematic alignment in accordance with the instant disclosure.
Figure 62:
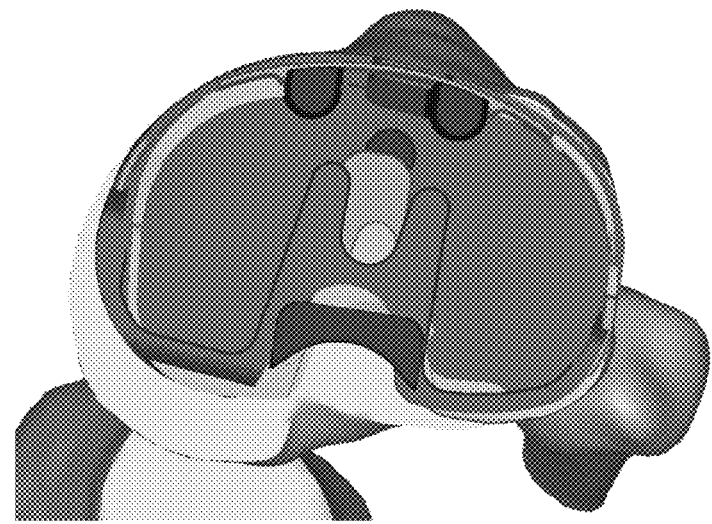
FIG. 62 is an overhead view of a tibia superimposed with the images of four commercially available tibial trays positioned via refined mechanical alignment.
Figure 63:
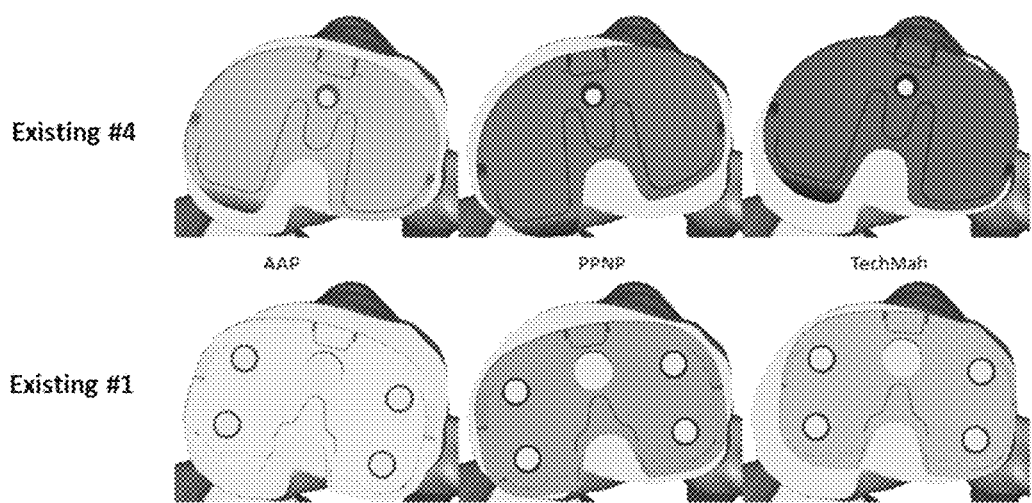
FIG. 63 includes a series of overhead views of a tibia having mounted thereto the first and fourth commercially available tibial tray in accordance with mechanical alignment (AAP), in accordance with kinematic alignment (PPNP), and in accordance with a refined mechanical alignment (TechMah).
Figure 64:
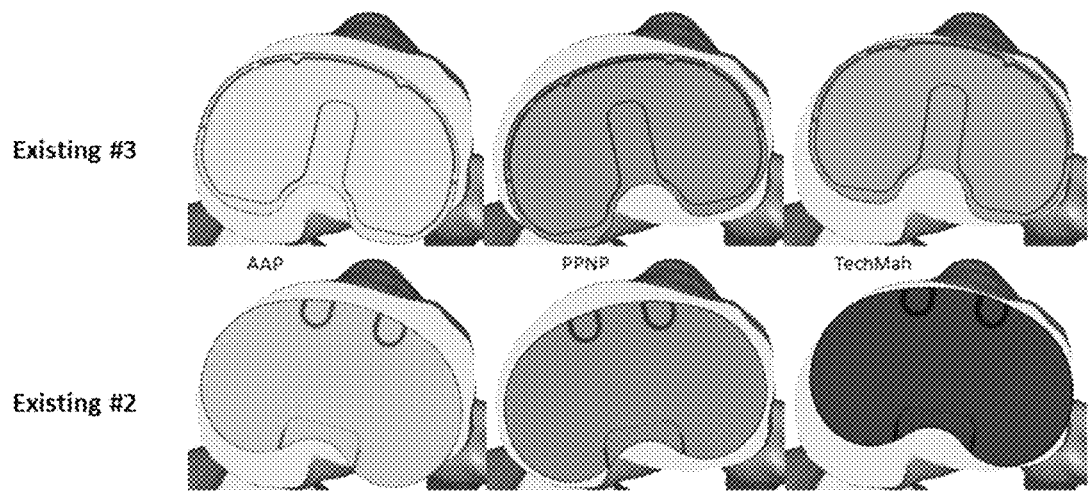
FIG. 64 includes a series of overhead views of a tibia having mounted thereto the second and third commercially available tibial tray in accordance with mechanical alignment (AAP), in accordance with kinematic alignment (PPNP), and in accordance with a refined mechanical alignment (TechMah).

Referring to FIGS. 59-64, a series of commercially available tibial trays are depicted via overhead views. In particular, in FIG. 59, these four commercially available tibial trays are identified as Existing #1, Existing #2, Existing #3, and Existing #4 and duplicated pictorially into three separate rows. The first row, identified as AAP, corresponds to the current mechanical alignment techniques utilized to align the tibial tray with respect to the femur and femoral component as shown in FIGS. 60, 63, and 64. The current mechanical alignment technique for all four existing tibial trays is depicted graphically in FIG. 60 with respect to a resected tibia. As can be seen in FIG. 60, using mechanical keys for alignment results in the implants being rotated toward the lateral side (beyond 12 o'clock in the clockwise direction). Conversely, the second row, identified as PPNP, corresponds to the same four commercially available tibial trays, but this time having the tibial trays implanted and aligned kinematically in accordance with the instant disclosure as shown in FIGS. 61, 63, and 64. As can be seen in FIG. 61, proper kinematic alignment of present day tibial trays results in the trays being rotated toward the medial side (beyond 12 o'clock in the counterclockwise direction). What is also apparent in FIG. 61 is that none of these four commercially available tibial trays are designed structurally to optimize kinematic alignment. Specifically, it can be seen that the current tibial trays, when kinematically aligned, result in significant overlap for the lateral anterior portion and posterior medial portion, whereas significant underlap is present in the posterior lateral portion and the anterior medial portion. Finally, the third row also corresponds to a mechanical alignment technique that attempts have the contour of the implant most closely approximate the contour of the resected tibia with an emphasis on anterior edge alignment, which is shown in FIGS. 62-64.

FIGS. 63 and 64 show individually the four exemplary current tibial trays) being aligned on a resected tibia, two using prior art techniques (AAP, TechMah) and the third (PPNP) using the techniques disclosed herein for kinematic alignment. These figures simply supplement FIGS. 60-62 that show the four current tibial trays superimposed onto the same resected tibia for illustrative purposes and further confirm that none of these four commercially available tibial trays is optimized for kinematic alignment given the overlap and underlap present when kinematically aligned.

Figure 65:
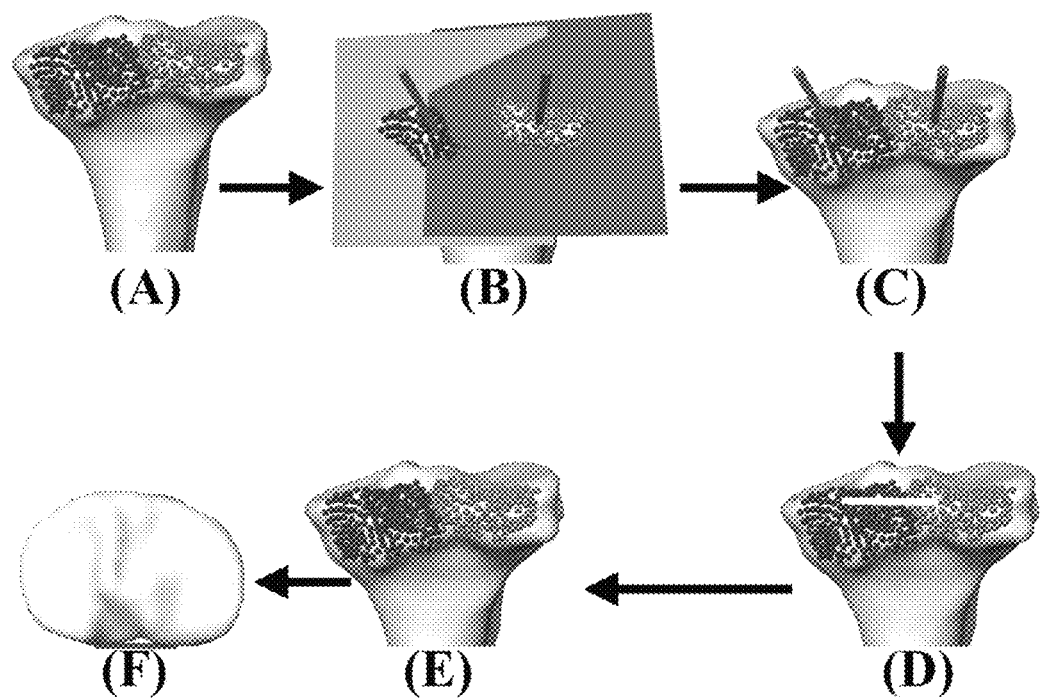
FIG. 65 is an exemplary process diagram for calculating a posterior tibial axis using a statistical atlas.
Figure 66:
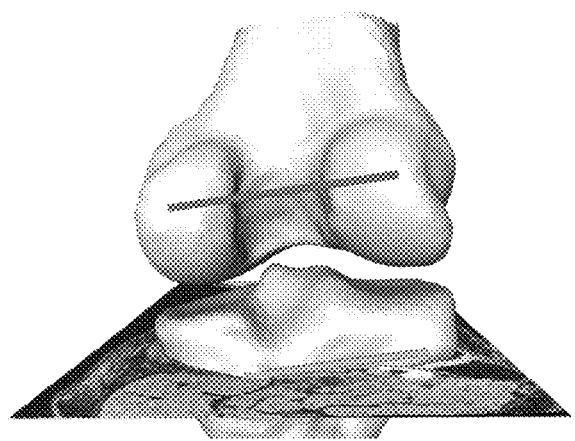
FIG. 66 is an elevated perspective view of a tibia and femur, along with an MRI image, confirming that the PCA for femur and tibia seldom lie along an image plane.
Figures 67A, 67B, 67C, 67D, 67E:
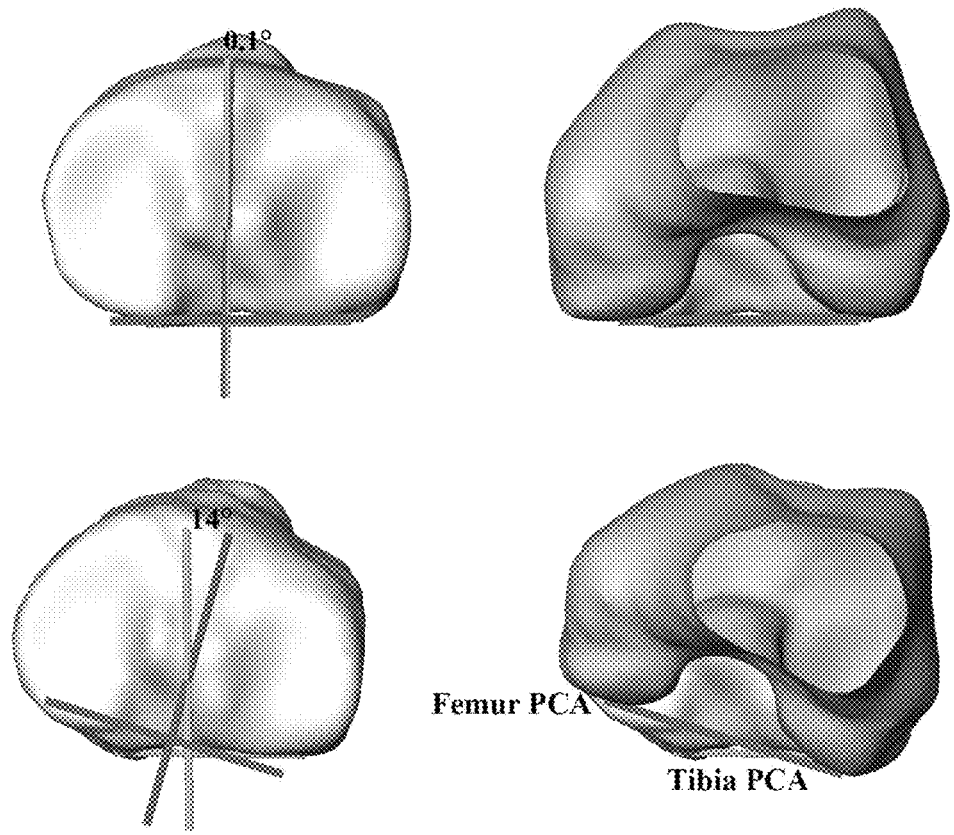
FIGS. 67A-67E includes overhead views of a tibia and of a femur on a tibia and how the PCA vary between the tibia and femur during rotation, along with a data set correlating the femoral PCA and Cobb axis.

Turning to FIG. 65, an exemplary process flow diagram is depicted for calculating the posterior condylar axis using a statistical atlas for a tibia. As an initial starting point, in step (A), a generic bone model of the tibia is propagated with the most posterior medial and lateral point on the surface of the tibia using the data from the statistical atlas. Afterwards, in step (B), a planar regression is performed on the propagated points to generate two planes, a first for the medial points and a second for the lateral points. Using each plane and the points, in step (C), a pair of axes are generated, one for the medial side and a second for the lateral side, that are normal to a respective plane at the center of the points. In step (D), a line is generated between the most posterior points on the medial and lateral side using the location of the axes generated in step (C). Thereafter, in step (E), the cross product of the line in step (D) and the axes generated in step (C) generates a new axis corresponding to the true posterior direction. Using this true posterior direction, the statistical atlas is searched for only the two most posterior points in this true posterior direction, which are then used to generate the posterior condylar axis for the tibia. This same process is applicable to calculating the posterior condylar axis for the femur. FIG. 66 simply confirms that 2D imaging slices are less accurate for determining the posterior condylar axis for the femur and tibia given that the axes are most often not parallel to the plane the image slice is taken from. And FIG. 67 confirms that the femoral posterior condylar axis reliably sets the rotation relative to the tibia.

Figure 104:
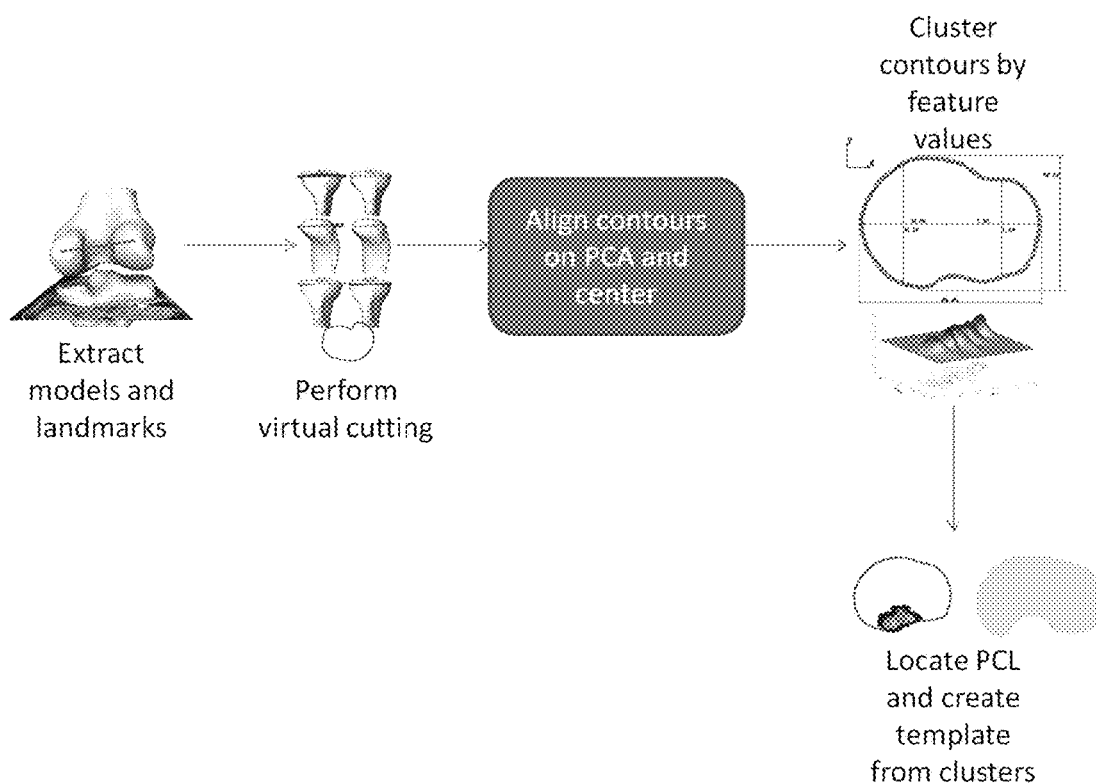
FIG. 104 is a graphical process flow diagram illustrating an exemplary process sequence for creation of a mass customized kinematic alignment guide or trial in accordance with the instant disclosure.

In view of the foregoing explanation, the following is an explanation of the process for generating a tibial, mass customized kinematic alignment guide. As depicted in FIG. 104, In exemplary form, a statistical atlas is utilized to calculate and extract various data that will be utilized as part of generating the mass customized kinematic alignment guide. This statistical atlas may be preexisting or may be newly generated. For purposes of explanation, construction of the statistical atlas follows.

The exemplary statistical atlas comprises a compilation of data from multiple subjects that involves the knee joint. By way of example, the statistical atlas may include various images and associated data derived from human knees such as, without limitation, X-ray images, CT images, MRI images, or other imaging technology. In the case of MRI images, the statistical atlas may include images of the soft tissue (e.g., cartilage) of the knee joint. By way of further example, it is presumed that the exemplary statistical atlas has been created from 100 MRI images and 66 CT images. These 166 images were then segmented to create 166 virtual joint models, which are also part of the statistical atlas.

Referring to FIGS. 69A-71C, the tibia from each virtual joint model within the statistical atlas is subjected to a resection process. As part of this resection process, each tibia has a plane applied thereto that simulates the bone cut a surgeon would make during a total knee arthroplasty (TKA) procedure to remove the proximal end of the tibia, thereby leaving a planar tibial end. As those skilled in the art are aware, the tibial bone cut carried out during a TKA is preferably made perpendicular to the sagittal plane. But absolute precision is not always possible, leading to tibial bone cuts that may be angled ±5 degrees from proximal to distal and ±5 degrees from medial to lateral, as well as having different heights ±1 millimeter from proximal to distal along the longitudinal length. Consequently, the resection process is carried out upon each tibia model taking into account a perfect bone cut (±0 degrees from proximal to distal, and ±0 degrees from medial to lateral) in order to make a resection cut, within 1 degree increments, for each combination between the ±15 degree deviation.

Figures 68A, 68B, 68C:
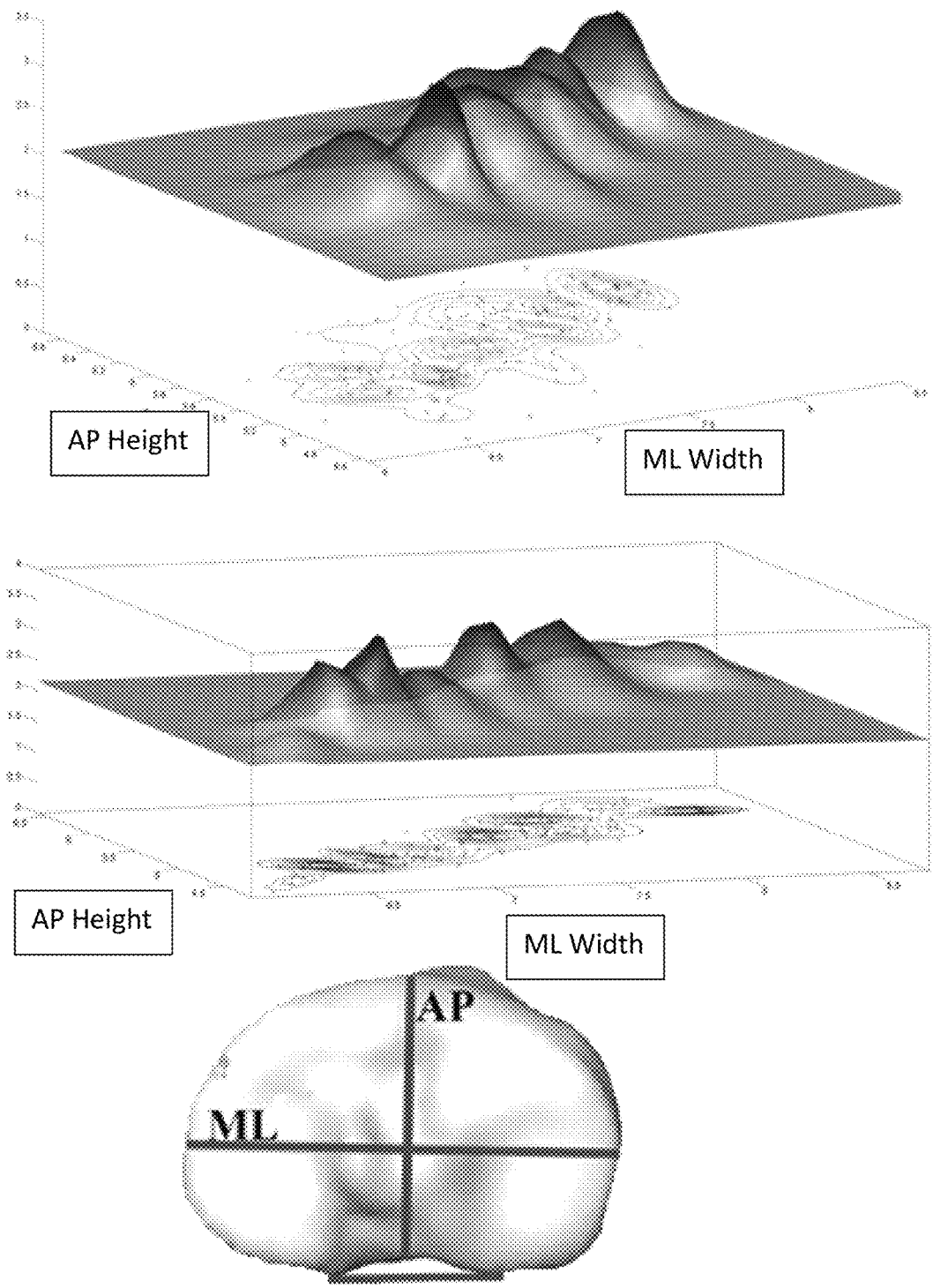
FIGS. 68A-68C include graphical depictions of clusters and groupings that result from clustering data, as well as how the AP and ML dimensions are calculated/measured.
Figures 69A, 69B, 69C:
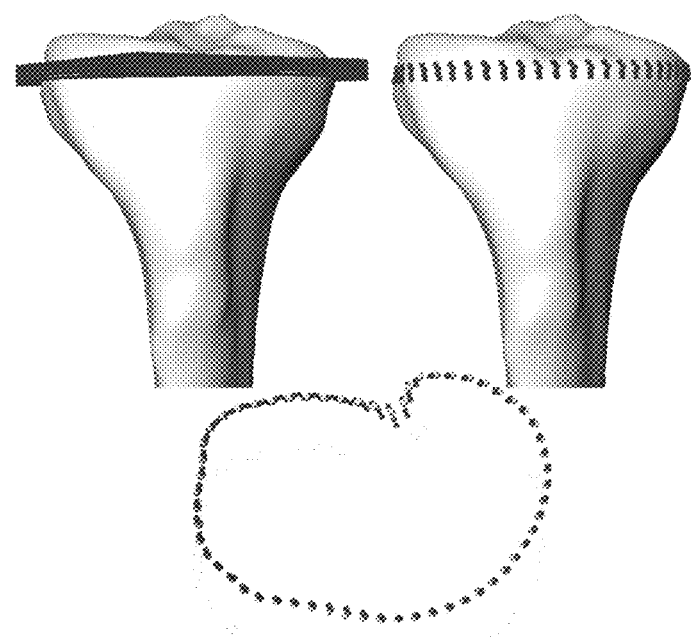
FIGS. 69A-69C include graphical depictions resection plane height variances and an average resection plane outline for a resected tibia.
Figures 70A, 70B, 70C:
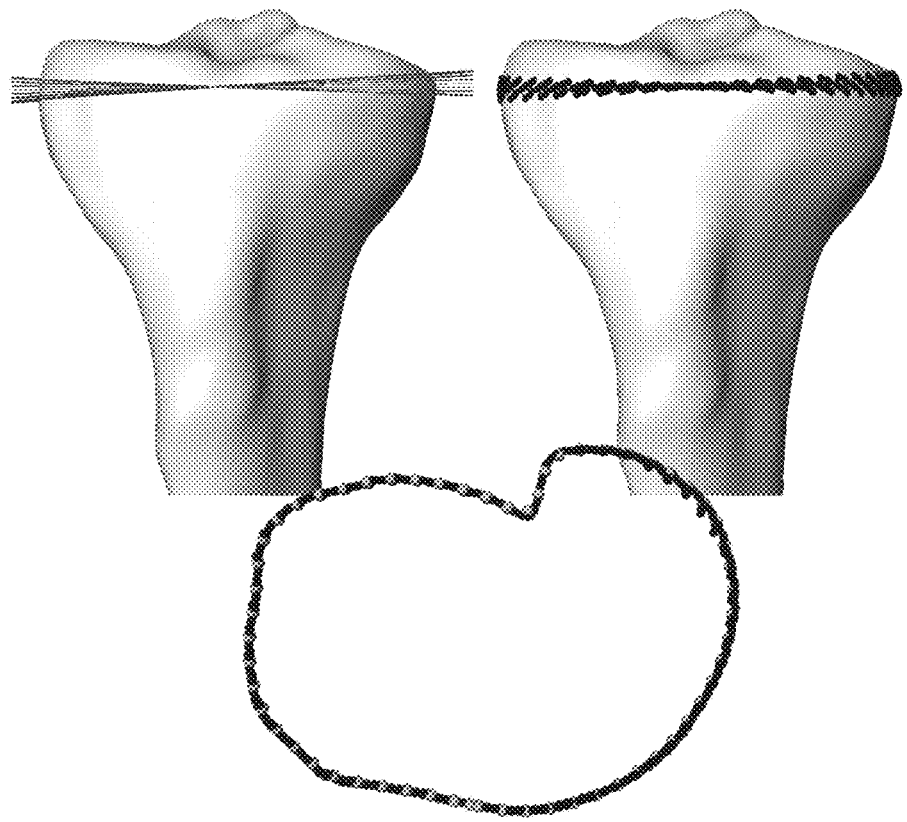
FIGS. 70A-70C include graphical depictions resection plane varus and valgus variances and an average resection plane outline for a resected tibia.
Figures 71A, 71B, 71C:
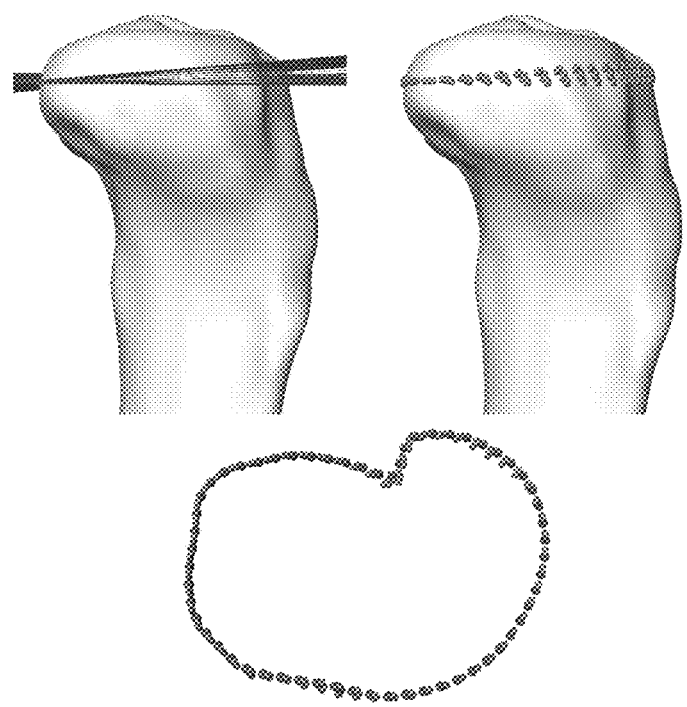
FIGS. 71A-71C include graphical depictions resection plane posterior slope variances and an average resection plane outline for a resected tibia.
Figures 72A, 72B:
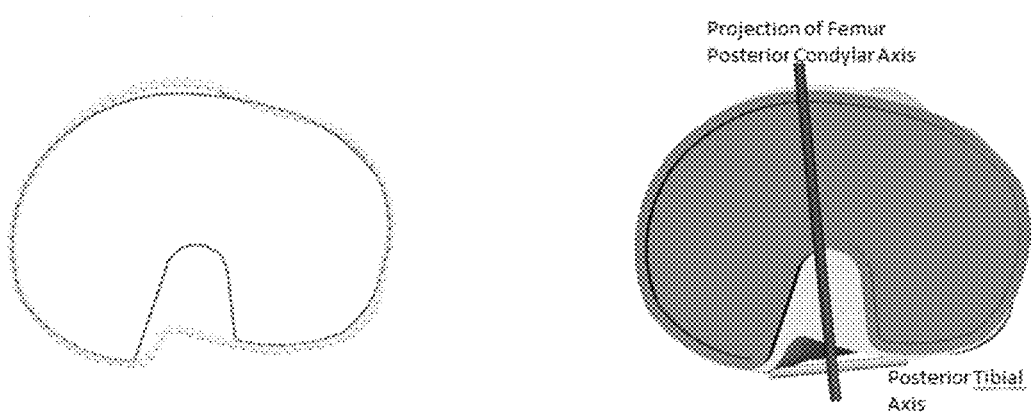
FIGS. 72A-72B include graphical depictions showing how an asymmetric tibial tray covers the resected tibia well, but is rotated incorrectly with respect to the projected femoral PCA.

Post resection, the contour (i.e., outline shape) of each resected tibia is determined to identify the outermost bounds. After the outermost bounds (i.e., outline shape) of the resected tibia have been determined, a number of calculations are undertaken with respect to these bounds to measure various aspect of the resected tibia. By way of example, and not limitation, the following eight measurements were computed for each resection: (1) M_ML, width of medial plateau; (2) M_AP, height of medial plateau; (3) L_ML, width of lateral plateau; (4) L_AP, height of lateral plateau; (5) BB_AP, overall anterior-posterior height; (6) BB_ML, overall medial-lateral width; (7) LLMLR, ratio of widths between the lateral and medial plateaus; and, (8) MLAPR, ratio of heights between the lateral and medial plateaus. In other words, each resected tibia included shape/outline data, as well as eight sets of measurement data. Referencing FIGS. 68A-68C, using this shape/outline data and the measurement data, a clustering operation was undertaken to establish size groupings across the population of the statistical atlas. For each size grouping, in this case six groupings, the average outline of the resected tibia was computed and utilized to form the shape outline of a tibial kinematic guide.

Referring to FIGS. 72A-74C, it should be noted that this shape outline may be further refined by using data from the statistical atlas to account for ligament retention. By way of example, where the posterior cruciate ligament is retained, the eventual orthopedic tibial implant should not impinge or obstruct the ligament. In order to account for one or more retained ligaments, the statistical atlas may include soft tissue data reflecting the placement of one or more ligaments with respect to the bones of the knee joint. By knowing the attachment locations on the bones of the knee joint where ligaments attach, the shape outline of the tibial kinematic guide can be altered to ensure the outline does not overlap or otherwise impinge upon one or more locations where a ligament will be retained as part of a TKA. The most common of these alterations is a sweeping curved notch cut into the shape outline to allow for retention of the posterior cruciate ligament.

In addition to utilizing the shape outline of the resected tibias from the statistical atlas, the statistical atlas is also utilized to calculate the kinematic axes for each joint model. These kinematic axes, as discussed previously, are transformed into data that accompanies each tibial bone model and the resulting bone model having been resected. The kinematic axes data for each resected bone model within a given size population are averaged and superimposed onto the shape outline of the average tibia for each size group. In particular, the sagittal kinematic axis of the femur from anterior to posterior is superimposed onto the tibial outline, in addition to the first transverse axis of the femur. Other axes may likewise be superimposed on to the average tibial shape outline for each size group. This superimposition is eventually utilized to form structural signs informing the surgeon as to the position of certain kinematic axes with respect to the kinematic guide that, when positioned correctly to align its outline with that of the actual resected tibia during TKA, indicates the position of certain kinematic axes with respect to the actual resected tibia.

Figures 73A, 73B:
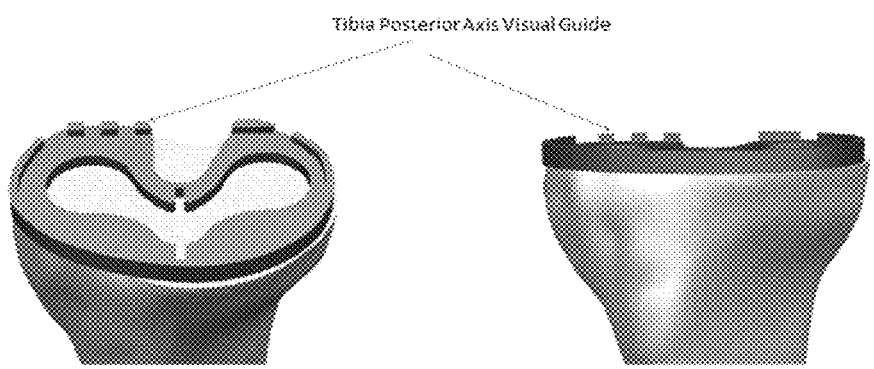
FIGS. 73A and 73B are multiple views of a first exemplary tibial tray trial fabricated in accordance with the instant disclosure.

Using the shape outline data and the superimposition data, a tibial guide may be constructed. A first exemplary mass customized kinematic guide for a tibial implant is shown in FIGS. 73A, 73B. This tibial guide is utilized by a surgeon to provide markings onto the resected tibia that will guide the surgeon to correctly place the tibial orthopedic implant. As can be seen, the guide includes a shape that closely approximates the outline of the resected tibia. In this fashion, the surgeon would position the guide on top of the resected tibia to most closely match the contour/outline of the guide with the outline of the resected femur, which denotes the proper position of the guide. The interior area of the guide includes a single through opening. This through opening includes a pair of three-sided rectangular cutouts extending in the posterior and anterior directions, that are near the middle from medial to lateral, that are longitudinally aligned with one another on opposing edges of the cutouts. These cutouts correspond to the femoral sagittal kinematic plane. It is envisioned that a surgeon would use a hammer and corresponding rectangular drive bit, where the drive bit was sized to fit within the bounds of the cutouts, to force the drive bit into the resected tibia and make a mark corresponding to the femoral sagittal plane. Alternatively, the surgeon may use a marker to denote the locations of the cutouts. In either instance, the guide may be thereafter removed to leave behind an indication of the location of the femoral sagittal kinematic plane.

This first exemplary mass customized kinematic guide also includes a contour on the posterior side to account for retention of the posterior cruciate ligament (PCL). In addition, the posterior portion of the guide includes a series of projections that lie on opposing sides of the PCL contour. These projections represent the location of the tibial PCA, which should be aligned with the most posterior points of the medial and lateral condyles. The surgeon may utilize these projections to ensure the guide is properly positioned with respect to the tibia.

Figures 74A, 74B, 74C:
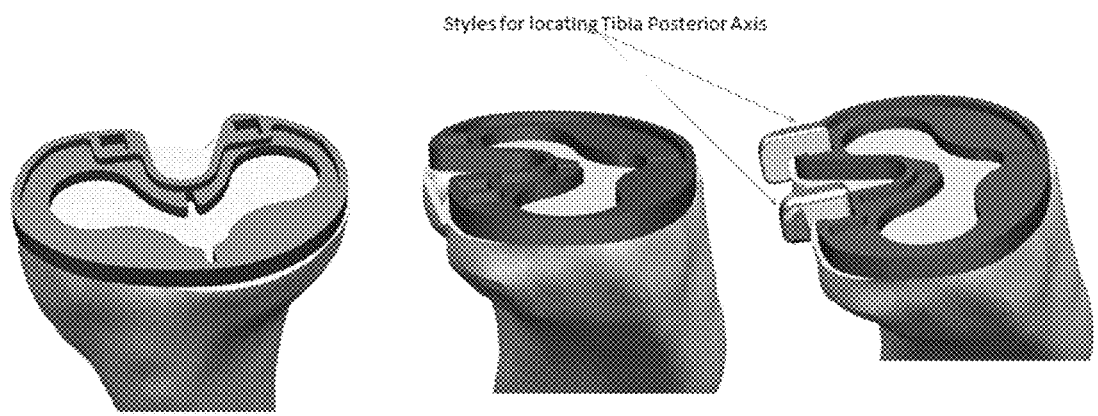
FIGS. 74A-74C are multiple views of a second exemplary tibial tray trial fabricated in accordance with the instant disclosure.

As shown in FIGS. 74A-74C, a first alternate exemplary mass customized kinematic guide for a tibial implant is identical to the first exemplary mass customized kinematic guide for a tibial implant, with the exception of the posterior projections. Instead of projections, the first alternate exemplary mass customized kinematic guide for a tibial implant includes a pair of rectangular recesses on opposing sides of the PCL contour. These recesses are sized to accept a corresponding style that extends posteriorly and distally from the guide. When inserted in to a corresponding recess, the styles cooperate to establish a posterior stop against which posterior portion of the resected tibia contacts to inhibit further anterior repositioning of the guide during the initial guide placement. In exemplary form, when the styles are inserted in to a corresponding recess, the surgeon uses the styles along with the outline shape of the guide to correctly position the guide with respect to the resected femur. Once correctly positioned, the surgeon may utilize the guide to make marks or attach fasteners to the top of the resected tibia to provide an indication of the placement of one or more axes of the femur.

Figure 84:
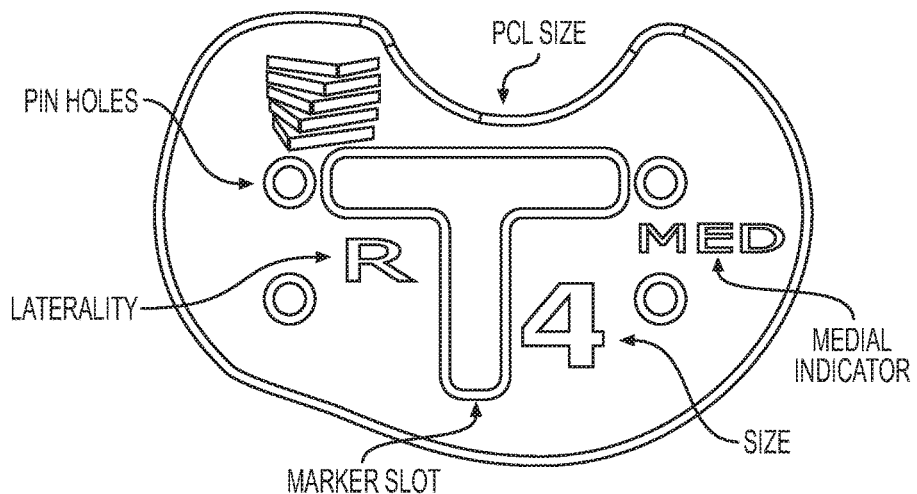
FIG. 84 is an overhead view of a first exemplary mass-customized tibial component kinematic placement guide fabricated in accordance with the instant disclosure.
Figure 85:
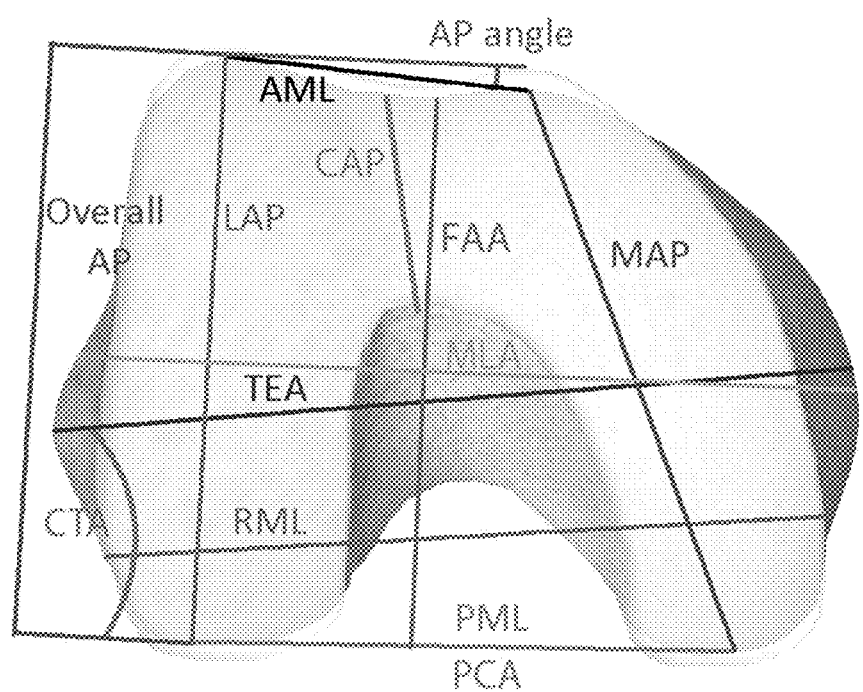
FIG. 85 is a picture of a distal femur showing the location of various measurements and landmarks.
Figure 86:
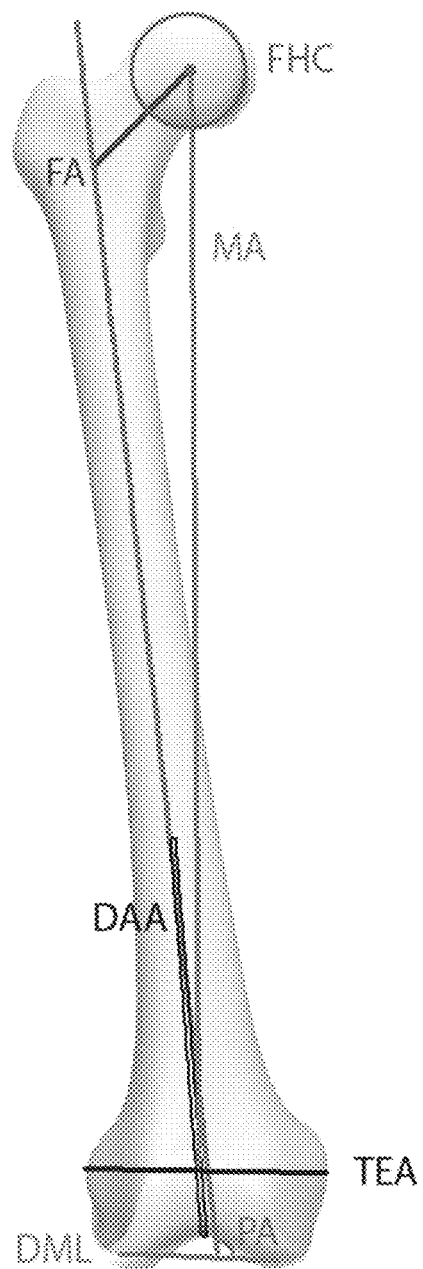
FIG. 86 is a picture of a profile view of a femur showing the location of various axes and landmarks.
Figure 87:
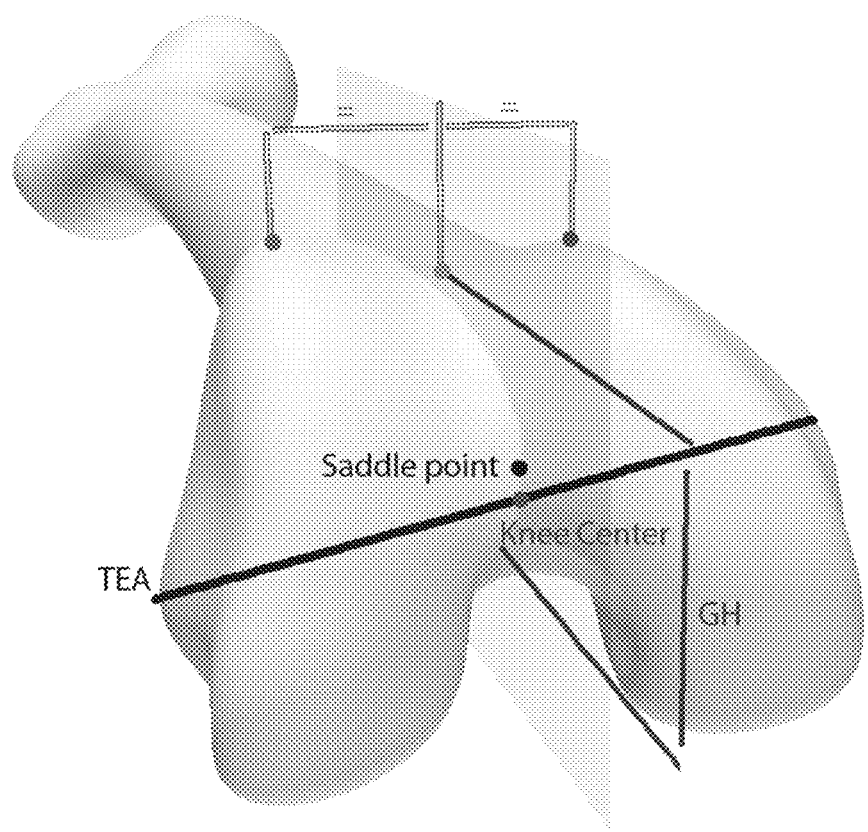
FIG. 87 is a picture of a distal femur showing the location of various axes, landmarks, and planes.
Figure 88:
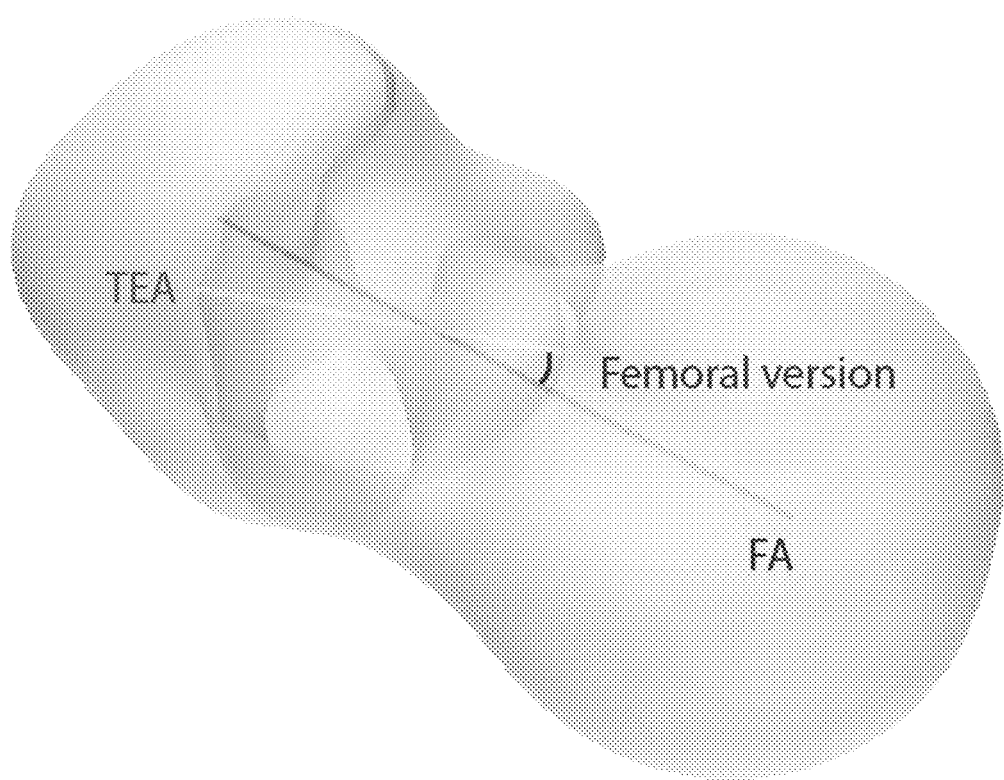
FIG. 88 is a picture of a proximal femur showing the location of various axes, landmarks, and planes.
Figure 89:
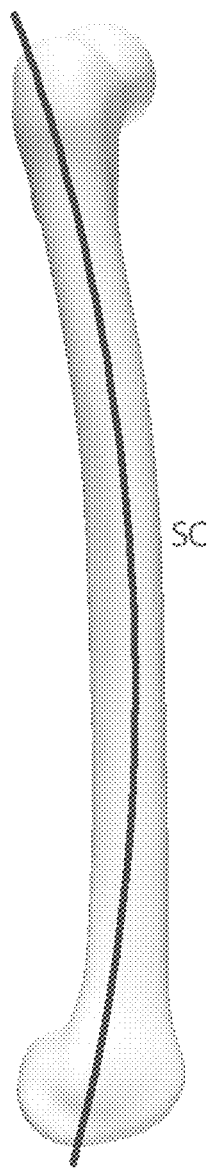
FIG. 89 is a picture of a profile view of a femur showing the natural longitudinal curvature.
Figure 90:
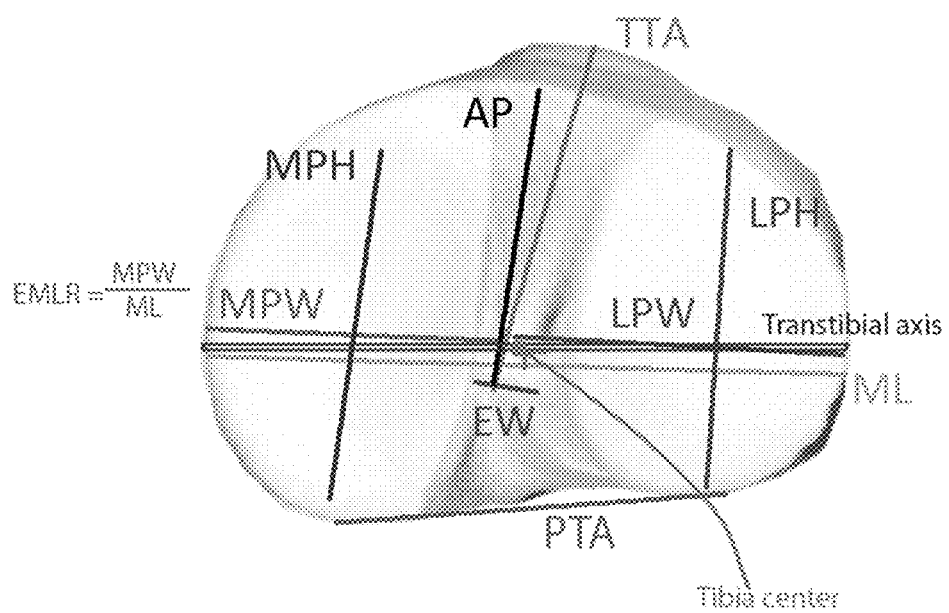
FIG. 90 is a picture of a proximal tibia showing the location of various axes, landmarks, and planes.
Figure 91:
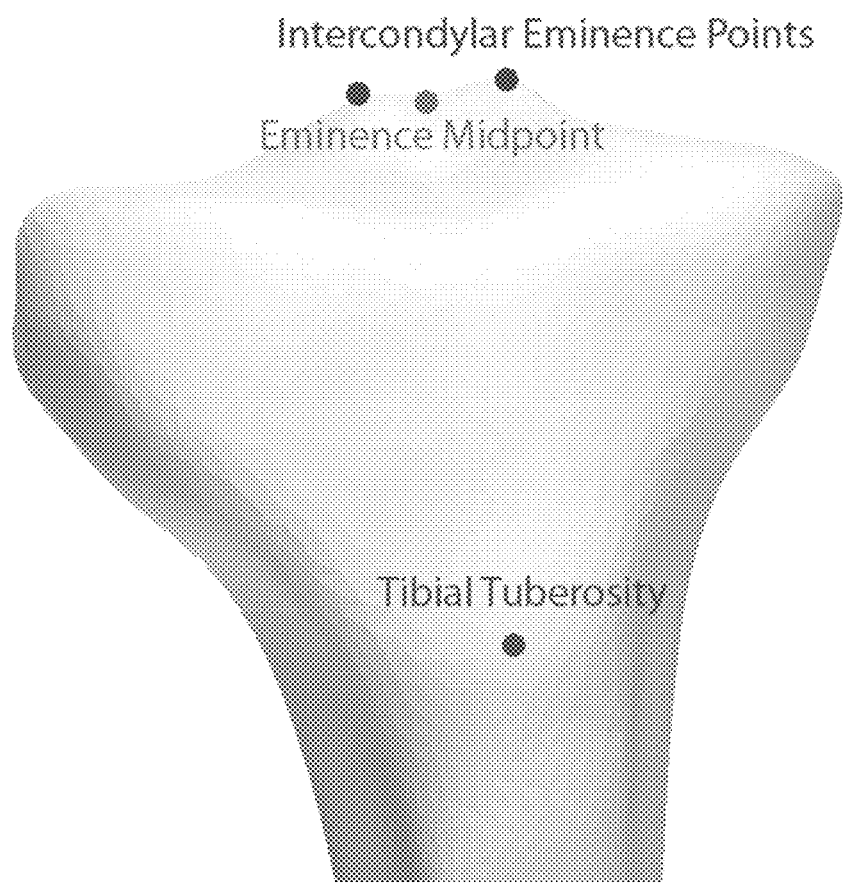
FIG. 91 is a picture of a profile view of a proximal tibia showing the location of various landmarks.
Figure 92:
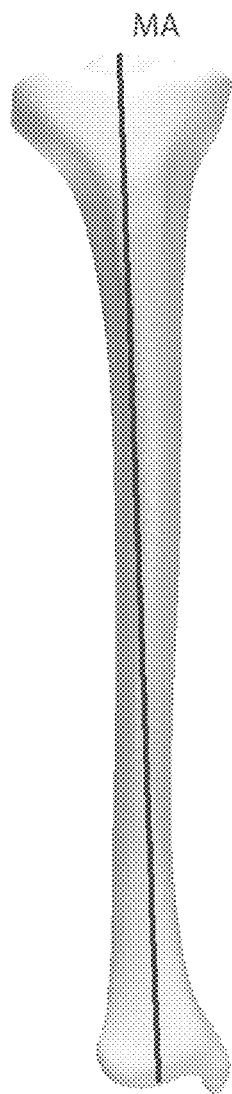
FIG. 92 is a picture of a profile tibia showing the mechanical axis of the tibia.
Figures 95A, 95B:
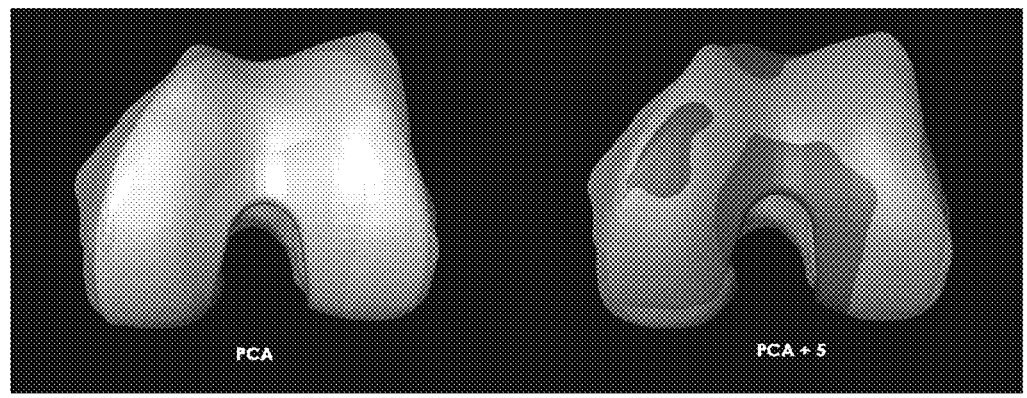
FIGS. 95A and 95B are images of the distal end of a femoral model showing how rotational changes with respect to the interface between the tibia and femur effect the shape of the trochlear groove.

Referring to FIG. 84, again using the shape outline data and the superimposition data, a tibial guide may be constructed. This second exemplary mass customized kinematic guide for a tibial implant is also intended to be utilized by a surgeon to provide markings (and/or attach pins or other fasteners) onto the resected tibia that will guide the surgeon to correctly place the tibial orthopedic implant. As can be seen, the guide includes a shape that closely approximates the outline of the resected tibia. In this fashion, the surgeon would position the guide on top of the resected tibia to most closely match the contour/outline of the guide with the outline of the resected femur, which denotes the proper position of the guide. The interior area of the guide includes T-shaped through opening along with four circular openings, two on opposing sides of the T-shaped opening. This T-shaped through opening includes an elongated media to lateral section (top, horizontal portion of the T), as well as an elongated posterior to anterior section (vertical portion of the T). The elongated medial to lateral section of the T-shaped opening corresponds to an axis in parallel with the femur PCA, while the elongated posterior to anterior section of the T-shaped opening corresponds to the femoral sagittal kinematic plane. The four circular openings are sized to receive pins or other fasteners that are mounted to the resected tibia and retained after the tibial guide is removed from the resected tibia.

In addition to the openings formed through this second exemplary mass customized kinematic guide, the guide also includes various indicia. In particular, the face of the guide opposite the resected tibia includes a "MED" indicia indicating to a surgeon that this side of the guide should be aligned with the medial portion of the tibia. In order for the surgeon to quickly know whether the guide is for the right tibia or the left tibia, the face includes a "R" indicia indicating that this guide is for use with the right tibia. In cases where the guide is fabricated to correspond to the left tibia, this "R" would be replaced with an "L." Finally, the face of the guide also includes a size indicia, in this case a "4" indicating to the surgeon that this guide is a size four. Should the initial selection of the guide be too large or small, the surgeon can quickly request a smaller or larger size guide and operating room assistants can quickly discern the size of the guide using this size reference indicia. And similar to the first exemplary mass customized kinematic guide, this second exemplary mass customized kinematic guide also includes a contour on the posterior side to account for retention of the posterior cruciate ligament (PCL).

Referring to FIGS. 77, 78A, 78B, and 83, again using the shape outline data and the superimposition data, a further tibial guide may be constructed. This third exemplary mass customized kinematic guide for a tibial implant is also intended to be utilized by a surgeon to provide markings (and/or attach pins or other fasteners) onto the resected tibia that will guide the surgeon to correctly place the tibial orthopedic implant. As can be seen, the guide includes a shape that closely approximates the outline of the resected tibia. In this fashion, the surgeon would position the guide on top of the resected tibia to most closely match the contour/outline of the guide with the outline of the resected femur, which denotes the proper position of the guide. The interior area of the guide includes single through opening along with along with a pair of cutouts. The single through opening includes an enlarged anterior opening to accommodate tibial broach throughput. Extending off of this enlarged opening is a first pair of cutouts extending in the medial and lateral directions, terminating in circular openings. The circular openings are sized and configured to receive pins or other fasteners that are mounted to the resected tibia and retained after the guide is removed from the resected tibia. The dominant length of these first cutouts are delineated by parallel walls that cooperate to establish an axis that is parallel with the femoral PCA. A second set of cutouts extends in the posterior and anterior directions. These cutouts are representative of the location of the femoral sagittal kinematic plane. Finally, extending posteriorly and in the medial and lateral directions are a third set of cutouts that provide an area for larger fasteners or larger markings to be made onto the resected tibia.

Similar to the first and second exemplary mass customized kinematic guides, this third exemplary mass customized kinematic guide also includes a contour on the posterior side to account for retention of the posterior cruciate ligament (PCL). A fourth set of cutouts is formed on opposing sides of this posterior contour. These fourth cutouts extend in the medial and lateral directions, terminating in circular openings. The circular openings are sized and configured to receive pins or other fasteners that are mounted to the resected tibia and retained after the guide is removed from the resected tibia. The dominant length of these fourth cutouts are delineated by parallel walls that cooperate to establish an axis that is parallel with the femoral PCA.

In addition to the openings formed through this third exemplary mass customized kinematic guide, the guide also includes various indicia. In particular, the face of the guide opposite the resected tibia includes a "MED" indicia indicating to a surgeon that this side of the guide should be aligned with the medial portion of the tibia. In order for the surgeon to quickly know whether the guide is for the right tibia or the left tibia, the face includes a "R" indicia indicating that this guide is for use with the right tibia. In cases where the guide is fabricated to correspond to the left tibia, this "R" would be replaced with an "L." Finally, the face of the guide also includes a size indicia, in this case a "4" indicating to the surgeon that this guide is a size four. Should the initial selection of the guide be too large or small, the surgeon can quickly request a smaller or larger size guide and operating room assistants can quickly discern the size of the guide using this size reference indicia.

While the foregoing explanation has been directed to processes and generation of mass customized tibial kinematic guides, it should be noted that patient-specific guides can be fabricated in accordance with the instant disclosure. Consequently, the following is an exemplary explanation of the process and resulting fabrication of a patient specific tibial kinematic guide.

Figure 75:
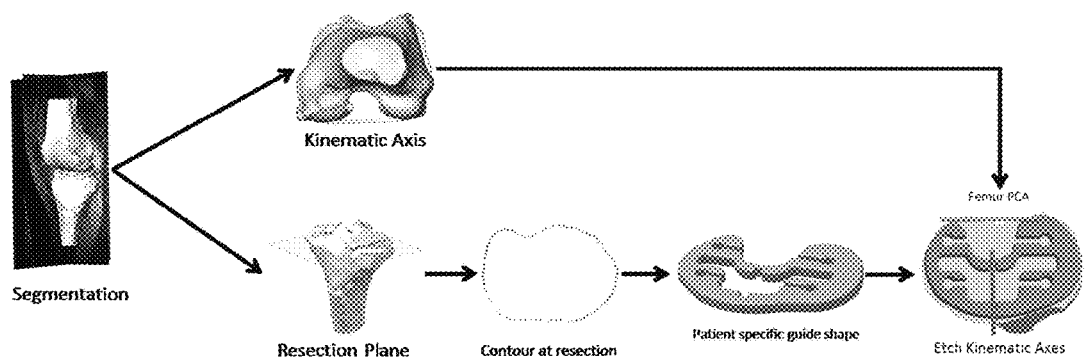
FIG. 75 is a graphical depiction of a process flow for patient specific kinematic guide fabrication.
Figure 76:
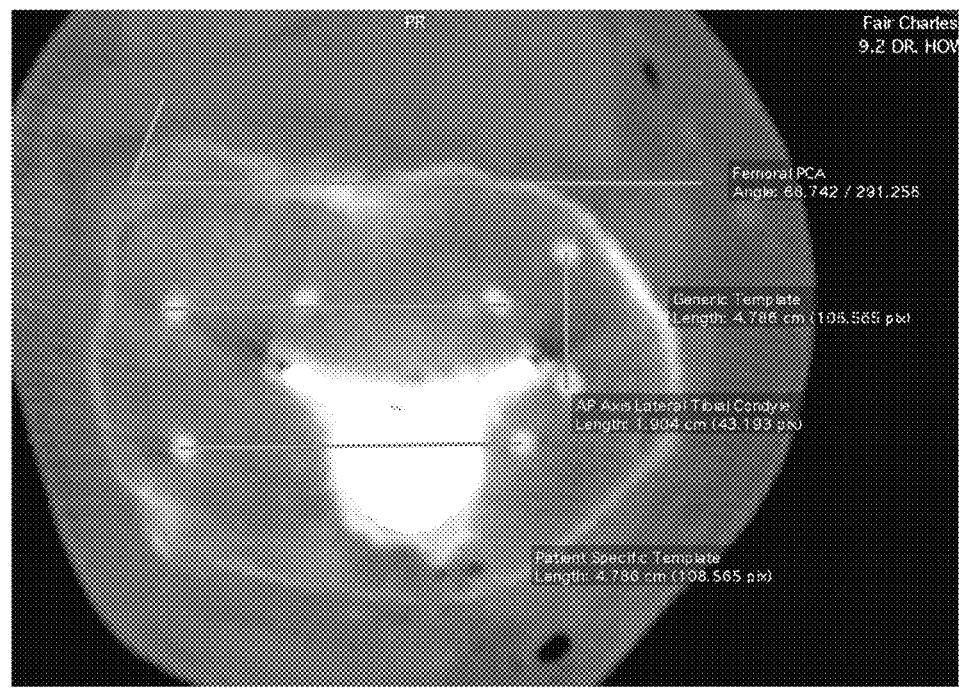
FIG. 76 is an image of a resected tibia showing consistency between measured and calculated kinematic axes.
Figure 77:
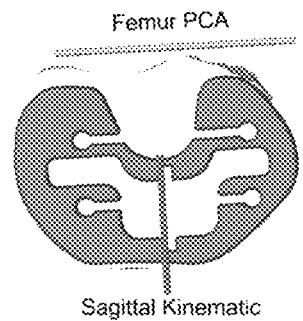
FIG. 77 is an overhead view of a mass customized kinematic alignment guide for a resected tibia fabricated in accordance with the instant disclosure.
Figures 78A, 78B:
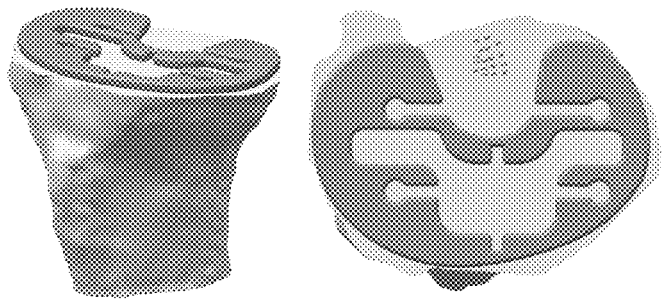
FIGS. 78A and 78B are multiple views of the mass customized kinematic alignment guide of FIG. 77 that account for retention of the posterior cruciate ligament during TKA.
Figures 79A, 79B:
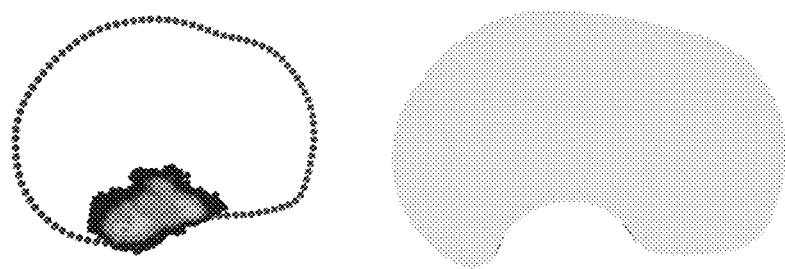
FIGS. 79A and 79B are multiple views, one showing the outline of a resected tibia and using the statistical atlas to determine the location of the posterior cruciate ligament, as well as a second showing a possible design for a kinematic friendly tibial tray that does not impinge upon the posterior cruciate ligament.
Figure 80:
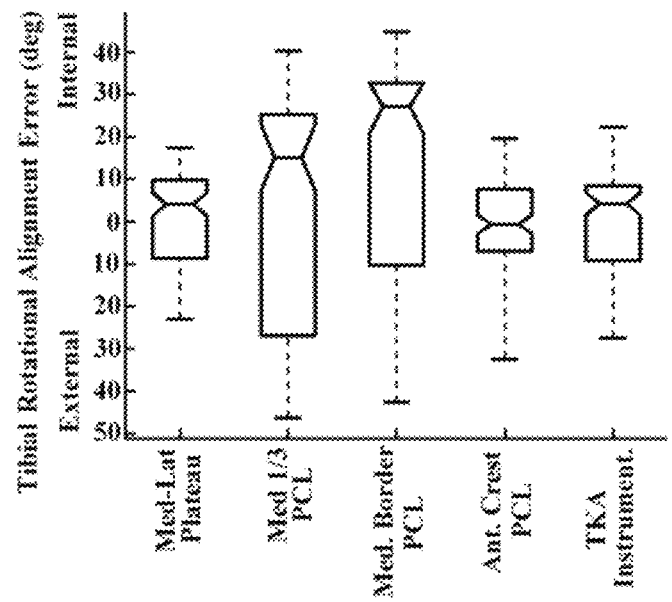
FIG. 80 is a graph showing high variability of setting tibial rotation using present day method (non-kinematic methods).
Figure 81:
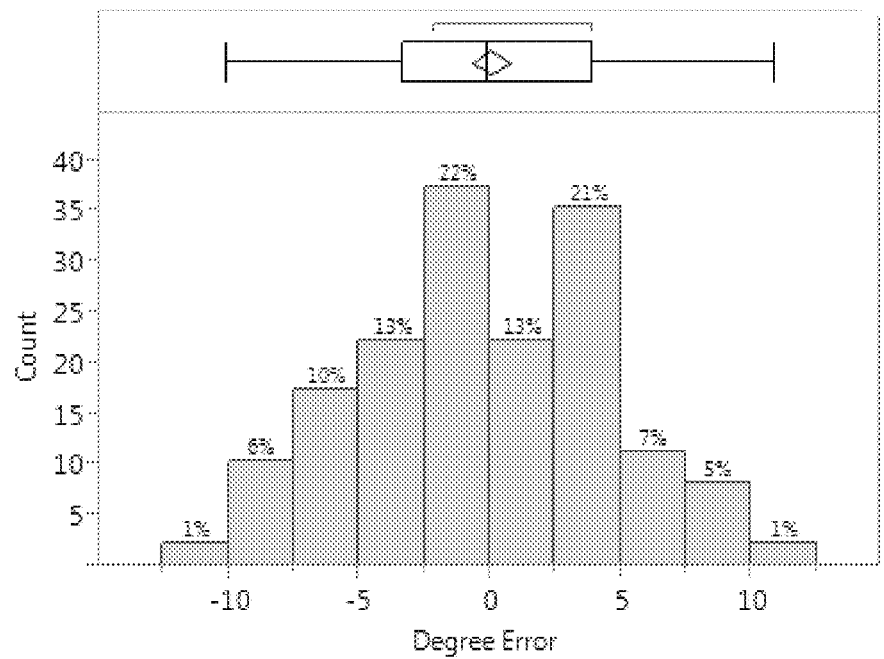
FIG. 81 is a graph showing placement error of kinematic placements using a guide in accordance with the instant disclosure, as validated through a software study.
Figure 82:
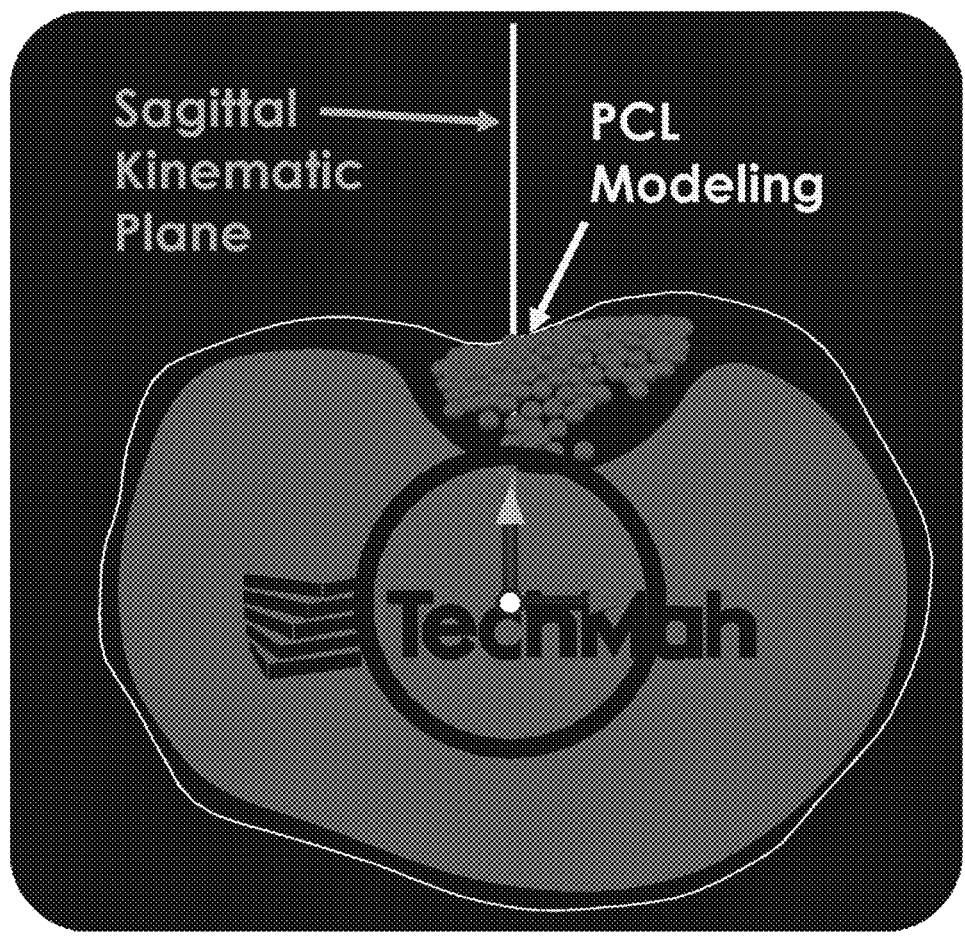
FIG. 82 is a screen capture during the software validation study graphically depicted in FIG. 81.
Figure 83:
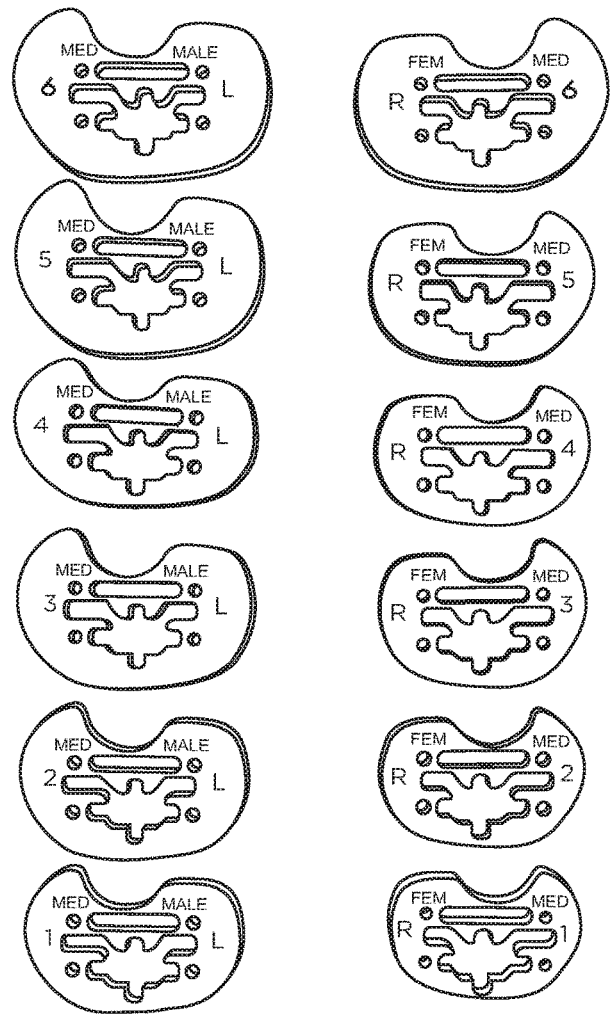
FIG. 83 is a picture of a plurality of mass-customized tibial component kinematic placement guides fabricated in accordance with the instant disclosure, in various sizes.

Referring to FIG. 75, the following is an explanation of the process for generating a tibial, patient-specific kinematic alignment guide. In exemplary form, images of the patient knee joint are taken from one or more imaging modalities including, without limitation, X-ray images, CT images, ultrasound, and MRI images. In the case of MRI images, the patient knee joint images may include images of the soft tissue (e.g., cartilage) of the knee joint. These patient images are then segmented to create a patient-specific virtual joint model using a software program. Those skilled in the art are familiar with segmentation and utilizing 2D images to form a virtual 3D model.

The tibia from the patient-specific virtual joint model is subjected to a resection process using a software resection algorithm. As part of this resection process, the tibia has a plane applied thereto that simulates the bone cut a surgeon would make during a total knee arthroplasty (TKA) procedure to remove the proximal end of the tibia, thereby leaving a planar tibial end. As those skilled in the art are aware, the tibial bone cut carried out during a TKA is preferably made perpendicular to the sagittal plane. But absolute precision is not always possible, leading to tibial bone cuts that may be angled ±5 degrees from proximal to distal and ±5 degrees from medial to lateral, as well as having different heights ±1 millimeter from proximal to distal along the longitudinal length. Consequently, the resection process is carried out upon the tibia model taking into account a perfect bone cut (±0 degrees from proximal to distal, and ±0 degrees from medial to lateral) in order to make a resection cut, within 1 degree increments, for each combination between the ±5 degree deviation.

Post resection, the contour (i.e., outline shape) of the resected tibia is determined to identify the outermost bounds using a software contour algorithm. After the outermost bounds (i.e., outline shape) of the resected tibia have been determined, a number of calculations are undertaken with respect to these bounds to measure various aspect of the resected tibia. By way of example, and not limitation, the following eight measurements were computed for each resection: (1) M_ML, width of medial plateau; (2) M_AP, height of medial plateau; (3) L_ML, width of lateral plateau; (4) L_AP, height of lateral plateau; (5) BB_AP, overall anterior-posterior height; (6) BB_ML, overall medial-lateral width; (7) LLMLR, ratio of widths between the lateral and medial plateaus; and, (8) MLAPR, ratio of heights between the lateral and medial plateaus. In other words, each resected tibia includes shape/outline data, as well as eight sets of measurement data. Using this shape/outline data and the measurement data, the size and outline of the resected tibia is computed and utilized to form the shape outline of the patient-specific tibial kinematic guide.

It should be noted that this shape outline may be further refined by using data from the patient-specific images to account for ligament retention. By way of example, where the posterior cruciate ligament is retained, the orthopedic tibial implant should not impinge or obstruct the ligament. In order to account for one or more retained ligaments, the patient-specific virtual model of the knee joint includes one or more ligaments with respect to the bones of the knee joint. By knowing the attachment locations on the bones of the knee joint where ligaments attach, the shape outline of the patient-specific tibial kinematic guide can be altered to ensure the outline does not overlap or otherwise impinge upon one or more locations where a ligament will be retained as part of a TKA. The most common of these alterations is a sweeping curved notch cut into the shape outline to allow for retention of the posterior cruciate ligament.

In addition to generating the shape and size of the patient-specific kinematic guide, the computer program also calculates the kinematic axes for the patient-specific joint model using one or more axis/axes algorithms. These calculated kinematic axes, as discussed previously, are transformed into data that accompanies the tibial bone model and the resulting tibial bone model post resection. The kinematic axes data for the resected tibial bone model is superimposed onto the shape outline of the bone model. In particular, the sagittal kinematic axis of the femur from anterior to posterior is superimposed onto the shape outline, in addition to the first transverse axis of the femur. Other axes may likewise be superimposed onto the tibial shape outline for. This superimposition is eventually utilized to form structural signs informing the surgeon as to the position of certain kinematic axes with respect to the kinematic guide that, when positioned correctly to align its outline with that of the actual resected tibia during TKA, indicates the position of certain kinematic axes with respect to the actual resected tibia.

Figure 105:
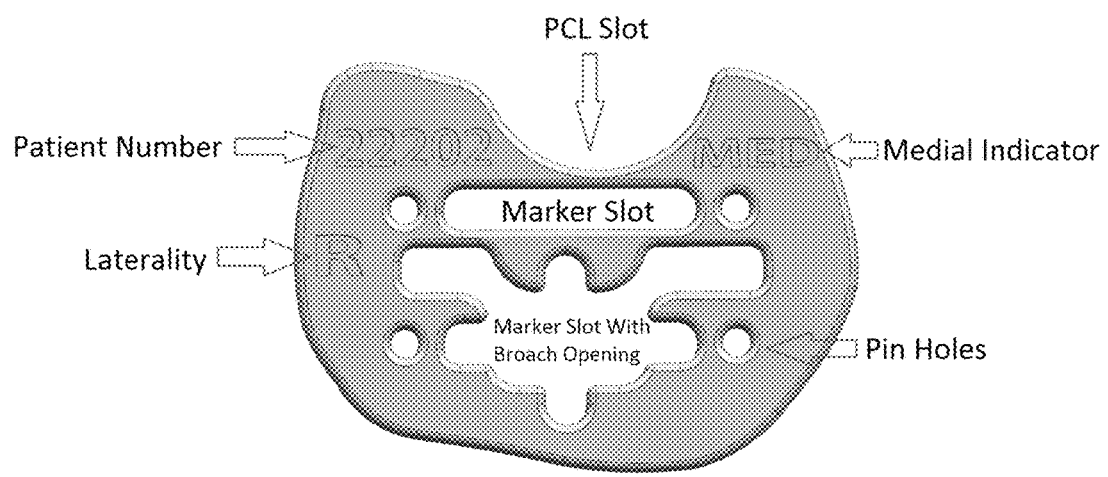
FIG. 105 is an overhead view of a first exemplary patient-specific kinematic alignment guide for use with a resected tibia.
Figures 106A, 106B:
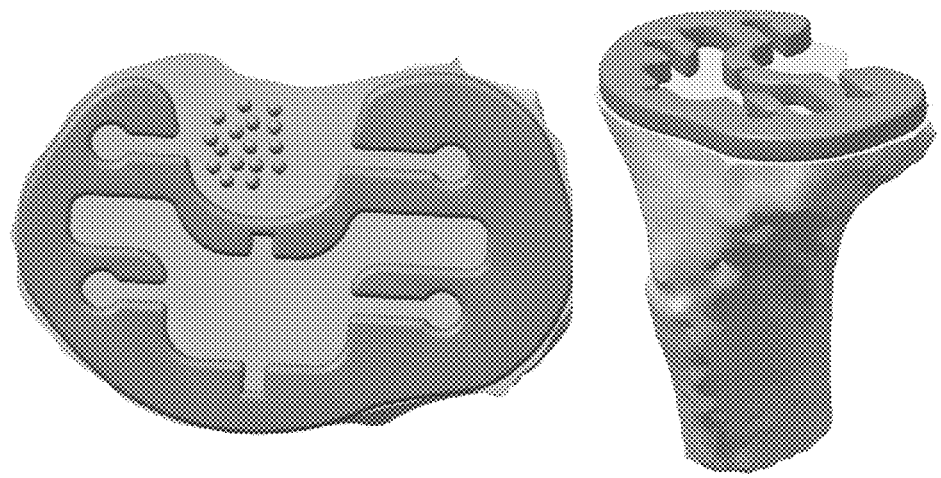
FIGS. 106A and 106B are various views of a second exemplary patient-specific kinematic alignment guide for use with a resected tibia showing the placement of the guide with respect to the tibia and with respect to the posterior cruciate ligament.

Using the shape outline data and the superimposition data, a patient-specific tibial guide may be constructed. A first exemplary patient-specific kinematic guide for a tibial implant is shown in FIGS. 105, 106A, and 106B. This tibial guide is utilized by a surgeon to provide markings onto the resected tibia that will guide the surgeon to correctly place the tibial orthopedic implant. As can be seen, the guide includes a shape that precisely mirrors the outline of the resected tibia. In this fashion, the surgeon would position the guide on top of the resected tibia to most closely match the contour/outline of the guide with the outline of the resected femur, which denotes the proper position of the guide. The interior area of the guide includes a single through opening. This through opening includes a pair of three-sided rectangular cutouts extending in the posterior and anterior directions, that are near the middle from medial to lateral, that are longitudinally aligned with one another on opposing edges of the cutouts. These cutouts correspond to the femoral sagittal kinematic plane. It is envisioned that a surgeon would use a hammer and corresponding rectangular drive bit, where the drive bit was sized to fit within the bounds of the cutouts, to force the drive bit into the resected tibia and make a mark corresponding to the femoral sagittal plane. Alternatively, the surgeon may use a marker to denote the locations of the cutouts. In either instance, the guide may be thereafter removed to leave behind an indication of the location of the femoral sagittal kinematic plane.

This first exemplary patient-specific kinematic guide also includes a contour on the posterior side to account for retention of the posterior cruciate ligament (PCL). In addition, the posterior portion of the guide includes a series of projections that lie on opposing sides of the PCL contour. These projections represent the location of the tibial PCA, which should be aligned with the most posterior points of the medial and lateral condyles. The surgeon may utilize these projections to ensure the guide is properly positioned with respect to the tibia.

As shown in FIG. 74, a first alternate exemplary patient-specific kinematic guide for a tibial implant is identical to the first exemplary patient-specific kinematic guide for a tibial implant, with the exception of the posterior projections. Instead of projections, the first alternate exemplary patient-specific kinematic guide for a tibial implant includes a pair of rectangular recesses on opposing sides of the PCL contour. These recesses are sized to accept a corresponding style that extends posteriorly and distally from the guide. When inserted in to a corresponding recess, the styles cooperate to establish a posterior stop against which posterior portion of the resected tibia contacts to inhibit further anterior repositioning of the guide during the initial guide placement. In exemplary form, when the styles are inserted in to a corresponding recess, the surgeon uses the styles along with the outline shape of the guide to correctly position the guide with respect to the resected femur. Once correctly positioned, the surgeon may utilize the guide to make marks or attach fasteners to the top of the resected tibia to provide an indication of the placement of one or more axes of the femur.

Referring to FIG. 84, again using the shape outline data and the superimposition data, a tibial guide may be constructed. This second exemplary patient-specific kinematic guide for a tibial implant is also intended to be utilized by a surgeon to provide markings (and/or attach pins or other fasteners) onto the resected tibia that will guide the surgeon to correctly place the tibial orthopedic implant. As can be seen, the guide includes a shape that mirrors the outline of the resected tibia. In this fashion, the surgeon would position the guide on top of the resected tibia to most closely match the contour/outline of the guide with the outline of the resected femur, which denotes the proper position of the guide. The interior area of the guide includes T-shaped through opening along with four circular openings, two on opposing sides of the T-shaped opening. This T-shaped through opening includes an elongated media to lateral section (top, horizontal portion of the T), as well as an elongated posterior to anterior section (vertical portion of the T). The elongated medial to lateral section of the T-shaped opening corresponds to an axis in parallel with the femur PCA, while the elongated posterior to anterior section of the T-shaped opening corresponds to the femoral sagittal kinematic plane. The four circular openings are sized to receive pins or other fasteners that are mounted to the resected tibia and retained after the tibial guide is removed from the resected tibia.

In addition to the openings formed through this second exemplary patient-specific kinematic guide, the guide also includes various indicia. In particular, the face of the guide opposite the resected tibia includes a "MED" indicia indicating to a surgeon that this side of the guide should be aligned with the medial portion of the tibia. In order for the surgeon to quickly know whether the guide is for the right tibia or the left tibia, the face includes a "R" indicia indicating that this guide is for use with the right tibia. In cases where the guide is fabricated to correspond to the left tibia, this "R" would be replaced with an "L." Finally, the face of the guide also includes a size indicia, in this case a "4" indicating to the surgeon that this guide is a size four.

Should the initial selection of the guide be too large or small, the surgeon can quickly request a smaller or larger size guide and operating room assistants can quickly discern the size of the guide using this size reference indicia. And similar to the first exemplary patient-specific kinematic guide, this second exemplary patient-specific kinematic guide also includes a contour on the posterior side to account for retention of the posterior cruciate ligament (PCL).

Referring to FIGS. 77, 78A, 78B, and 83, again using the shape outline data and the superimposition data, a further tibial guide may be constructed. This third exemplary patient-specific kinematic guide for a tibial implant is also intended to be utilized by a surgeon to provide markings (and/or attach pins or other fasteners) onto the resected tibia that will guide the surgeon to correctly place the tibial orthopedic implant. As can be seen, the guide includes a shape that closely approximates the outline of the resected tibia. In this fashion, the surgeon would position the guide on top of the resected tibia to most closely match the contour/outline of the guide with the outline of the resected femur, which denotes the proper position of the guide. The interior area of the guide includes single through opening along with along with a pair of cutouts. The single through opening includes an enlarged anterior opening to accommodate tibial broach throughput. Extending off of this enlarged opening is a first pair of cutouts extending in the medial and lateral directions, terminating in circular openings. The circular openings are sized and configured to receive pins or other fasteners that are mounted to the resected tibia and retained after the guide is removed from the resected tibia. The dominant length of these first cutouts are delineated by parallel walls that cooperate to establish an axis that is parallel with the femoral PCA. A second set of cutouts extends in the posterior and anterior directions. These cutouts are representative of the location of the femoral sagittal kinematic plane. Finally, extending posteriorly and in the medial and lateral directions are a third set of cutouts that provide an area for larger fasteners or larger markings to be made onto the resected tibia.

Similar to the first and second exemplary patient-specific kinematic guides, this third exemplary patient-specific kinematic guide also includes a contour on the posterior side to account for retention of the posterior cruciate ligament (PCL). A fourth set of cutouts is formed on opposing sides of this posterior contour. These fourth cutouts extend in the medial and lateral directions, terminating in circular openings. The circular openings are sized and configured to receive pins or other fasteners that are mounted to the resected tibia and retained after the guide is removed from the resected tibia. The dominant length of these fourth cutouts are delineated by parallel walls that cooperate to establish an axis that is parallel with the femoral PCA.

In addition to the openings formed through this third exemplary patient-specific kinematic guide, the guide also includes various indicia. In particular, the face of the guide opposite the resected tibia includes a "MED" indicia indicating to a surgeon that this side of the guide should be aligned with the medial portion of the tibia. In order for the surgeon to quickly know whether the guide is for the right tibia or the left tibia, the face includes a "R" indicia indicating that this guide is for use with the right tibia. In cases where the guide is fabricated to correspond to the left tibia, this "R" would be replaced with an "L." Finally, the face of the guide also includes a patient indicia, in this case a last name or abbreviated name indicating to the surgeon that this guide is for a particular patient in order to distinguish one patient-specific guide from another patient-specific guide.

In addition to tibial guides, the present disclosure also provides for tibial orthopedic trials that are mass customized and patient-specific. FIGS. 73 and 74 show exemplary tibial orthopedic trials. It should be understood that the foregoing guides may be modified to include a flange around the periphery of the footprint that would operate to transform the guide into a tibial tray trial. In this fashion, the trial would be shaped to accept a tibial tray trial insert in order to test fit the size and location of the trial orthopedic before the final orthopedic implants are permanently implanted. It should further be noted that the peripheral flange is only one modification that may be make to differentiate a guide from a trial. In certain circumstances, the guides disclosed herein may be utilized as trials without having any structural changes in that the tibial tray inserts are configured to engage the guides for test fitting, thereby allowing the guides to function as trials too.

An exemplary sequence will now be described for use of the exemplary tibial guides and trials. In particular, those skilled in the art are familiar with total knee arthroplasty. Accordingly, a detailed discussion of all procedures performed is unnecessary and certain procedures have been omitted in furtherance of brevity. In order to prepare the tibia for implantation of an orthopedic component, the surgeon resects the tibia to remove the proximal end of the tibia to leave a relatively planar surface to which the eventual tibial tray implant will sit. After the tibia has been resected, the surgeon obtains a medial or lateral guide and places the guide on the resected surface. In the case of a mass-customized guide, the surgeon will choose a guide size and orient the guide so that the outer periphery of the guide best matches or aligns with the outline of the resected tibia. While this positioning is not as precise as a patient specific approach, it nonetheless provides greater accuracy to replicate natural kinematics that using mechanical alignment techniques. In the context of a patient-specific guide, the surgeon will orient the guide to precisely overlay and align the guide so that the outer contours of the guide match or align themselves with the same contours of the resected tibia.

In either instance, after positioning the guide on top of the resected tibia and aligning the guide, the surgeon can than make a mark, indicia, or other visual representation onto the surface of the resected tibia by using one of the openings of the guide. By way of example, one of the through openings in the guide may be oriented in parallel to the femoral post condylar axis. If the surgeon wishes to align the tibial tray component with respect to this reference axis, the surgeon may use a punch and drive it through the opening in the guide in order to make an indentation into the surface of the resected femur. In addition or alternatively, the surgeon may use a biologically acceptable marker and draw the reference axis onto the resected tibia using the guide to orient the mark.

As discussed previously, the guides in accordance with the instant disclosure may provide openings that allow for one or more reference axes or planes to be carried over to the resected tibia from the femur. The surgeon, depending upon his preference, may use one or more of these openings to make marks or other visually perceptible notations upon the resected tibia that will remain as one or more points of reference. After making one or more marks, the guide may be removed from the tibia.

In an instance where the guide doubles as a trial tibial tray, post markings, the surgeon may retain the guide/trial on top of the resected tibia and mount to it one or more tibial tray insert trials that allow the surgeon to test the size and orientation of the ultimate tibial tray and tray insert. When using the guide that doubles as a trial, the surgeon may nonetheless make any markings desired onto the resected tibia and thereafter remove the tibia guide/trial to carry out further procedures to prepare the resected tibia to receive the final tibial tray implant. But it should be note that, for example, it is within the scope of the disclosure for the guide/trial to include a large enough opening to accommodate through put of a broach or other reaming instrument while retaining the guide/trial in position on top of the resected tibia.

In addition to tibial guides, the present disclosure also provides for tibial tray orthopedic implants that are mass customized and patient-specific. The orthopedic components may be fabricated precisely as discussed above with respect to the guides and trials in terms of the shape of the tibial tray and, in addition, include a tibial stem adapter on the underside of the plate that receives a tibial tray stem. Accordingly, a detailed description that is redundant process of creating one or more bone models, calculating relevant landmarks for the bones of the model, performing a virtual tibia resection along with accounting for expected cut deviations, creation of plate contours that account for soft tissue and thereafter aligning various axes and planes with respect to the resected tibia, and in the case of a mass customize implant, extracting the contour features and clustering the contour features to establish one or more shapes and sizes that account for soft tissue retention (e.g., the posterior cruciate ligament), with respect to the creation of tibial tray plates has been omitted in furtherance of brevity. Nevertheless, to the extent necessary for basis in claiming a mass customized or patient-specific tibial tray orthopedic implant, the prior disclosure directed to fabricating guides and trials is incorporated herein by reference.

Figure 96:
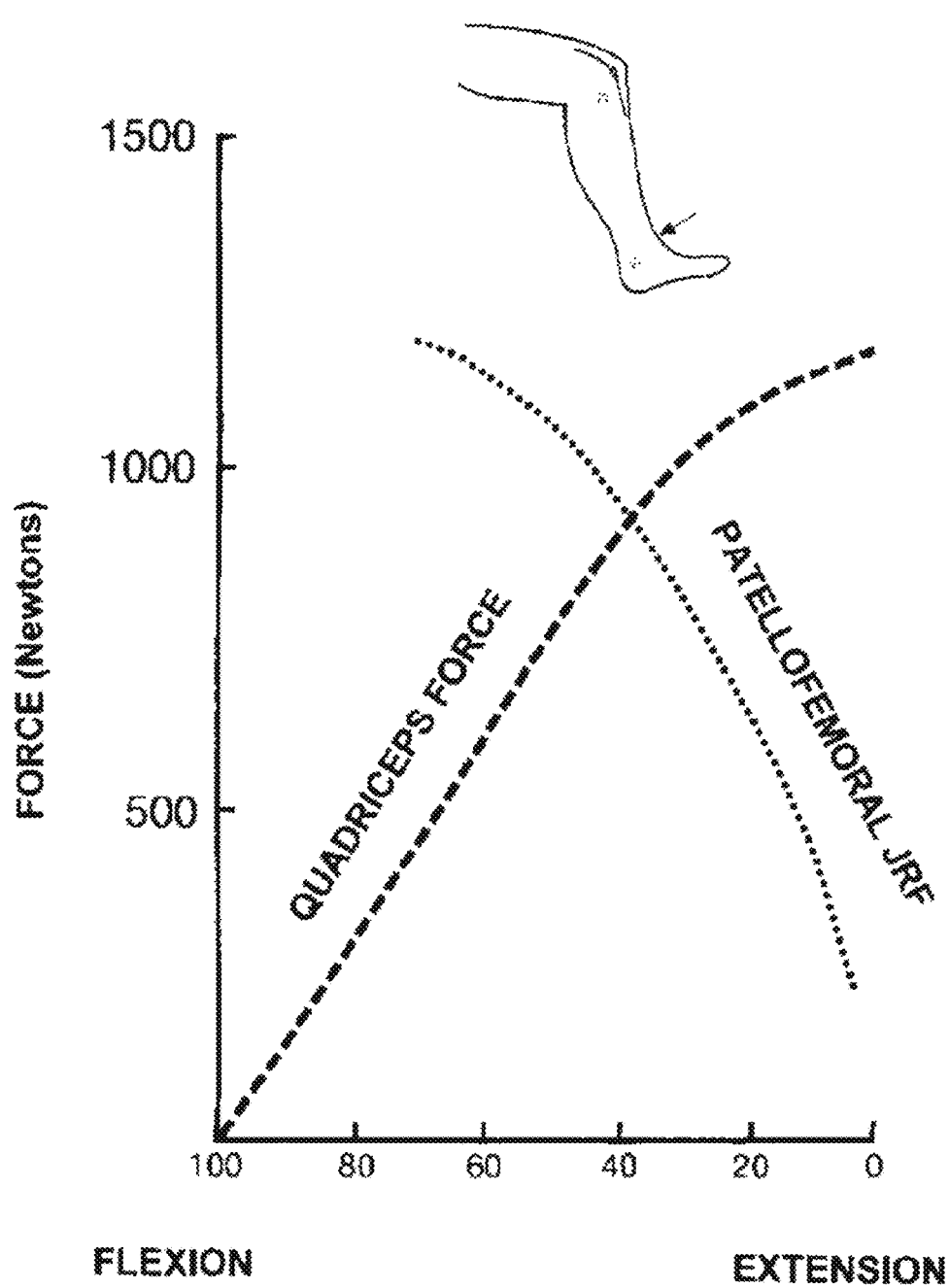
FIG. 96 is a plot showing how quadriceps force changes as a function of knee flexion.

While the foregoing disclosure has been directed to the tibial side of a knee arthroplasty procedure, many of the foregoing processes and techniques are applicable to the femur and alignment of the femoral orthopedic implant component. By way of introduction, when the knee is in significant flexion, a large component of quadriceps force compresses the patella against the femur (see FIG. 96). The resultant joint stress is dictated by the size of the patellofemoral contact area, and patellofemoral cartilage congruity determines that surface area. Conversely, when the knee is at or near full extension, the quadriceps generates predominantly tibiofemoral compression in addition to the ground reaction generated by both the head, arm and trunk (HAT) and the limb in swing phase. Therefore, joint stress in the extended knee is dictated primarily by tibiofemoral cartilage congruity. Moreover, this curve explains why patients with patellofemoral joint derangements are able to perform physical exercise against resistance with less pain if the knee flexion is kept lower than 20 degrees.

The adult human knee is thus a complex interaction product of its habitual motion pattern as produced by the interactions of condylar form and ligamentous restraint, dictated by positional information, and cartilage/fibrous tissue modeling throughout ontogeny. As a consequence, when both processes ceased development at adulthood, the myriad fiber lengths within its restraint systems have remained congruent with the joint's condylar surface geometry, and in the adult will continue to work together, maintaining a normal stereotyped motion pattern such that the velocity vectors of the two rigid bodies are uniformly tangent to their points of contact throughout the joint's normal range of motion (See FIG. 104).

Figure 97:
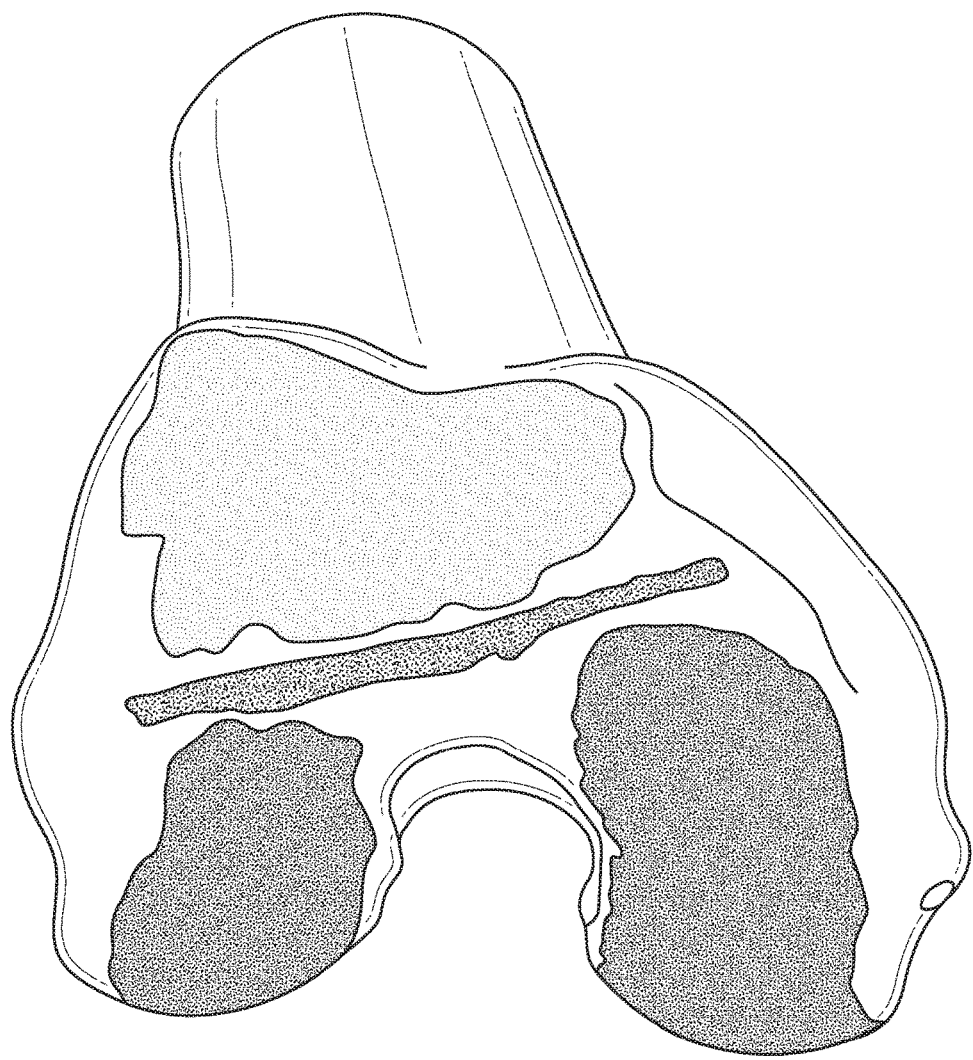
FIG. 97 is a picture of a distal femur tangible model marked up to show the medial boss as a blue line.
Figures 98A, 98B, 98C, 98D:
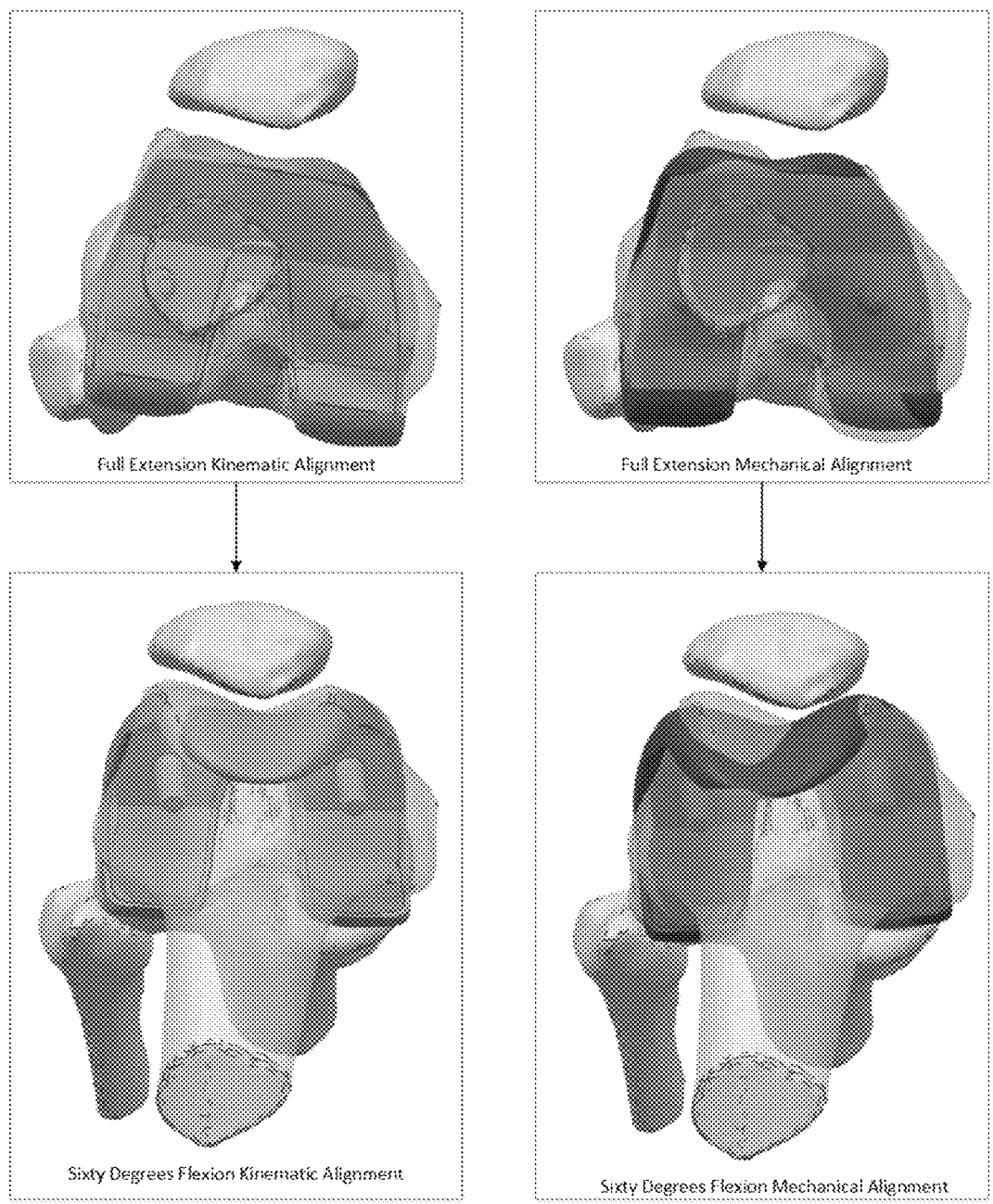
FIGS. 98A-98D are a series of views comparing the position of the femoral component of a TKA using mechanical alignment and kinematic alignment and how the patella cannot track the femoral component properly using mechanical alignment.

Such modeling provides an explanation for a unique feature of the human knee, its medial condylar boss (see FIG. 97). This structure is obviously present in both dissections and dry specimens and truly reflects its contact throughout development, to the medial meniscus. It is never seen in the distal femur of other primates or mammals, and is a distinct, spiral, surface swelling of the medial condylar surface immediately distal to its meniscal groove (i.e., the "medial oblique groove" of the femur).

As mentioned previously, the combination of cartilage modeling and the habitual contact of the distal femoral surface with the anterior portion of the medial and lateral menisci leaves small corresponding grooves on the dry femur, the medial and lateral meniscal grooves. A line connecting these grooves, the meniscal axis (see FIG. 97, blue line), thus defines the position of the tibial plateau during full extension of the joint. This axis can be used to functionally orient the femur for further anatomical observation (see FIGS. 94A-94D).

As seen in FIGS. 95A, 95B, 98A-98D, 99A, and 99B, kinematically aligned components will have different patellofemoral forces than mechanical alignment in both extension and flexion. From published clinical results and visible in FIGS. 98A-98D, during flexion the location of trochlear groove is close to the normal anatomy in kinematically aligned knees—indicating potentially improved patellofemoral function during flexion. In extension, however, current implants lateralize the patella in mechanically neutral alignment, reducing patellofemoral forces in extension. When existing components are placed in kinematic alignment, there are increased patellofemoral forces in extension.

Previous systems must strike a balance between performance in flexion and performance in extension.

Figures 99A, 99B:
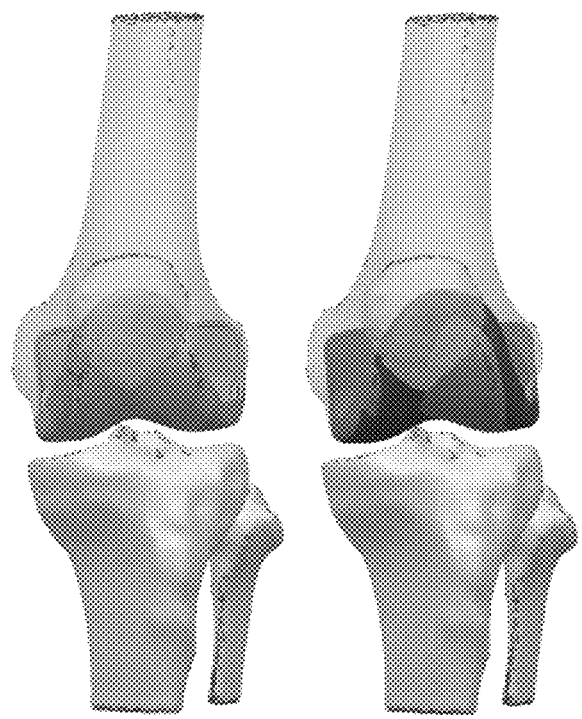
FIGS. 99A and 99B are comparative frontal views of femoral components placed via mechanical alignment (99A) and via kinematic alignment (99B).
Figures 100A, 100B:
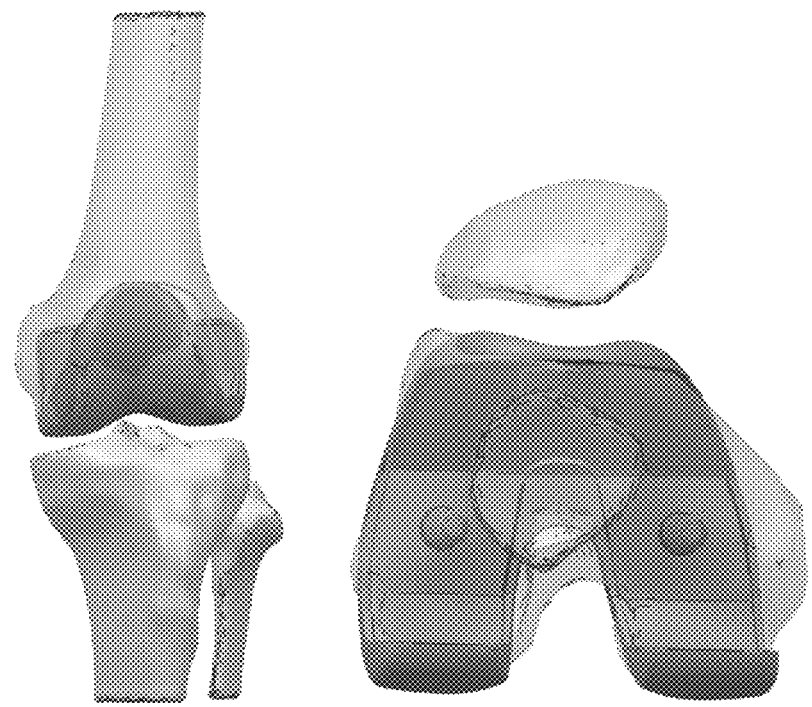
FIGS. 100A and 100B are frontal and overhead views showing how current femoral components should be modified to account for correct kinematic alignment.
Figures 103A, 103B, 103C:
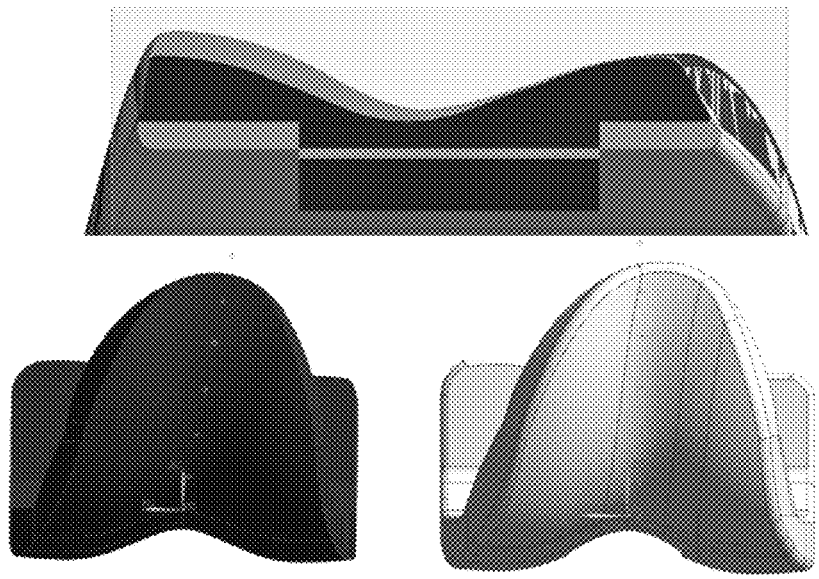
FIGS. 103A-103C are a series of images highlighting the differences in shape between the current day femoral component (FIG. 103A) and a femoral component designed in accordance with the instant disclosure (FIG. 103B) and how the design shapes compare to one another near the end of the trochlear groove (FIG. 103C).

Using the meniscal axis in FIG. 97, the femoral surface can be functionally divided into flexion (red in FIG. 97) and extension surfaces (orange in FIG. 97). The extension surface for use in kinematic alignment can be optimized in a way that reduces risk of subluxation in multiple ways. First, if it is desirable to keep the natural trochlear groove Q angle, the lateral aspect of the anterior flange must be raised to resist the increased patellofemoral forces (relative to current designs). This raised aspect is seen in FIG. 103C. An alternative is to widen, or lateralize the patellar groove in extension, reducing Q angle and thus reducing patellofemoral forces. A suggested widening of the groove and increase in lateral surface area are seen in FIGS. 100A, 100B. FIGS. 99A and 99B show reduction in lateral anterior surface area for a kinematically aligned femoral component (left) versus the mechanically aligned femoral component (right).

Figure 101:
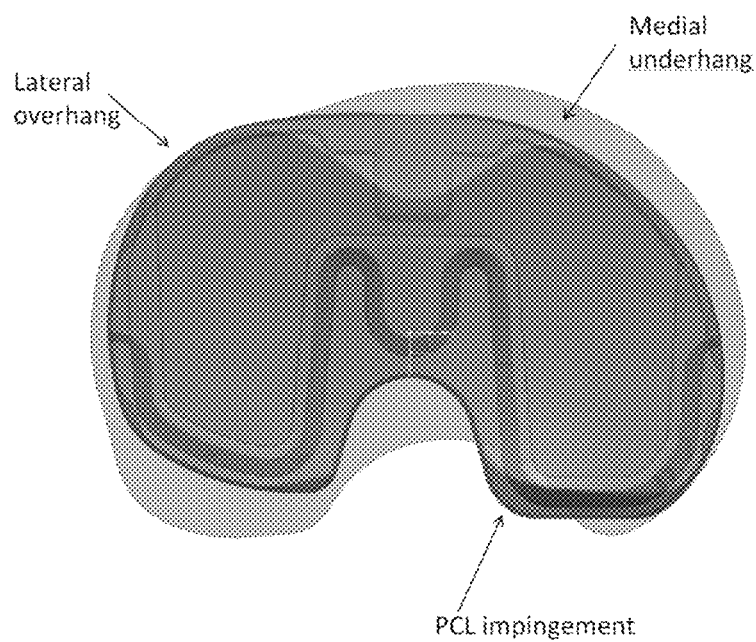
FIG. 101 is an image of a commercially available tibial tray properly aligned via kinematic alignment, yet continuing to show posterior cruciate ligament impingement, thus necessitating a revised design implant to avoid impingement and be properly kinematically aligned when mounted to the resected tibia.
Figure 102:
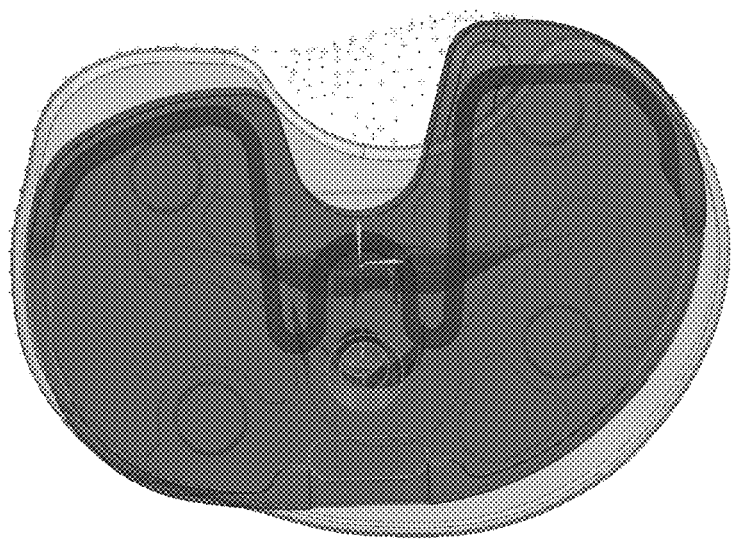
FIG. 102 is a similar image to FIG. 101 showing posterior cruciate ligament impingement using a present day implant when kinematically aligned, with the posterior cruciate ligament represented by its most likely locations from the statistical atlas.

The tibial footprint of existing systems also can benefit from optimization for kinematic alignment. FIGS. 101 and 102 provide overlays of existing system and kinematic alignment plate design, highlighting potential issues with current designs that often require undersizing of the component due to anterior overhang or impingement with the posterior cruciate ligament. Using process outlined in FIG. 104, the footprint of the tibial implant can be matched to the anatomy when in kinematic alignment.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A method of using a tibial component placement guide for use in a knee arthroplasty procedure involving a knee joint comprising a tibia, a patella, and a femur, the method comprising:
    applying an overlay to a resected tibia, the overlay including at least one of an indicia and an opening indicative of at least one of an orientation and a position of a projected axis comprising at least one of a posterior condylar femoral axis, a spherical femoral axis, a cylindrical femoral axis, a flexion axis of the femur about the tibia, and a helical axis of the femur relative to the tibia;
    marking the resected tibia with at least one mark using the overlay to denote at least one of an orientation and a position of the projected axis; and,
    orienting and attaching at least one of an orthopedic tibial tray trial and an orthopedic tibial tray to the resected tibia using the mark.

2. The method of claim 1, wherein the step of applying the overlay includes aligning a peripheral shape of the overlay with a peripheral shape of the resected tibia and placing the overlay on top of the resected tibia.

3. The method of claim 1, wherein the overlay includes an opening indicative of the orientation of the projected axis.

4. The method of claim 3, wherein the opening comprises a through hole.

5. The method of claim 4, wherein:
    the through hole outlines a T-shape;
    a horizontal aspect of the T-shape is indicative of orientation of the projected axis; and,
    a vertical aspect of the T-shape is indicative of orientation of the projected axis.

6. The method of claim 4, wherein:
    the through hole outlines a + shape;
    a horizontal aspect of the + shape is indicative of orientation of the projected axis; and,
    a vertical aspect of the + shape is indicative of orientation of the projected axis.

7. The method of claim 3, wherein:
    the opening comprises a first through hole and a second through hole;
    the first through hole is indicative of the projected axis; and,
    the second through hole is indicative of orientation of the projected axis.

8. The method of claim 3, wherein:
    the opening comprises a first cutout and a second cutout;
    the first cutout is indicative of the projected axis; and,
    the second cutout is indicative of orientation of the projected axis.

9. The method of claim 1, wherein the projected axis comprises the posterior condylar femoral axis.

10. The method of claim 1, wherein the projected axis comprises the helical axis of the femur relative to the tibia.

11. The method of claim 1, wherein the overlay has a contour outline that is aligned with the resected tibia.

12. The method of claim 11, wherein the contour outline is patient-specific.

13. The method of claim 1, further comprising at least one of an indicia and an opening indicative of at least two of a medial guide, a lateral guide, a size of the guide, and a particular patient.

14. The method of claim 1, wherein the guide is fabricated from at least one of titanium, a titanium alloy, stainless steel, and a stainless steel alloy.

15. The method of claim 1, wherein the guide includes a through aperture configured to align a through fastener mounted to the resected tibia.

16. The method of claim 15, wherein the through fastener comprises a pin.

17. The method of claim 16, wherein:
    the through aperture comprises a plurality of through apertures;
    each of the plurality of apertures is configured to receive a pin.

18. The method of claim 1, wherein the overlay comprises a base plate.

19. The method of claim 18, wherein the base plate includes a flange along a periphery of the base plate.

20. The method of claim 1, wherein the overlay further comprises at least one of an indicia and an opening indicative of the orientation of a third axis of the femur, the third axis being parallel to the projected axis.

21. The method of claim 1, wherein:
    the at least one mark comprises an indentation formed into the resected tibia; and,
    the step of marking the resected tibia includes using a punch to form the indentation into the resected tibia.

22. The method of claim 1, wherein:
    the at least one mark comprises a representation formed into the resected tibia; and,
    the step of marking the resected tibia includes writing the representation onto the resected tibia.

23. The method of claim 1, wherein the orienting and attaching step includes orienting and attaching an orthopedic tibial tray to the resected tibia using the mark.

24. The method of claim 1, further comprising removing the overlay prior to orienting and attaching at least one of the orthopedic tibial tray trial and the orthopedic tibial tray to the resected tibia using the mark.

25. The method of claim 1, wherein the overlay includes a contour on a posterior side accounting for retention of the posterior cruciate ligament.

* * * * *